United States Patent
Yates et al.

(10) Patent No.: US 11,026,682 B2
(45) Date of Patent: Jun. 8, 2021

(54) SURGICAL INSTRUMENT BATTERY PACK WITH VOLTAGE POLLING

(71) Applicant: ETHICON LLC, Guaynabo, PR (US)

(72) Inventors: David C. Yates, West Chester, OH (US); Frederick E. Shelton, IV, Hillsboro, OH (US)

(73) Assignee: Cilag GmbH International, Zug (CH)

( * ) Notice: Subject to any disclaimer, the term of this patent is extended or adjusted under 35 U.S.C. 154(b) by 203 days.

(21) Appl. No.: 15/964,427

(22) Filed: Apr. 27, 2018

(65) Prior Publication Data

US 2018/0310933 A1  Nov. 1, 2018

Related U.S. Application Data

(63) Continuation of application No. 14/514,417, filed on Oct. 15, 2014, now Pat. No. 9,974,539.

(51) Int. Cl.
*H01M 10/46* (2006.01)
*A61B 17/072* (2006.01)
(Continued)

(52) U.S. Cl.
CPC ...... *A61B 17/072* (2013.01); *A61B 17/07207* (2013.01); *H01M 10/425* (2013.01);
(Continued)

(58) Field of Classification Search
CPC ...... H02J 7/0003; H02J 7/0004; H02J 7/0008; H02J 7/0026; H02J 7/0021; H02J 7/0034;
(Continued)

(56) References Cited

U.S. PATENT DOCUMENTS 4,805,823 A 2/1989 Rothfuss
4,840,583 A 6/1989 Moore
(Continued)

FOREIGN PATENT DOCUMENTS

CN 201437021 U 4/2010
CN 103339586 A 10/2013
(Continued)

OTHER PUBLICATIONS

European Communication dated Jun. 11, 2018 for Application No. 15189693.3, 7 pages.
(Continued)

*Primary Examiner* — Edward Tso
(74) *Attorney, Agent, or Firm* — Frost Brown Todd LLC

(57) ABSTRACT

A method of operating a medical device comprises electrically connecting a power device to the medical device. The method further comprises sensing at least one characteristic of the medical device with the power device. The method further comprises adjusting or maintaining one or more characteristics of an electrical connection feature of the power device according to the at least one observed characteristic such that the electrical connection feature of the power device is operationally compatible with an electrical connection feature of the medical device. The method further comprises operating the power device according to an operational profile associated with the medical device.

20 Claims, 33 Drawing Sheets

(51) Int. Cl.
| | |
|---|---|
| *H02J 7/00* | (2006.01) |
| *H01M 10/42* | (2006.01) |
| *H01M 50/597* | (2021.01) |
| H02J 1/06 | (2006.01) |
| A61B 17/00 | (2006.01) |
| H01M 10/0525 | (2010.01) |
| H04Q 9/00 | (2006.01) |
| H01M 10/48 | (2006.01) |
| G01R 31/36 | (2020.01) |
| A61B 90/00 | (2016.01) |
| A61B 17/29 | (2006.01) |

(52) U.S. Cl.
CPC ..... *H01M 10/4257* (2013.01); *H01M 50/597* (2021.01); *H02J 7/0021* (2013.01); *H02J 7/0036* (2013.01); *H02J 7/0044* (2013.01); *H02J 7/0047* (2013.01); *H02J 7/0063* (2013.01); *A61B 2017/00017* (2013.01); *A61B 2017/0046* (2013.01); *A61B 2017/00115* (2013.01); *A61B 2017/00398* (2013.01); *A61B 2017/00407* (2013.01); *A61B 2017/00734* (2013.01); *A61B 2017/07271* (2013.01); *A61B 2017/2927* (2013.01); *A61B 2090/0814* (2016.02); *G01R 31/36* (2013.01); *H01M 10/0525* (2013.01); *H01M 10/48* (2013.01); *H01M 2010/4271* (2013.01); *H01M 2010/4278* (2013.01); *H01M 2200/30* (2013.01); *H01M 2220/30* (2013.01); *H02J 1/06* (2013.01); *H02J 7/0048* (2020.01); *H02J 2007/0067* (2013.01); *H04Q 9/00* (2013.01)

(58) Field of Classification Search
CPC .................. H02J 7/0029; H02J 7/0045; A61B 2090/0804–0806; A61B 2090/0808; A61B 2017/00017; A61B 2017/00734; A61B 2017/0003
USPC ....... 320/107, 106, 115, 116, 132, 134, 136, 320/165
See application file for complete search history.

(56) References Cited

U.S. PATENT DOCUMENTS

| | | | | |
|---|---|---|---|---|
| 4,871,957 | A | * | 10/1989 | Taranto ................ H01R 11/24 320/105 |
| 4,994,727 | A | * | 2/1991 | Yang ..................... H02J 7/0034 320/DIG. 22 |
| 5,415,334 | A | | 5/1995 | Williamson et al. |
| 5,465,895 | A | | 11/1995 | Knodel et al. |
| 5,597,107 | A | | 1/1997 | Knodel et al. |
| 5,632,432 | A | | 5/1997 | Schulze et al. |
| 5,673,840 | A | | 10/1997 | Schulze et al. |
| 5,704,534 | A | | 1/1998 | Huitema et al. |
| 5,814,055 | A | | 9/1998 | Knodel et al. |
| 5,838,143 | A | | 11/1998 | Lo |
| 5,965,998 | A | * | 10/1999 | Whiting ................ H02J 7/0029 320/165 |
| 6,978,921 | B2 | | 12/2005 | Shelton et al. |
| 7,000,818 | B2 | | 2/2006 | Shelton et al. |
| 7,143,923 | B2 | | 12/2006 | Shelton et al. |
| 7,303,108 | B2 | | 12/2007 | Shelton |
| 7,367,485 | B2 | | 5/2008 | Shelton et al. |
| 7,380,695 | B2 | | 6/2008 | Doll et al. |
| 7,380,696 | B2 | | 6/2008 | Shelton et al. |
| 7,404,508 | B2 | | 7/2008 | Smith et al. |
| 7,434,715 | B2 | | 10/2008 | Shelton et al. |
| 7,721,930 | B2 | | 5/2010 | McKenna et al. |
| 8,054,049 | B1 | | 11/2011 | Michaelis |
| 8,184,839 | B2 | | 5/2012 | Gudmundsen et al. |
| 8,192,359 | B2 | | 6/2012 | Kusakabe et al. |
| 8,210,411 | B2 | | 7/2012 | Yates et al. |
| 8,408,439 | B2 | | 4/2013 | Huang et al. |
| 8,431,263 | B2 | | 4/2013 | Shuster |
| 8,453,914 | B2 | | 6/2013 | Laurent et al. |
| 8,608,045 | B2 | | 12/2013 | Smith et al. |
| 9,072,535 | B2 | | 7/2015 | Shelton, IV et al. |
| 9,107,690 | B2 | * | 8/2015 | Bales, Jr. ........ A61B 17/320092 |
| 9,186,142 | B2 | | 11/2015 | Fanelli et al. |
| 9,219,375 | B2 | * | 12/2015 | Woods ................ H02J 7/0021 |
| 9,345,481 | B2 | | 5/2016 | Hall et al. |
| 9,350,051 | B2 | | 5/2016 | Teramoto et al. |
| 9,517,065 | B2 | | 12/2016 | Simms et al. |
| 9,622,746 | B2 | | 4/2017 | Simms et al. |
| 9,717,497 | B2 | | 8/2017 | Zerkle et al. |
| 9,795,379 | B2 | | 10/2017 | Leimbach et al. |
| 9,808,248 | B2 | | 11/2017 | Hoffman |
| 9,839,421 | B2 | | 12/2017 | Zerkle et al. |
| 9,867,615 | B2 | | 1/2018 | Fanelli et al. |
| 9,913,642 | B2 | | 3/2018 | Leimbach et al. |
| 9,974,539 | B2 | | 5/2018 | Yates et al. |
| 10,090,498 | B2 | | 10/2018 | Olsson et al. |
| 10,092,292 | B2 | | 10/2018 | Boudreaux et al. |
| 10,105,140 | B2 | | 10/2018 | Malinouskas et al. |
| 2009/0090763 | A1 | | 4/2009 | Zemlok et al. |
| 2010/0176766 | A1 | | 7/2010 | Brandner et al. |
| 2012/0179159 | A1 | | 7/2012 | Krapohl |
| 2012/0247796 | A1 | | 10/2012 | Mueller et al. |
| 2013/0015824 | A1 | * | 1/2013 | Newton ................ H02J 7/0034 320/165 |
| 2014/0263541 | A1 | | 9/2014 | Leimbach et al. |
| 2014/0263552 | A1 | | 9/2014 | Hall et al. |
| 2014/0263554 | A1 | | 9/2014 | Leimbach et al. |
| 2015/0374361 | A1 | | 12/2015 | Gettinger et al. |
| 2015/0374373 | A1 | | 12/2015 | Rector et al. |

FOREIGN PATENT DOCUMENTS

| | | |
|---|---|---|
| CN | 103904898 A | 7/2014 |
| EP | 2 510 891 A1 | 10/2012 |
| JP | 2008-517578 A | 5/2008 |
| JP | 2012-223582 A | 11/2012 |
| WO | WO 2013/074485 A2 | 5/2013 |

OTHER PUBLICATIONS

European Communication dated Feb. 26, 2019 for Application No. 15189693.3, 5 pages.
European Communication dated Oct. 16, 2019 for Application No. 15189693.3, 7 pages.
Japanese Office Action dated Sep. 17, 2019 for Application No. 2017-520402, 4 pages.
"Inductive sensor," Wikipedia, the free encyclopedia, Sep. 1, 2014, downloaded from https://en.wikipedia.org/w/index.php?title=Inductive_sensor&oldid=623738761, XP055256750, 1 pg.
European Search Report, Partial, dated Jan. 25, 2016 for Application No. EP 15189693.3, 9 pgs.
European Search Report, Extended, and Written Opinion dated May 23, 2016 for Application No. EP 15189693.3, 16 pgs.
European Examination Report dated Oct. 23, 2017 for Application No. EP 15189693.3, 6 pgs.
International Search Report and Written Opinion dated Mar. 18, 2016 for Application No. PCT/US2015/052574, 20 pgs.
U.S. Appl. No. 61/782,866, filed Mar. 14, 2013.
Chinese Office Action, The First Office Action, and Search Report dated Sep. 2, 2020 for Application No. CN 201580068453.0, 18 pgs.
European Examination Report dated Jul. 28, 2020 for Application No. EP 15189693.3, 4 pgs.
Indian Office Action dated Jan. 29, 2020 for Application No. IN 201717013173, 5 pgs.

* cited by examiner

SURGICAL INSTRUMENT BATTERY PACK WITH VOLTAGE POLLING

This application is a continuation of U.S. patent application Ser. No. 14/514,417, entitled "Surgical Instrument Battery Pack with Voltage Polling," filed Oct. 15, 2014 and issued as U.S. Pat. No. 9,974,539 on May 22, 2018.

BACKGROUND

In some settings, endoscopic surgical instruments may be preferred over traditional open surgical devices since a smaller incision may reduce the post-operative recovery time and complications. Consequently, some endoscopic surgical instruments may be suitable for placement of a distal end effector at a desired surgical site through the cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasonic vibration, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient. Positioning of an end effector may be further facilitated through inclusion of one or more articulation joints or features, enabling the end effector to be selectively articulated or otherwise deflected relative to the longitudinal axis of the shaft.

Examples of endoscopic surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Merely exemplary surgical staplers are disclosed in U.S. Pat. No. 4,805,823, entitled "Pocket Configuration for Internal Organ Staplers," issued Feb. 21, 1989; U.S. Pat. No. 5,415,334, entitled "Surgical Stapler and Staple Cartridge," issued May 16, 1995; U.S. Pat. No. 5,465,895, entitled "Surgical Stapler Instrument," issued Nov. 14, 1995; U.S. Pat. No. 5,597,107, entitled "Surgical Stapler Instrument," issued Jan. 28, 1997; U.S. Pat. No. 5,632,432, entitled "Surgical Instrument," issued May 27, 1997; U.S. Pat. No. 5,673,840, entitled "Surgical Instrument," issued Oct. 7, 1997; U.S. Pat. No. 5,704,534, entitled "Articulation Assembly for Surgical Instruments," issued Jan. 6, 1998; U.S. Pat. No. 5,814,055, entitled "Surgical Clamping Mechanism," issued Sep. 29, 1998; U.S. Pat. No. 6,978,921, entitled "Surgical Stapling Instrument Incorporating an E-Beam Firing Mechanism," issued Dec. 27, 2005; U.S. Pat. No. 7,000,818, entitled "Surgical Stapling Instrument Having Separate Distinct Closing and Firing Systems," issued Feb. 21, 2006; U.S. Pat. No. 7,143,923, entitled "Surgical Stapling Instrument Having a Firing Lockout for an Unclosed Anvil," issued Dec. 5, 2006; U.S. Pat. No. 7,303,108, entitled "Surgical Stapling Instrument Incorporating a Multi-Stroke Firing Mechanism with a Flexible Rack," issued Dec. 4, 2007; U.S. Pat. No. 7,367,485, entitled "Surgical Stapling Instrument Incorporating a Multistroke Firing Mechanism Having a Rotary Transmission," issued May 6, 2008; U.S. Pat. No. 7,380,695, entitled "Surgical Stapling Instrument Having a Single Lockout Mechanism for Prevention of Firing," issued Jun. 3, 2008; U.S. Pat. No. 7,380,696, entitled "Articulating Surgical Stapling Instrument Incorporating a Two-Piece E-Beam Firing Mechanism," issued Jun. 3, 2008; U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; and U.S. Pat. No. 8,453,914, entitled "Motor-Driven Surgical Cutting Instrument with Electric Actuator Directional Control Assembly," issued Jun. 4, 2013. The disclosure of each of the above-cited U.S. Patents is incorporated by reference herein.

While the surgical staplers referred to above are described as being used in endoscopic procedures, it should be understood that such surgical staplers may also be used in open procedures and/or other non-endoscopic procedures. By way of example only, a surgical stapler may be inserted through a thoracotomy, and thereby between a patient's ribs, to reach one or more organs in a thoracic surgical procedure that does not use a trocar as a conduit for the stapler. Such procedures may include the use of the stapler to sever and close a vessel leading to a lung. For instance, the vessels leading to an organ may be severed and closed by a stapler before removal of the organ from the thoracic cavity. Of course, surgical staplers may be used in various other settings and procedures.

Examples of surgical staplers that may be particularly suited or use through a thoracotomy are disclosed in U.S. Patent Application Publication No. 2014/0243801, entitled "Surgical Instrument End Effector Articulation Drive with Pinion and Opposing Racks," published on Aug. 28, 2014, now U.S. Pat. No. 9,186,142, issued Nov. 17, 2015; U.S. Patent Application Publication No. 2014/0239041, entitled "Lockout Feature for Movable Cutting Member of Surgical Instrument," Published Aug. 28, 2014, now U.S. Pat. No. 9,717,497, issued Aug. 1, 2017; U.S. Patent Application Publication No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; U.S. Patent Application Publication No. 2014/0239036, entitled "Jaw Closure Feature for End Effector of Surgical Instrument," Published Aug. 28, 2014, now U.S. Pat. No. 9,839,421, issued Dec. 12, 2017; U.S. Patent Application Publication No. 2014/0239040, entitled "Surgical Instrument with Articulation Lock having a Detenting Binary Spring," published Aug. 24, 2014, now U.S. Pat. No. 9,867,615, issued Jan. 16, 2018; U.S. Patent Application Publication No. 2014/0239043, entitled "Distal Tip Features for End Effector of Surgical Instrument," published Aug. 28, 2014, now U.S. Pat. No. 9,622,746, issued Apr. 18, 2017; U.S. Patent Application Publication No. 2014/0239037, entitled "Staple Forming Features for Surgical Stapling Instrument," filed Aug. 28, 2014, issued as U.S. Pat. No. 10,092,292 on Oct. 9, 2018; U.S. Patent Application Publication No. 2014/0239038, entitled "Surgical Instrument with Multi-Diameter Shaft," published Aug. 28, 2014, now U.S. Pat. No. 9,795,379, issued Oct. 24, 2017; and U.S. Patent Application Publication No. 2014/0239044, entitled "Installation Features for Surgical Instrument End Effector Cartridge," published Aug. 28, 2014, now U.S. Pat. No. 9,808,248, issued Nov. 7, 2017. The disclosure of each of the above-cited U.S. Patent Applications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 12-1 depicts a first portion of a circuit diagram of the surgical instrument of FIG. 1;

FIG. 12-2 depicts a second portion of a circuit diagram of the surgical instrument of FIG. 1;

FIG. 28-1 depicts a first portion of a flow chart showing steps carried out during one or more exemplary methods of utilizing the circuit of FIG. 26;

FIG. 28-2 depicts a second portion of a flow chart showing steps carried out during one or more exemplary methods of utilizing the circuit of FIG. 26;

Figure 1:
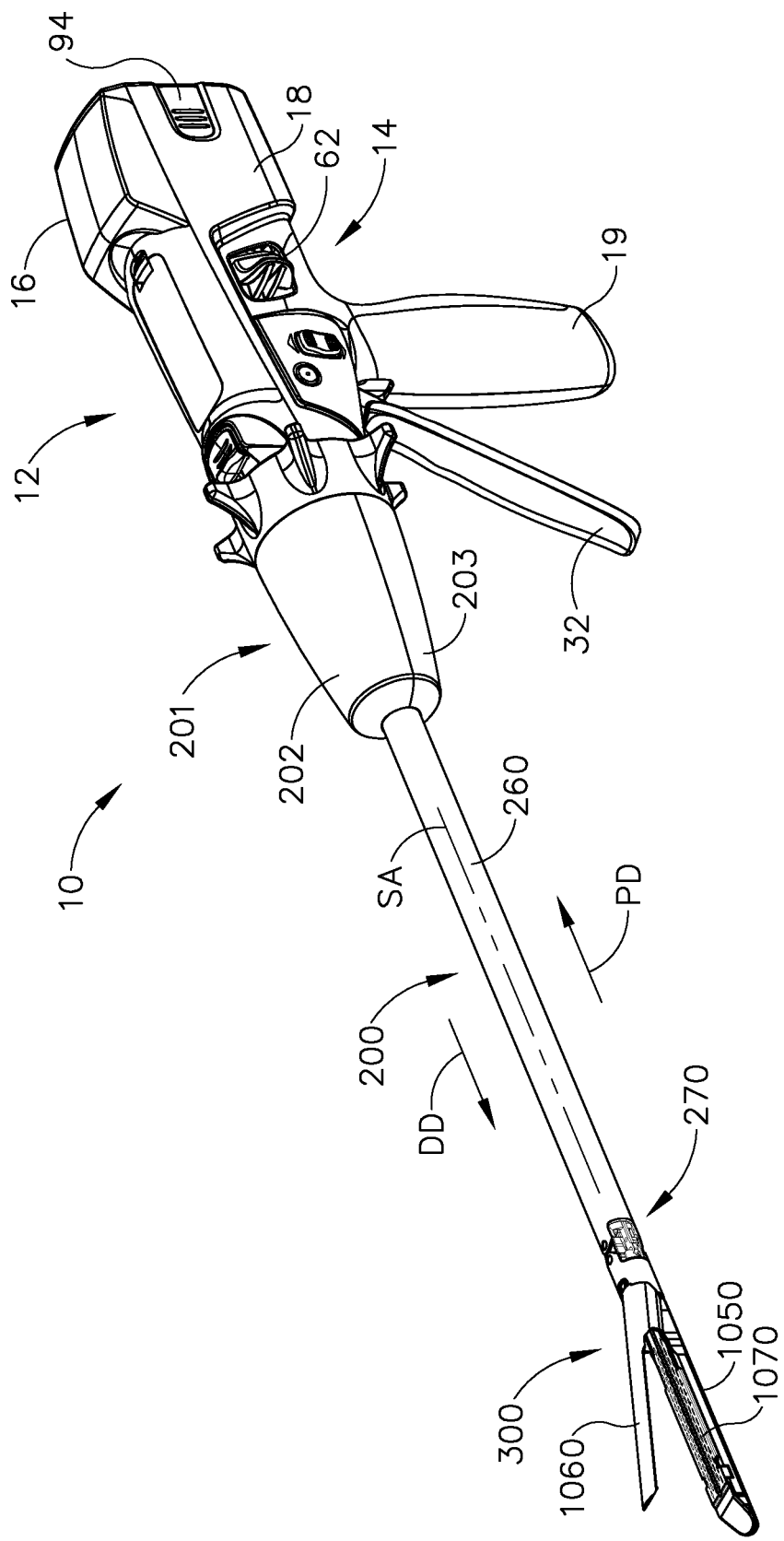
FIG. 1 depicts a perspective view of an exemplary surgical instrument including an interchangeable shaft assembly and a handle assembly.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Exemplary Surgical Instrument

FIGS. 1-6 depict a motor-driven surgical cutting and fastening instrument (10) that may or may not be reused. In the illustrated embodiment, the instrument (10) includes a housing (12) that comprises a handle assembly (14) that is configured to be grasped, manipulated and actuated by the clinician. The housing (12) is configured for operable attachment to an interchangeable shaft assembly (200) that has a surgical end effector (300) operably coupled thereto that is configured to perform one or more surgical tasks or procedures. As the present Detailed Description proceeds, it will be understood that the various unique and novel arrangements of the various forms of interchangeable shaft assemblies disclosed herein may also be effectively employed in connection with robotically-controlled surgical systems. Thus, the term "housing" may also encompass a housing or similar portion of a robotic system that houses or otherwise operably supports at least one drive system that is configured to generate and apply at least one control motion that could be used to actuate the interchangeable shaft assemblies disclosed herein and their respective equivalents. The term "frame" may refer to a portion of a handheld surgical instrument. The term "frame" may also represent a portion of a robotically controlled surgical instrument and/or a portion of the robotic system that may be used to operably control a surgical instrument. For example, the interchangeable shaft assemblies disclosed herein may be employed with various robotic systems, instruments, components and methods disclosed in U.S. Patent Application Publication No. US 2012/0298719, entitled "Surgical Stapling Instruments With Rotatable Staple Deployment Arrangements," published Nov. 29, 2012, now U.S. Pat. No. 9,072,535, issued Jul. 7, 2015, which is incorporated by reference herein in its entirety.

The housing (12) depicted in FIGS. 1-3A is shown in connection with an interchangeable shaft assembly (200) that includes an end effector (300) comprising a surgical cutting and fastening device that is configured to operably support a surgical staple cartridge (1070) therein. The housing (12) may be configured for use in connection with interchangeable shaft assemblies that include end effectors that are adapted to support different sizes and types of staple cartridges, have different shaft lengths, sizes, and types, etc. In addition, the housing (12) may also be effectively employed with a variety of other interchangeable shaft assemblies including those assemblies that are configured to apply other motions and forms of energy such as, for example, radio frequency (RF) energy, ultrasonic energy and/or motion to end effector arrangements adapted for use in connection with various surgical applications and procedures. Furthermore, the end effectors, shaft assemblies, handles, surgical instruments, and/or surgical instrument systems can utilize any suitable fastener, or fasteners, to fasten tissue. For instance, a fastener cartridge comprising a plurality of fasteners removably stored therein can be removably inserted into and/or attached to the end effector of a shaft assembly.

A. Exemplary Handle Assembly

Figure 2:
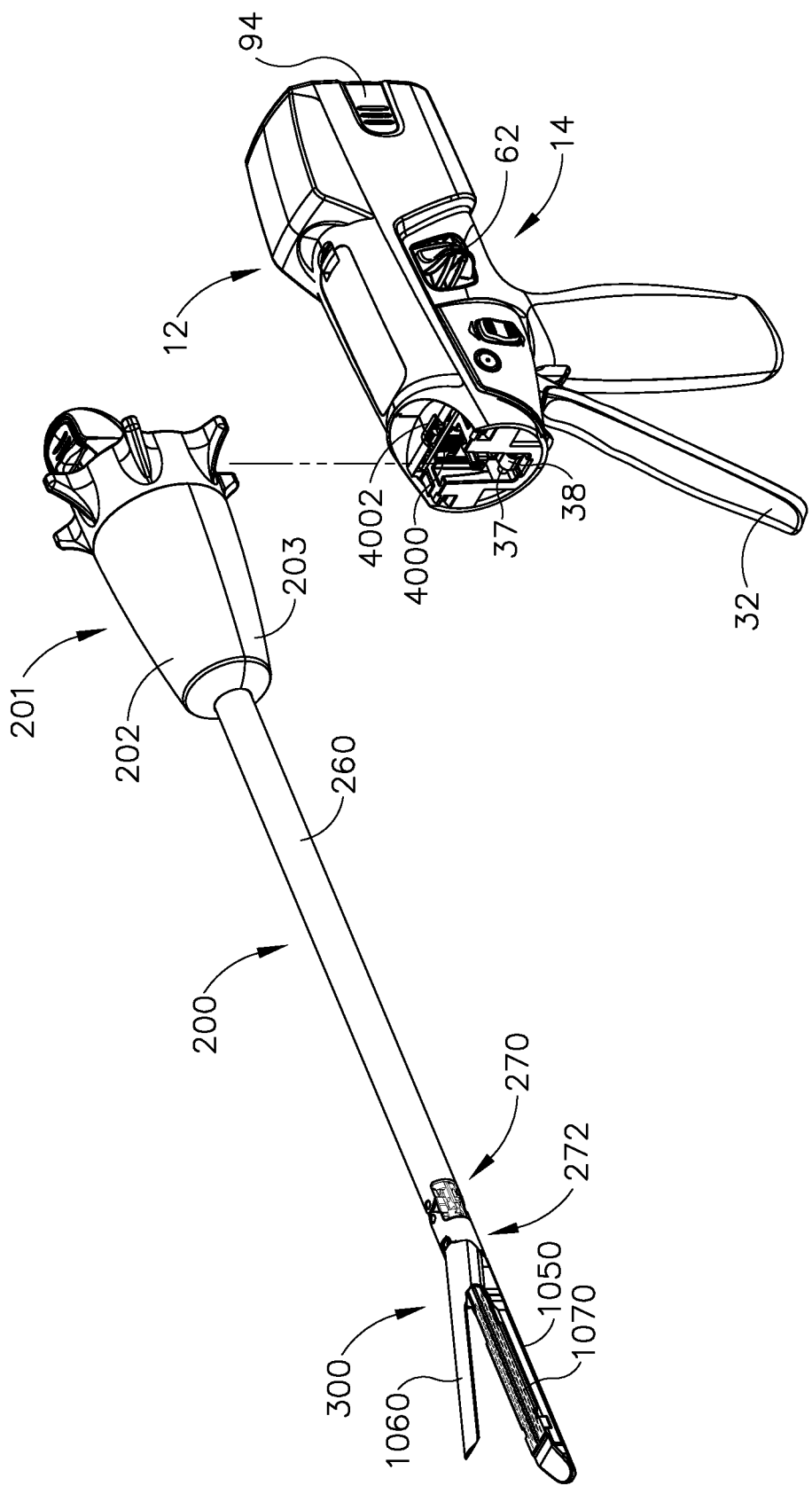
FIG. 2 depicts an perspective view of the instrument of FIG. 1, showing the shaft assembly disassembled from the handle assembly of the instrument.
Figure 3A:
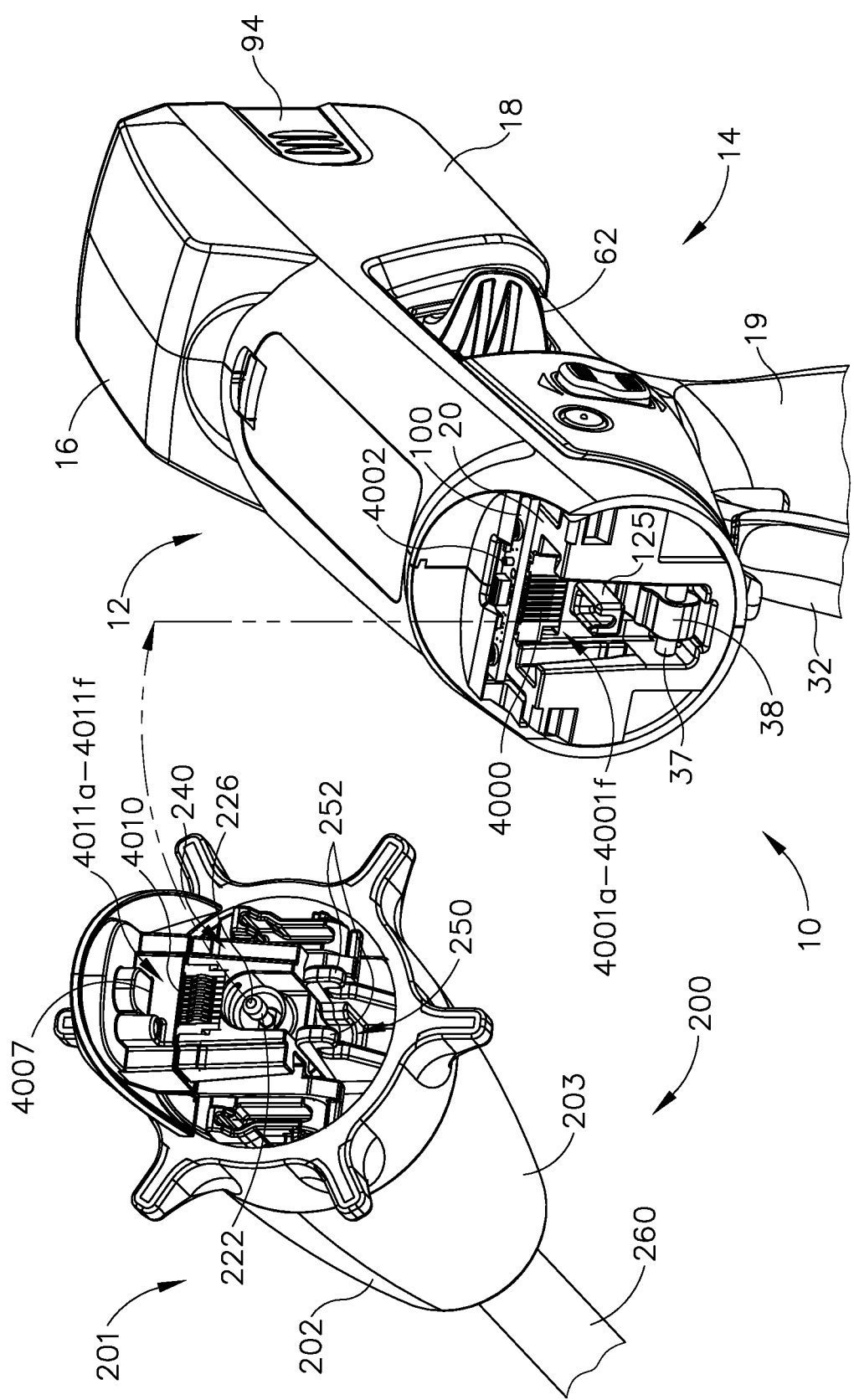
FIG. 3A depicts another perspective view of the instrument of FIG. 1, showing the shaft assembly disassembled from the handle assembly of the instrument.
Figure 4:
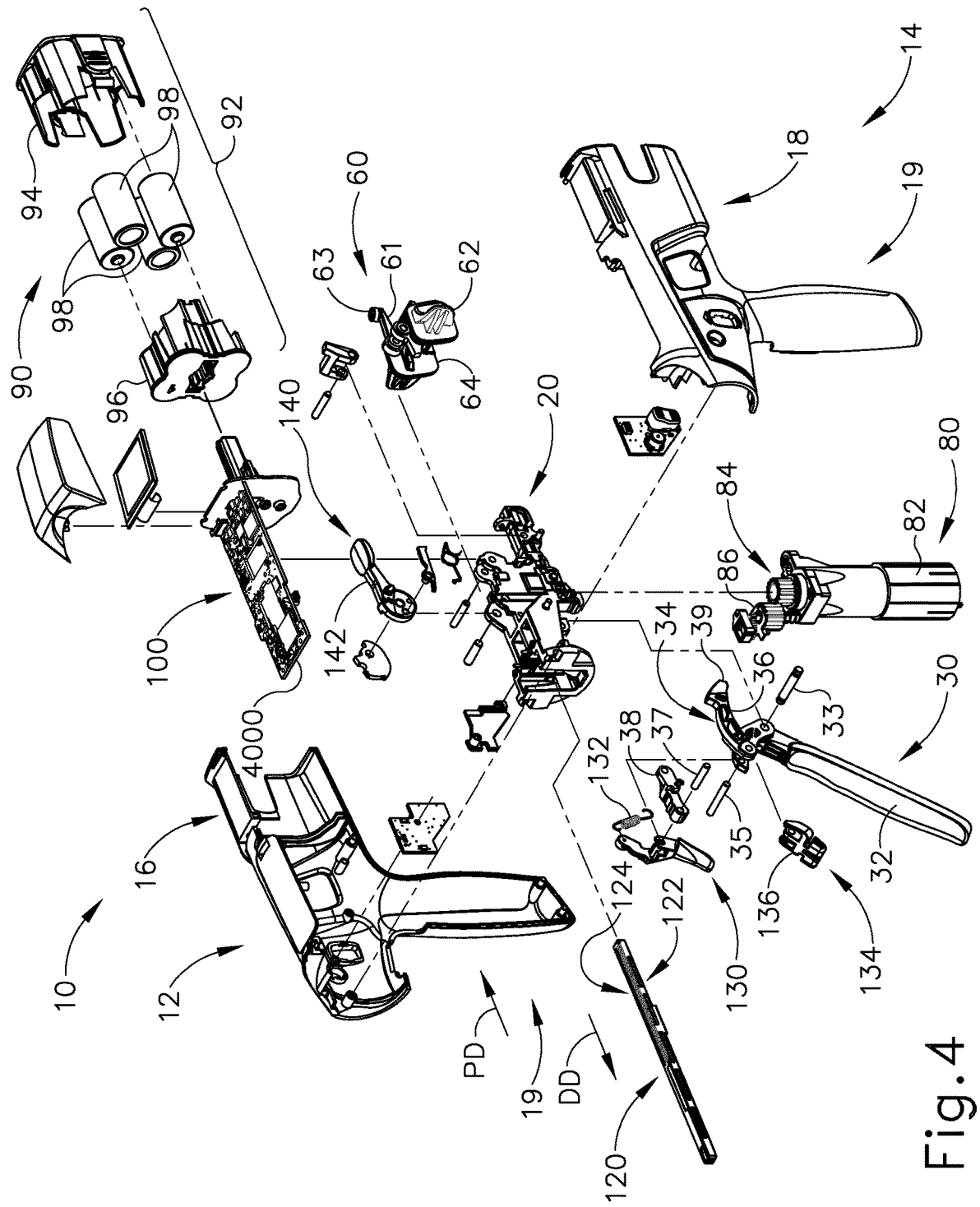
FIG. 4 depicts an exploded perspective view of certain portions of the handle assembly of the instrument of FIG. 1.

FIG. 1 illustrates the handle assembly (14) with an interchangeable shaft assembly (200) operably coupled thereto. FIGS. 2 and 3A illustrate attachment of the interchangeable shaft assembly (200) to the housing (12) of handle assembly (14). As can be seen in FIG. 4, the handle assembly (14) may comprise a pair of interconnectable handle housing segments (16, 18) that may be interconnected by screws, snap features, adhesive, etc. In the illustrated arrangement, the handle housing segments (16, 18) cooperate to form a pistol grip portion (19) that can be gripped and manipulated by the clinician. As will be discussed in further detail below, the handle assembly (14) operably supports a plurality of drive systems therein that are configured to generate and apply various control motions to corresponding portions of the interchangeable shaft assembly that is operably attached thereto.

The handle assembly (14) may further include a frame (20) that operably supports a plurality of drive systems. For example, the frame (20) can operably support a "first" or closure drive system, generally designated as (30), which may be employed to apply closing and opening motions to the interchangeable shaft assembly (200) that is operably attached or coupled thereto. In at least one example, the closure drive system (30) may include an actuator in the form of a closure trigger (32) that is pivotally supported by the frame (20). More specifically, as illustrated in FIG. 4, the closure trigger (32) is pivotally coupled to the housing (14) by a pin (33). Such arrangement enables the closure trigger (32) to be manipulated by a clinician such that when the clinician grips the pistol grip portion (19) of the handle assembly (14), the closure trigger (32) may be easily pivoted from a starting or "unactuated" position to an "actuated" position and more particularly to a fully compressed or fully actuated position. The closure trigger (32) may be biased into the unactuated position by spring or other biasing arrangement (not shown). In various examples, the closure drive system (30) further includes a closure linkage assembly (34) that is pivotally coupled to the closure trigger (32). The closure linkage assembly (34) may include a first closure link (36) and a second closure link (38) that are pivotally coupled to the closure trigger (32) by a pin (35). The second closure link (38) may also be referred to herein as an "attachment member" and include a transverse attachment pin (37).

Still referring to FIG. 4, it can be observed that the first closure link (36) may have a locking wall or end (39) thereon that is configured to cooperate with a closure release assembly (60) that is pivotally coupled to the frame (20). In at least one example, the closure release assembly (60) may comprise a release button assembly (62) that has a distally protruding locking pawl (64) formed thereon. The release button assembly (62) may be pivoted in a counterclockwise direction by a release spring (not shown). As the clinician depresses the closure trigger (32) from its unactuated position toward the pistol grip portion (19) of the handle assembly (14), the first closure link (36) pivots upwardly to a point wherein the locking pawl (64) drops into retaining engagement with the locking wall (39) on the first closure link (36) thereby preventing the closure trigger (32) from returning to the unactuated position. Thus, the closure release assembly (60) serves to lock the closure trigger (32) in the fully actuated position. These locking features may be released by actuation of release button assembly (62). Release button assembly (62) is configured and positioned to be actuated by the thumb of the operator hand that grasps pistol grip (19). In other words, the operator may grasp pistol grip (19) with one hand, actuate closure trigger (32) with one or more fingers of the same hand, and then actuate release button assembly (62) with the thumb of the same hand, without ever needing to release the grasp of pistol grip (19) with the same hand. When the clinician desires to unlock the closure trigger (32) to permit it to be resiliently driven back to the unactuated position, the clinician simply pivots the closure release button assembly (62) such that the locking pawl (64) is moved out of engagement with the locking wall (39) on the first closure link (36). When the locking pawl

(64) has been moved out of engagement with the first closure link (36), the closure trigger (32) may pivot back to the unactuated position. Other closure trigger locking and release arrangements may also be employed.

Further to the above, FIG. 1 illustrates the closure trigger (32) in its unactuated position which is associated with an open, or unclamped, configuration of the shaft assembly (200) in which tissue can be positioned between the jaws of the shaft assembly (200). It will be appreciated that the closure trigger (32) may be moved or actuated to an actuated position (not shown) which is associated with a closed, or clamped, configuration of the shaft assembly (200) in which tissue is clamped between the jaws of the shaft assembly (200). It will be further appreciated that when the closure trigger (32) is moved from its unactuated position to its actuated position, the closure release button (62) is pivoted between a first position and a second position. The rotation of the closure release button (62) can be referred to as being an upward rotation. However, at least a portion of the closure release button (62) is being rotated toward the circuit board (100).

Referring to FIG. 4, the closure release button (62) can include an arm (61) extending therefrom and a magnetic element (63), such as a permanent magnet, for example, mounted to the arm (61). When the closure release button (62) is rotated from its first position to its second position, the magnetic element (63) can move toward the circuit board (100). The circuit board (100) can include at least one sensor configured to detect the movement of the magnetic element (63). In at least one embodiment, a Hall Effect sensor (not shown), for example, can be mounted to the bottom surface of the circuit board (100). The Hall Effect sensor can be configured to detect changes in a magnetic field surrounding the Hall Effect sensor caused by the movement of the magnetic element (63). The Hall Effect sensor can be in signal communication with a microcontroller, for example, which can determine whether the closure release button (62) is in its first position, which is associated with the unactuated position of the closure trigger (32) and the open configuration of the end effector, its second position, which is associated with the actuated position of the closure trigger (32) and the closed configuration of the end effector, and/or any position between the first position and the second position.

In at least one example, the handle assembly (14) and the frame (20) may operably support another drive system referred to herein as a firing drive system (80) that is configured to apply firing motions to corresponding portions of the interchangeable shaft assembly attached thereto. The firing drive system may (80) also be referred to herein as a "second drive system". The firing drive system (80) may employ an electric motor (82), located in the pistol grip portion (19) of the handle assembly (14). In various forms the motor (82) may be a DC brushed driving motor having a maximum rotation of, approximately, 25,000 RPM, for example. In other arrangements, the motor may include a brushless motor, a cordless motor, a synchronous motor, a stepper motor, or any other suitable electric motor. The motor (82) may be powered by a power source (90) that in one example may comprise a removable power pack (92). For example, the power pack (92) may comprise a proximal housing portion (94) that is configured for attachment to a distal housing portion (96). The proximal housing portion (94) and the distal housing portion (96) are configured to operably support a plurality of batteries (98) therein. Batteries (98) may each comprise, for example, a Lithium Ion ("LI") or other suitable battery. The distal housing portion (96) is configured for removable operable attachment to a control circuit board assembly (100) that is also operably coupled to the motor (82). A number of batteries (98) may be connected in series may be used as the power source for the surgical instrument (10). In addition, the power source (90) may be replaceable and/or rechargeable. Various alternative forms that power source (90) may take will be described in greater detail below.

As outlined above with respect to other various examples, the electric motor (82) can include a rotatable shaft (not shown) that operably interfaces with a gear reducer assembly (84) that is mounted in meshing engagement with a with a set, or rack, of drive teeth (122) on a longitudinally-movable drive member (120). In use, a voltage polarity provided by the power source (90) can operate the electric motor (82) in a clockwise direction. The voltage polarity applied to the electric motor by the battery can be reversed in order to operate the electric motor (82) in a counterclockwise direction. When the electric motor (82) is rotated in one direction, the drive member (120) will be axially driven in the distal direction "DD". When the motor (82) is driven in the opposite rotary direction, the drive member (120) will be axially driven in a proximal direction "PD". The handle assembly (14) can include a switch that can be configured to reverse the polarity applied to the electric motor (82) by the power source (90). As with the other forms described herein, the handle assembly (14) can also include a sensor that is configured to detect the position of the drive member (120) and/or the direction in which the drive member (120) is being moved.

Actuation of the motor (82) can be controlled by a firing trigger (130) that is pivotally supported on the handle assembly (14). The firing trigger (130) may be pivoted between an unactuated position and an actuated position. The firing trigger (130) may be biased into the unactuated position by a spring (132) or other biasing arrangement such that when the clinician releases the firing trigger (130), it may be pivoted or otherwise returned to the unactuated position by the spring (132) or biasing arrangement. In at least one form the firing trigger (130) can be positioned "outboard" of the closure trigger (32) as was discussed above. In the present example, a firing trigger safety button (134) is pivotally mounted to the closure trigger (32) by pin (35). The safety button (134) is positioned between the firing trigger (130) and the closure trigger (32) and has a pivot arm (136) protruding therefrom. See FIG. 4. When the closure trigger (32) is in the unactuated position, the safety button (134) is contained in the handle assembly (14) where the clinician cannot readily access it and move it between a safety position preventing actuation of the firing trigger (130) and a firing position wherein the firing trigger (130) may be fired. As the clinician depresses the closure trigger (32), the safety button (134) and the firing trigger (130) pivot downwardly to a position where they can then be manipulated by the clinician.

As indicated above, in at least one form, the longitudinally movable drive member (120) has a rack of teeth (122) formed thereon for meshing engagement with a corresponding drive gear (86) of the gear reducer assembly (84). At least one form also includes a manually-actuatable "bailout" assembly (140) that is configured to enable the clinician to manually retract the longitudinally movable drive member (120) should the motor (82) become disabled. The bailout assembly (140) may include a lever or bailout handle assembly (142) that is configured to be manually pivoted into ratcheting engagement with a set of teeth (124) that are also provided in the drive member (120). Thus, the clinician can manually retract the drive member (120) by using the bailout handle assembly (142) to ratchet the drive member (120) in the proximal direction "PD". By way of example only, bailout assembly (140) may be constructed and operable in accordance with at least some of the teachings of U.S. Pub. No. 2010/0089970, entitled "Powered Surgical Cutting and Stapling Apparatus with Manually Retractable Firing System," published Apr. 15, 2010, now U.S. Pat. No. 8,608,045, issued Dec. 17, 2013, the disclosure of which is incorporated by reference herein.

In addition to or in lieu of the foregoing, handle assembly (14) and/or other features of instrument (10) may be constructed and operable in accordance with at least some of the teachings of U.S. patent application Ser. No. 14/226,142, entitled "Surgical Instrument Comprising a Sensor System," filed Mar. 26, 2014, now U.S. Pat. No. 9,913,642, issued Mar. 13, 2018, the disclosure of which is incorporated by reference herein.

B. Exemplary Shaft Assembly

Turning now to FIGS. 1 and 6-11, the interchangeable shaft assembly (200) includes a surgical end effector (300) that comprises a lower jaw (1050) that is configured to operably support a staple cartridge (1070) therein. The end effector (300) may further include an anvil (1060) that is pivotally supported relative to the lower jaw (1050). The interchangeable shaft assembly (200) may further include an articulation joint (270) and an articulation lock (350) (FIG. 5) that can be configured to releasably hold the end effector (300) in a desired position relative to a shaft axis SA-SA. By way of example only, end effector (300), articulation joint (270), and/or articulation lock (350) may be constructed and operable in accordance with at least some of the teachings of U.S. patent application Ser. No. 13/803,086, entitled "Articulatable Surgical Instrument Comprising an Articulation Lock," filed Mar. 14, 2013, published as U.S. Pub. No. 2014/0263541 on Sep. 18, 2014, now abandoned, the disclosure of which is incorporated by reference herein. As another merely illustrative example, articulation joint (270) and features that drive articulation joint may be constructed and operable in accordance with at least some of the teachings of U.S. Pub. No. 2014/0243801, entitled "Surgical Instrument End Effector Articulation Drive with Pinion and Opposing Racks," published Aug. 28, 2014, now U.S. Pat. No. 9,186,142, issued Nov. 17, 2015, the disclosure of which is incorporated by reference herein.

As can be seen in FIGS. 1-3 and 5, the interchangeable shaft assembly (200) can further include a proximal housing or nozzle (201) comprised of nozzle portions (202) and (203). The interchangeable shaft assembly (200) can further include a closure tube (260) that can be utilized to close and/or open the anvil (1060) of the end effector (300). Primarily referring now to FIG. 5, the shaft assembly (200) can include a spine (210) that can be configured to fixably support a shaft frame portion (212) of the articulation lock 350. The spine (210) can be configured to slidably support a firing member (220) therein; and also slidably support the closure tube (260) that extends around the spine (210). The spine (210) can also be configured to slidably support a proximal articulation driver (230). The articulation driver (230) has a distal end (231) that is configured to operably engage the articulation lock (350). The articulation lock (350) interfaces with an articulation frame (352) that is adapted to operably engage a drive pin (not shown) on the end effector frame (not shown). As indicated above, the articulation lock (350) and the articulation frame may be constructed and operable in accordance with at least some of the teachings of U.S. Patent Application Publication No. 2014/0263541, entitled "Articulatable Surgical Instrument Comprising an Articulation Lock," published Sep. 18, 2014, now abandoned, the disclosure of which is incorporated by reference herein. In various circumstances, the spine (210) can comprise a proximal end (211) that is rotatably supported in a chassis (240). In one arrangement, for example, the proximal end (211) of the spine (210) has a thread (214) formed thereon for threaded attachment to a spine bearing (not shown) configured to be supported within the chassis (240). Such an arrangement facilitates rotatable attachment of the spine (210) to the chassis (240) such that the spine (210) may be selectively rotated about a shaft axis SA-SA relative to the chassis (240).

Figure 5:
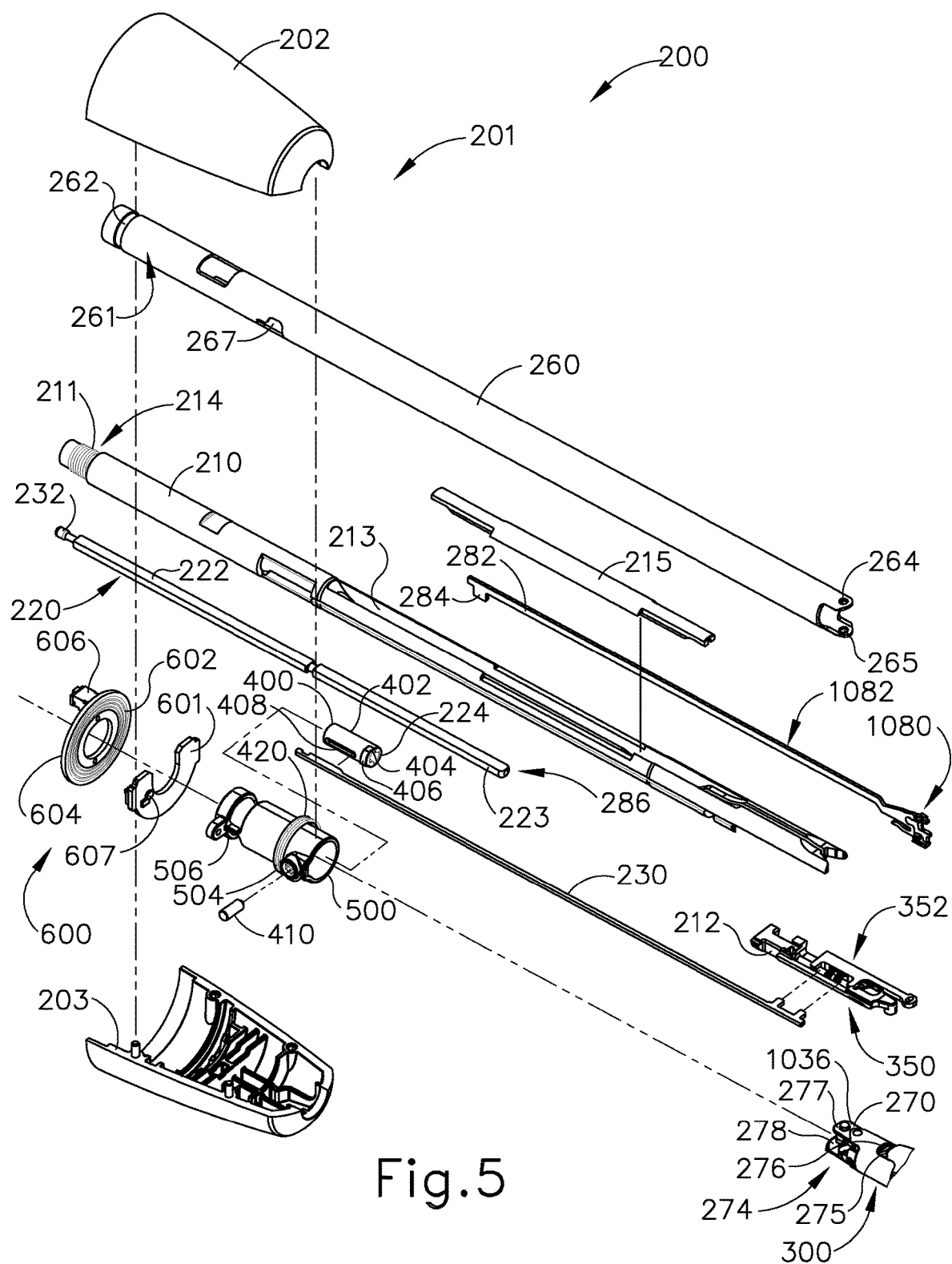
FIG. 5 depicts an exploded front perspective view of certain portions of the shaft assembly of FIG. 1.

Referring primarily to FIG. 3-5, the interchangeable shaft assembly (200) further includes a closure shuttle (250) that is slidably supported within the chassis (240) such that it may be axially moved relative thereto. As can be seen in FIG. 3, the closure shuttle (250) includes a pair of proximally-protruding hooks (252) that are configured for attachment to the attachment pin (37) that is attached to the second closure link (38) as will be discussed in further detail below. A proximal end (261) of the closure tube (260) is coupled to the closure shuttle (250) for relative rotation thereto. For example, a U shaped connector (not shown) is inserted into an annular slot (262) in the proximal end (261) of the closure tube (260) and is retained within vertical slots (not shown) in the closure shuttle (250). Such an arrangement serves to attach the closure tube (260) to the closure shuttle (250) for axial travel therewith while enabling the closure tube (260) to rotate relative to the closure shuttle (250) about the shaft axis SA-SA. A closure spring is journaled on the closure tube (260) and serves to bias the closure tube (260) in the proximal direction "PD," which can serve to pivot the closure trigger into the unactuated position when the shaft assembly is operably coupled to the handle assembly (14).

Figure 6:
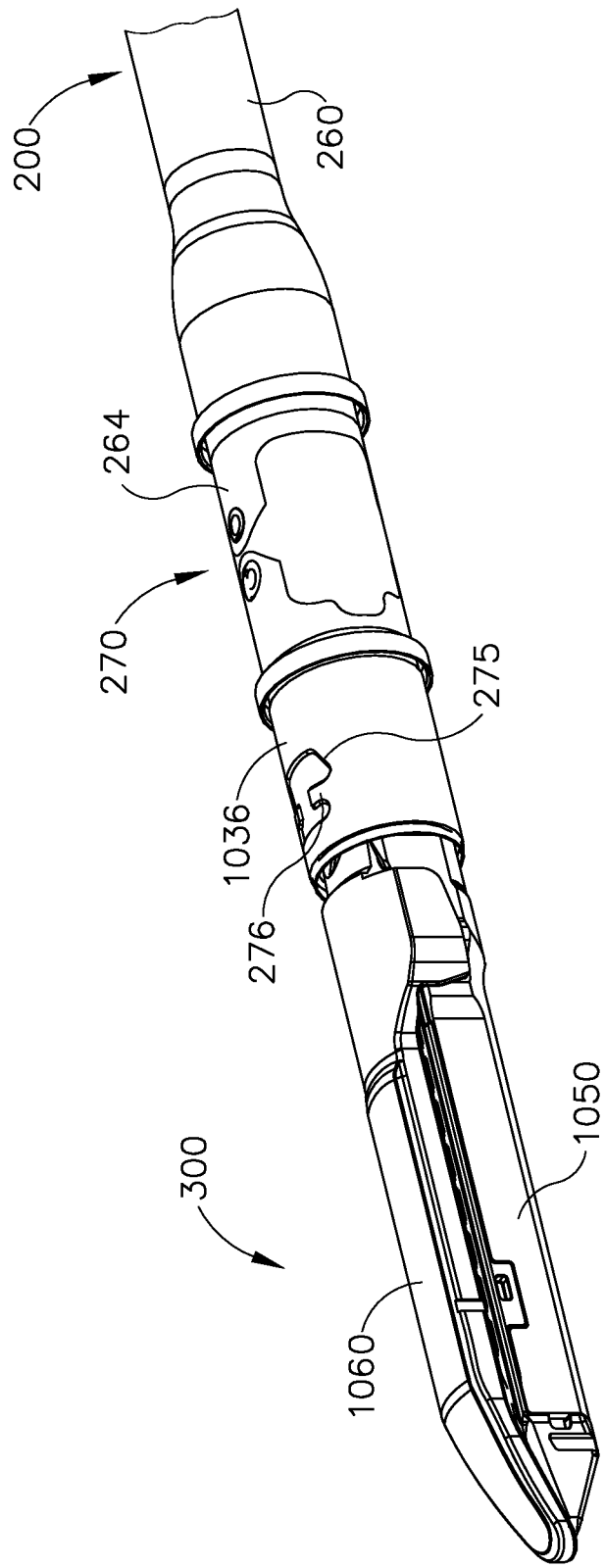
FIG. 6 depicts a perspective view of an end effector of the instrument of FIG. 1, with the end effector in a closed configuration.

As noted above, the interchangeable shaft assembly (200) may further include an articulation joint (270). Other interchangeable shaft assemblies, however, may not be capable of articulation. In the present example, articulation joint (270) enables longitudinal motion to be communicated from closure tube (260) to end effector (300) even when articulation joint (270) is in an articulated state. In particular, as shown in FIGS. 5-6, an end effector closure ring (1036) includes a horseshoe aperture (275) and a tab (276) for engaging an opening tab on the anvil (1060) in the various manners described in U.S. Patent Application Publication No. 2014/0263541, now abandoned, which has been incorporated by reference herein. As described in further detail therein, the horseshoe aperture (275) and tab (276) engage a tab on the anvil (1060) when the anvil (1060) is opened. An upper double pivot link (277) includes upwardly projecting distal and proximal pivot pins that engage respectively an upper distal pin hole in the upper proximally projecting tang (not shown) and an upper proximal pin hole in an upper distally projecting tang (264) on the closure tube (260). A lower double pivot link (278) includes upwardly projecting distal and proximal pivot pins that engage respectively a lower distal pin hole in the lower proximally projecting tang (274) and a lower proximal pin hole in the lower distally projecting tang (265).

In use, the closure tube (260) is translated distally to close the anvil (1060), for example, in response to the actuation of the closure trigger (32). The anvil (1060) is closed by distally translating the closure tube (260) and thus the shaft closure sleeve assembly (272), causing it to strike a proximal surface on the anvil (1060) in the manner described in the aforementioned reference U.S. Patent Application Publication No. 2014/0263541, now abandoned. As was also described in detail in that reference, the anvil (1060) is opened by proximally translating the closure tube (260) and the shaft closure sleeve assembly (272), causing tab (276) and the horseshoe aperture (275) to contact and push against the anvil tab to lift the anvil (1060). In the anvil-open position, the shaft closure tube (260) is moved to its proximal position. It should be understood that the configurations of tangs (264, 265) and links (277, 278) allow longitudinal motion to be communicated from closure tube (260) to closure ring (1036) regardless of whether articulation joint (270) is in a straight or articulated state.

As indicated above, the surgical instrument (10) may further include an articulation lock (350) (FIG. 5) of the types and construction described in further detail in U.S. Patent Application Publication No. 2014/0263541, now abandoned, which can be configured and operated to selectively lock the end effector (300) in a straight position or in any selected articulated position. Such arrangement enables the end effector (300) to be rotated, or articulated, relative to the shaft closure tube (260) when the articulation lock (350) is in its unlocked state. In such an unlocked state, the end effector (300) can be positioned and pushed against soft tissue and/or bone, for example, surrounding the surgical site within the patient in order to cause the end effector (300) to articulate relative to the closure tube (260). The end effector (300) may also be articulated relative to the closure tube (260) by an articulation driver (230) (FIG. 5).

Figure 10A:
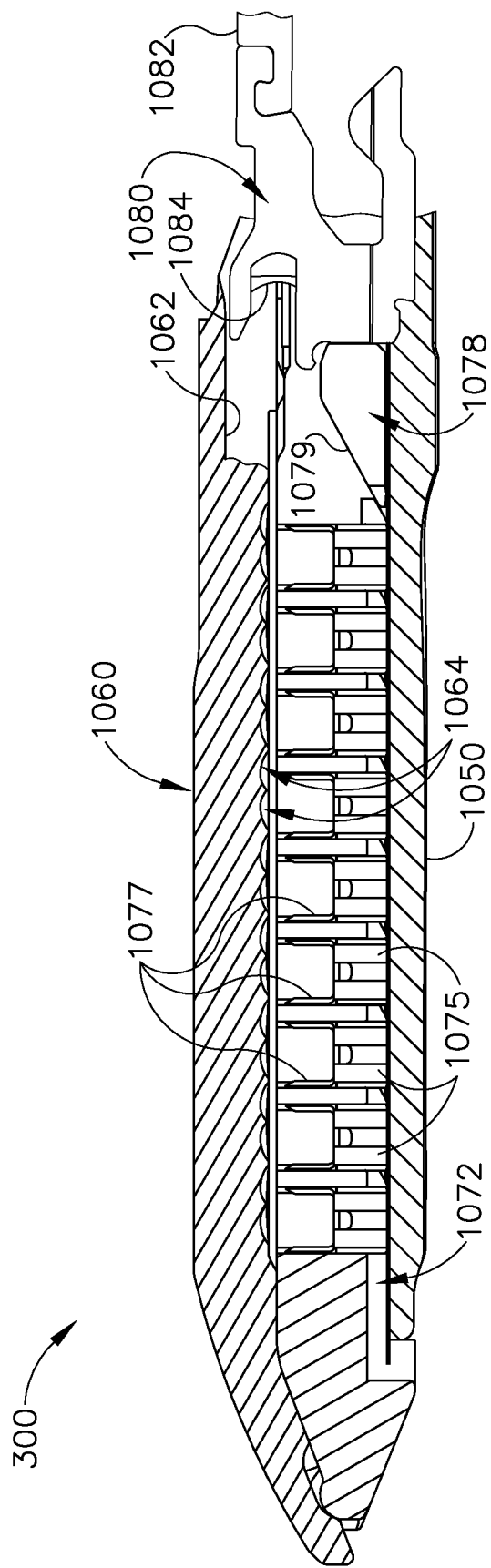
FIG. 10A depicts a cross-sectional side view of the end effector of FIG. 6, taken along line 10-10 of FIG. 7, with the firing beam in a proximal position.
Figure 10B:
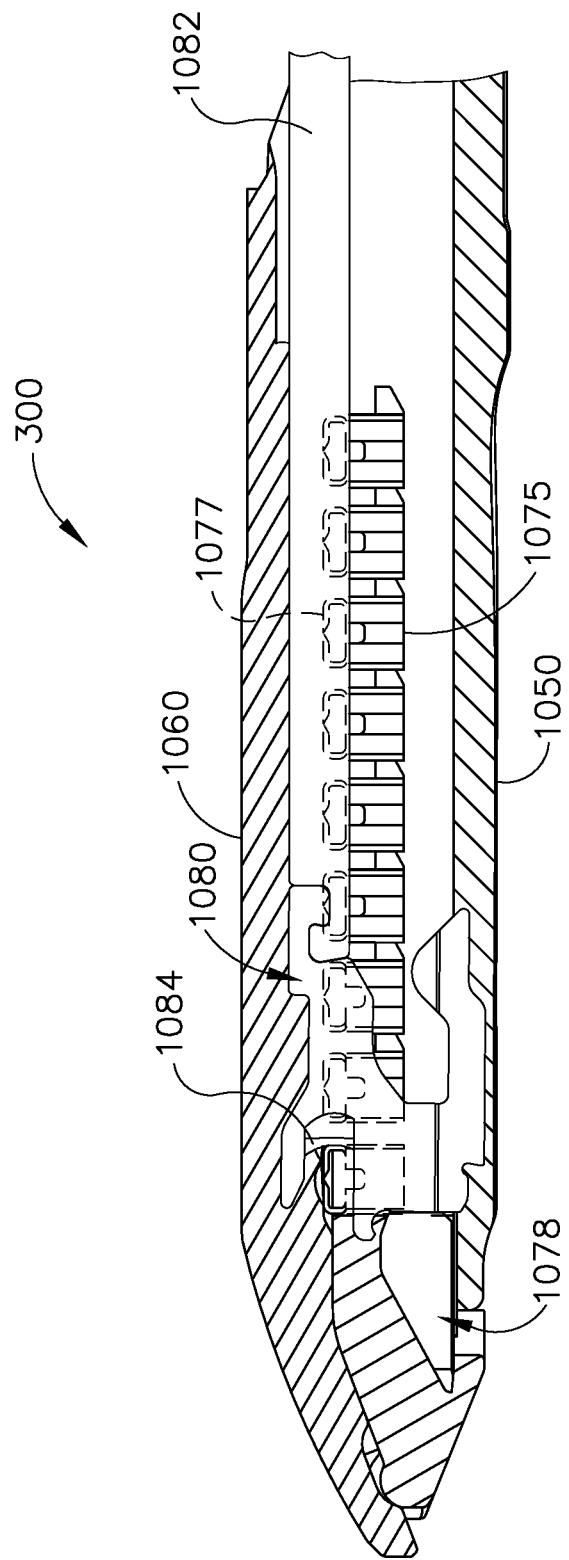
FIG. 10B depicts a cross-sectional side view of the end effector of FIG. 6, taken along line 10-10 of FIG. 7, with the firing beam in a distal position.

Still referring to FIG. 5, the interchangeable shaft assembly (200) further includes a firing member (220) that is supported for axial travel within the shaft spine (210). The firing member (220) includes an intermediate firing shaft portion (222) that is configured for attachment to a distal cutting portion or firing beam (1082). The firing member (220) may also be referred to herein as a "second shaft" and/or a "second shaft assembly". As can be seen in FIG. 5, the intermediate firing shaft portion (222) may include a longitudinal slot (223) in the distal end thereof that can be configured to receive a tab (284) on the proximal end (282) of the distal firing beam (1082). The longitudinal slot (223) and the proximal end (282) can be sized and configured to permit relative movement therebetween and can comprise a slip joint (286). The slip joint (286) can permit the intermediate firing shaft portion (222) of the firing drive (220) to be moved to articulate the end effector (300) without moving, or at least substantially moving, the firing beam (1082). Once the end effector (300) has been suitably oriented, the intermediate firing shaft portion (222) can be advanced distally until a proximal sidewall of the longitudinal slot (223) comes into contact with the tab (284) in order to advance the firing beam (1082) and fire the staple cartridge positioned within the lower jaw (1050) (FIGS. 10A-10B). As can be further seen in FIG. 5, the shaft spine (210) has an elongate opening or window (213) therein to facilitate assembly and insertion of the intermediate firing shaft portion (222) into the shaft frame (210). Once the intermediate firing shaft portion (222) has been inserted therein, a top frame segment (215) may be engaged with the shaft frame (212) to enclose the intermediate firing shaft portion (222) and firing beam (1082) therein. The firing member (220) may be further constructed and operable in accordance with at least some of the teachings of U.S. Patent Application Publication No. 2014/0263541, now abandoned.

Further to the above, the shaft assembly (200) can include a clutch assembly (400) that can be configured to selectively and releasably couple the articulation driver (230) to the firing member (220). In one form, the clutch assembly (400) includes a lock collar, or sleeve (402), positioned around the firing member (220). The lock sleeve (402) can be rotated between an engaged position, in which the lock sleeve (402) couples the articulation driver (360) to the firing member (220); and a disengaged position, in which the articulation driver (360) is not operably coupled to the firing member (200). When lock sleeve (402) is in its engaged position, distal movement of the firing member (220) can move the articulation driver (360) distally; and, correspondingly, proximal movement of the firing member (220) can move the articulation driver (230) proximally. When lock sleeve (402) is in its disengaged position, movement of the firing member (220) is not transmitted to the articulation driver (230); and, as a result, the firing member (220) can move independently of the articulation driver (230). In various circumstances, the articulation driver (230) can be held in position by the articulation lock (350) when the articulation driver (230) is not being moved in the proximal or distal directions by the firing member (220).

The lock sleeve (402) can comprise a cylindrical, or an at least substantially cylindrical, body including a longitudinal aperture (not shown) defined therein configured to receive the firing member (220). The lock sleeve (402) can comprise diametrically-opposed, inwardly-facing lock protrusions (404) and an outwardly-facing lock member (406). The lock protrusions (404) can be configured to be selectively engaged with the firing member (220). More particularly, when the lock sleeve (402) is in its engaged position, the lock protrusions (404) are positioned within a drive notch (224) defined in the firing member (220) such that a distal pushing force and/or a proximal pulling force can be transmitted from the firing member (220) to the lock sleeve (402). When the lock sleeve (402) is in its engaged position, the second lock member (406) is received within a drive notch (232) defined in the articulation driver (230) such that the distal pushing force and/or the proximal pulling force applied to the lock sleeve (402) can be transmitted to the articulation driver (230). In effect, the firing member (220), the lock sleeve (402), and the articulation driver (230) will move together when the lock sleeve (402) is in its engaged position. On the other hand, when the lock sleeve (402) is in its disengaged position, the lock protrusions (404) may not be positioned within the drive notch (224) of the firing member (220); and, as a result, a distal pushing force and/or a proximal pulling force may not be transmitted from the firing member (220) to the lock sleeve (402). Correspondingly, the distal pushing force and/or the proximal pulling force may not be transmitted to the articulation driver (230). In such circumstances, the firing member (220) can be slid proximally and/or distally relative to the lock sleeve (402) and the proximal articulation driver (230).

In one example, still referring to FIG. 5, the shaft assembly (200) further includes a switch drum (500) that is rotatably received on the closure tube (260). The switch drum (500) comprises a hollow shaft segment (not shown) that has a shaft boss (504) formed thereon for receive an outwardly protruding actuation pin (410) therein. In various circumstances, the actuation pin (410) extends through a slot (267) into a longitudinal slot (408) provided in the lock sleeve (402) to facilitate axial movement of the lock sleeve (402) when it is engaged with the articulation driver (230). A rotary torsion spring (420) is configured to engage the boss (504) on the switch drum (500) and a portion of the nozzle housing (203) to apply a biasing force to the switch drum (500). The switch drum (500) can further comprise at least partially circumferential openings (506) defined therein that can be configured to receive circumferential mounts (not shown) extending from the nozzle halves (202, 203) and permit relative rotation, but not translation, between the switch drum (500) and the proximal nozzle (201). The mounts (not shown) also extend through openings (not shown) in the closure tube (260) to be seated in recesses (211) in the shaft spine (210). However, rotation of the nozzle (201) to a point where the mounts reach the end of their respective slots (506) in the switch drum (500) will result in rotation of the switch drum (500) about the shaft axis SA-SA. Rotation of the switch drum (500) will ultimately result in the rotation of the actuation pin (410) and the lock sleeve (402) between its engaged and disengaged positions. Thus, in essence, the nozzle (201) may be employed to operably engage and disengage the articulation drive system with the firing drive system in the various manners described in further detail in U.S. Patent Application Publication No. 2014/0263541, now abandoned.

As also shown in FIG. 5, the shaft assembly (200) can comprise a slip ring assembly (600) that can be configured to conduct electrical power to and/or from the end effector (300) and/or communicate signals to and/or from the end effector (300), for example. The slip ring assembly (600) can comprise a proximal connector flange (604) mounted to a chassis flange (not shown) extending from the chassis (not shown) and a distal connector flange (601) positioned within a slot defined in the nozzle housings (202, 203). The proximal connector flange (604) can comprise a first face and the distal connector flange (601) can comprise a second face that is positioned adjacent to and movable relative to the first face. The distal connector flange (601) can rotate relative to the proximal connector flange (604) about the shaft axis SA-SA. The proximal connector flange (604) can comprise a plurality of concentric, or at least substantially concentric, conductors (602) defined in the first face thereof. A connector (607) can be mounted on the proximal side of the connector flange (601) and may have a plurality of contacts (not shown). Each contact of the connector flange (601) corresponds to and is in electrical contact with one of the conductors (602). Such an arrangement permits relative rotation between the proximal connector flange (604) and the distal connector flange (601) while maintaining electrical continuity therebetween. The proximal connector flange (604) can include an electrical connector (606) that can place the conductors (602) in signal communication with a shaft circuit board (not shown) that is mounted to the shaft chassis (240), for example. In at least one instance, a wiring harness comprising a plurality of conductors can extend between the electrical connector (606) and the shaft circuit board. The electrical connector (606) may extend proximally through a connector opening defined in the chassis mounting flange. U.S. Patent Application Publication No. 2014/0263552, entitled "Staple Cartridge Tissue Thickness Sensor System," published Sep. 18, 2014, now abandoned, and U.S. Patent Application Publication No. 2014/0263551, entitled "Staple Cartridge Tissue Thickness Sensor System," published Sep. 18, 2014, now U.S. Pat. No. 9,345,481, issued May 24, 2016 are incorporated herein by reference in their entireties. Further details regarding slip ring assembly (600) may be found in the aforementioned U.S. Patent Application Publication No. 2014/0263541, now abandoned.

As discussed above, the shaft assembly (200) can include a proximal portion that is fixably mounted to the handle assembly (14) and a distal portion that is rotatable about a longitudinal axis. The rotatable distal shaft portion can be rotated relative to the proximal portion about the slip ring assembly (600), as discussed above. The distal connector flange (601) of the slip ring assembly (600) can be positioned within the rotatable distal shaft portion. Moreover, further to the above, the switch drum (500) can also be positioned within the rotatable distal shaft portion. When the rotatable distal shaft portion is rotated, the distal connector flange (601) and the switch drum (500) can be rotated synchronously with one another. In addition, the switch drum (500) can be rotated between a first position and a second position relative to the distal connector flange (601). When the switch drum (500) is in its first position, the articulation drive system may be operably disengaged from the firing drive system and, thus, the operation of the firing drive system may not articulate the end effector (300) of the shaft assembly (200). When the switch drum (500) is in its second position, the articulation drive system may be operably engaged with the firing drive system and, thus, the operation of the firing drive system may articulate the end effector (300) of the shaft assembly (200). When the switch drum (500) is moved between its first position and its second position, the switch drum (500) is moved relative to distal connector flange (601). In various instances, the shaft assembly (200) can comprise at least one sensor configured to detect the position of the switch drum (500). For example, the distal connector flange (601) can comprise a Hall Effect sensor (not shown), for example, and the switch drum (500) can comprise a magnetic element, such as permanent magnet (not shown) for example. The Hall Effect sensor can be configured to detect the position of the permanent magnet. When the switch drum (500) is rotated between its first position and its second position, the permanent magnet can move relative to the Hall Effect sensor. In various instances, Hall Effect sensor can detect changes in a magnetic field created when the permanent magnet (505) is moved. The Hall Effect sensor can be in signal communication with the shaft circuit board and/or the handle circuit board (100), for example. Based on the signal from the Hall Effect sensor, a microcontroller on the shaft circuit board and/or the handle circuit board (100) can determine whether the articulation drive system is engaged with or disengaged from the firing drive system.

Figure 3B:
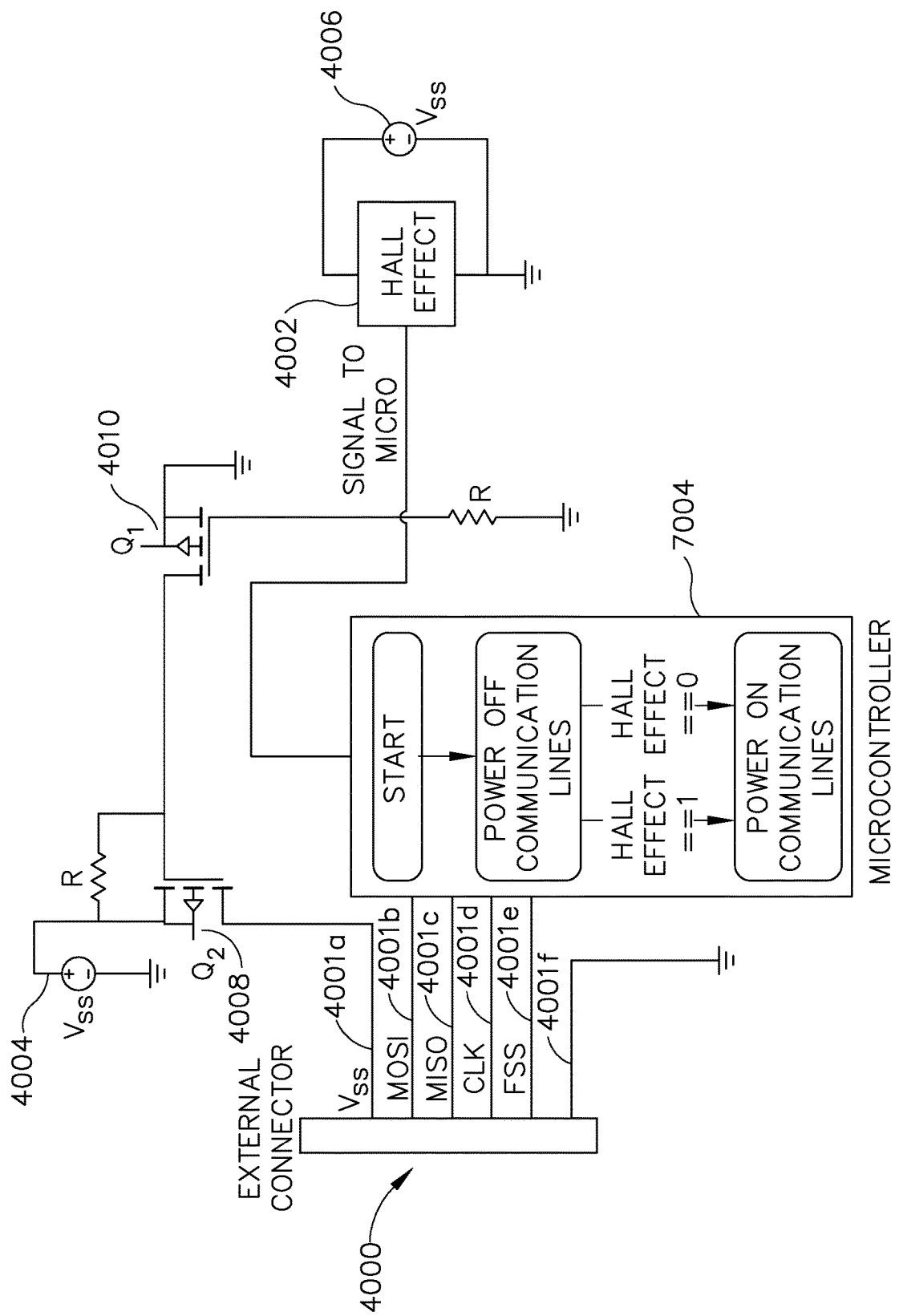
FIG. 3B depicts a schematic view of certain components of the instrument of FIG. 1.

Referring again to FIGS. 2 and 3A-B, the handle assembly (14) includes an electrical connector (4000) comprising a plurality of electrical contacts (4001a-f). In particular, the electrical connector (4000) of the present example comprises a first contact (4001a), a second contact (4001b), a third contact (4001c), a fourth contact (4001d), a fifth contact (4001e), and a sixth contact (4001f). Electrical contacts (4001a-f) are configured and arranged to contact complementary contacts (4011a-f) at the proximal end of shaft assembly (200) when shaft assembly (200) is coupled with handle assembly (14), such that contacts (4001a-f, 4011a-f) provide paths for electrical communication between handle assembly (14) and shaft assembly (200). Exemplary details of such electrical communication are described elsewhere herein. While the illustrated example utilizes six contacts, other embodiments are envisioned which may utilize more or less than six contacts. As illustrated in FIG. 3B, the first contact (4001a) is in electrical communication with a transistor (4008), contacts (4001b-e) each are in electrical communication with a microcontroller (7004), and the sixth contact (4001f) is in electrical communication with a ground. In certain circumstances, one or more of the electrical contacts (4001b-e) may be in electrical communication with one or more output channels of the microcontroller (7004) and can be energized, or have a voltage potential applied thereto, when the handle assembly (14) is in a powered state.

In addition or in the alternative, one or more of the electrical contacts (4001b-e) may be in electrical communication with one or more input channels of the microcontroller (7004) and, when the handle assembly (14) is in a powered state, the microcontroller (7004) can be configured to detect when a voltage potential is applied to such electrical contacts (4001b-e). When shaft assembly (200) is not coupled with the handle assembly (14), electrical contacts (4001a-f) may be exposed and may be prone to being accidentally placed in electrical communication with one another. Such circumstances may arise when one or more of the contacts (4001a-f) come into contact with an electrically conductive material. When this occurs, the microcontroller (7004) may receive an erroneous input and/or the shaft assembly (200) can receive an erroneous output, for example. To address this issue, in various circumstances, the handle assembly (14) may be configured to remain in a powered-down state when the handle assembly (14) is not coupled to a shaft assembly, such as shaft assembly (200). In such circumstances, the microcontroller (7004) may be configured to ignore inputs, or voltage potentials, applied to the contacts (4001a-f) in electrical communication with the microcontroller (7004) until shaft assembly (14) is attached to the handle assembly (14). Even though the microcontroller (7004) may be supplied with power to operate other functionalities of the handle assembly (14) in such circumstances, the handle assembly (14) may be in a powered-down state. In a way, the electrical connector (4000) may be in a powered-down state as voltage potentials applied to the electrical contacts (4001b-4001e) may not affect the operation of the handle assembly (14). It will be appreciated that electrical contacts (4001a) and (4001f), which are not in electrical communication with the microcontroller (7004) in the example shown, may or may not be in a powered-down state regardless of the state of the contacts (4001b-e). For instance, in one example, sixth contact (4001f) may remain in electrical communication with a ground regardless of whether the handle assembly (14) is in a powered-up or a powered-down state.

Furthermore, the transistor (4008), and/or any other suitable arrangement of transistors, such as transistor (4010), for example, and/or switches may be configured to control the supply of power from a power source (4004) (e.g., power pack (92)) to the first electrical contact (4001a), regardless of whether the handle assembly (14) is in a powered-up or a powered-down state. In various circumstances, the shaft assembly (200) can be configured to change the state of the transistor (4008) when the shaft assembly (200) is engaged with the handle assembly (14). In certain circumstances, further to the below, a Hall Effect sensor (4002) can be configured to switch the state of transistor (4010) which, as a result, can switch the state of transistor (4008) and ultimately supply power from power source (4004) to first contact (4001a). In this way, both the power circuits and the signal circuits to the connector (4000) can be powered down when shaft assembly (200) is not coupled to the handle assembly (14), and powered up when shaft assembly (200) is installed to the handle 14.

In various examples, referring again to FIG. 3B, the handle assembly (14) includes the Hall Effect sensor (4002), which can be configured to detect a detectable element, such as a magnetic element (4007) (FIG. 3) on shaft assembly (200) when the shaft assembly (200) is coupled to the handle assembly (14). The Hall Effect sensor (4002) is in communication with a power source (4006) (e.g., power pack (92)), which is configured to amplify the detection signal of the Hall Effect sensor (4002) and communicate with an input channel of the microcontroller (7004) via the circuit illustrated in FIG. 3B. Once the microcontroller (7004) has a received an input indicating that shaft assembly (200) has been at least partially coupled to the handle (14) such that electrical contacts (4001a-f) are no longer exposed, the microcontroller (7004) can enter into its normal, or powered-up, operating state. In such an operating state, the microcontroller (7004) will evaluate the signals transmitted to one or more of the contacts (4001b-e) from the shaft assembly and/or transmit signals to the shaft assembly (200) through one or more of the contacts (4001b-e) in normal use thereof. In various circumstances, the shaft assembly (200) may have to be fully seated before the Hall Effect sensor (4002) can detect the magnetic element (4007). While a Hall Effect sensor (4002) is utilized to detect the presence of the shaft assembly (200) in the present example, it should be understood that any other suitable system of sensors and/or switches can be utilized to detect whether shaft assembly (200) has been coupled to the handle assembly (14), such as those described below. In addition to or in lieu of the foregoing, shaft assembly (200) and/or other features of instrument (10) may be constructed and operable in accordance with at least some of the teachings of U.S. patent application Ser. No. 14/226,142, entitled "Surgical Instrument Comprising a Sensor System," filed Mar. 26, 2014, now U.S. Pat. No. 9,913,642, issued Mar. 13, 2018, the disclosure of which is incorporated by reference herein.

C. Exemplary End Effector

As shown in FIGS. 6-11, end effector (300) of the present example includes a lower jaw (1050) and a pivotable anvil (1060). Anvil (1060) includes a pair of integral, outwardly extending pins (1066) that are disposed in corresponding curved slots (1054) of lower jaw (1050). Anvil (1060) is pivotable toward and away from lower jaw (1050) between an open position (shown in FIG. 7) and a closed position (shown in FIGS. 6, 10A-10B). Use of the term "pivotable" (and similar terms with "pivot" as a base) should not be read as necessarily requiring pivotal movement about a fixed axis. For instance, in the present example, anvil (1060) pivots about an axis that is defined by pins (1066), which slide along curved slots (1054) of lower jaw (1050) as anvil (1060) moves toward lower jaw (1050). In such versions, the pivot axis translates along the path defined by slots (1054) while anvil (1060) simultaneously pivots about that axis. In addition or in the alternative, the pivot axis may slide along slots (1054) first, with anvil (1060) then pivoting about the pivot axis after the pivot axis has slid a certain distance along the slots (1054). It should be understood that such sliding/translating pivotal movement is encompassed within terms such as "pivot," "pivots," "pivotal," "pivotable," "pivoting," and the like. Of course, some versions may provide pivotal movement of anvil (1060) about an axis that remains fixed and does not translate within a slot or channel, etc.

Figure 8:
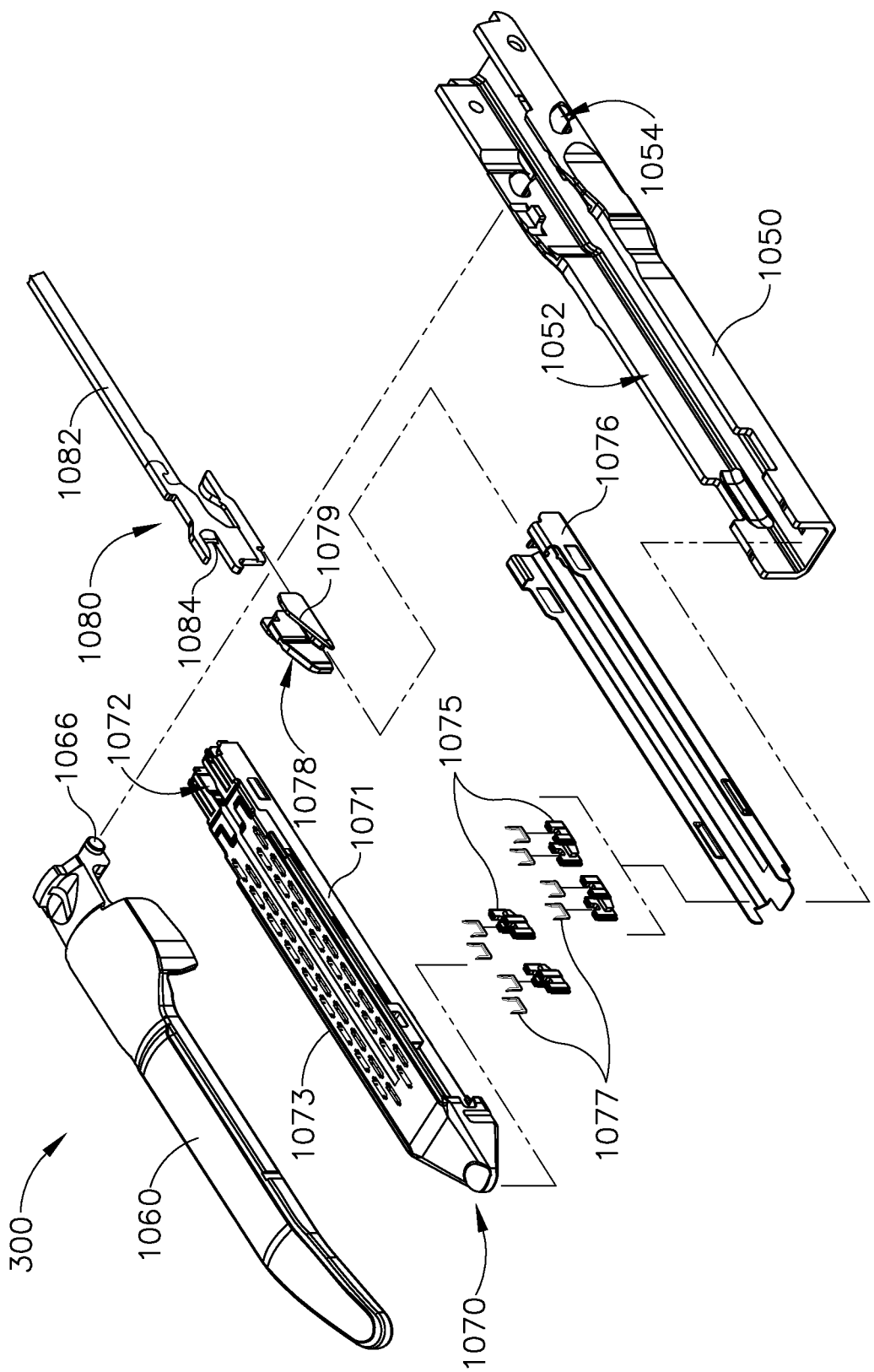
FIG. 8 depicts an exploded perspective view of the end effector of FIG. 6.

As best seen in FIG. 8, lower jaw (1050) of the present example defines a channel (1052) that is configured to receive a staple cartridge (1070). Staple cartridge (1070) may be inserted into channel (1052), end effector (300) may be actuated, and then staple cartridge (1070) may be removed and replaced with another staple cartridge (1070). Lower jaw (1050) thus releasably retains staple cartridge (1070) in alignment with anvil (1060) for actuation of end effector (300). In some versions, lower jaw (1050) is constructed in accordance with at least some of the teachings of U.S. Patent Application Publication No. 2014/0239044, entitled "Installation Features for Surgical Instrument End Effector Cartridge," published Aug. 28, 2014, now U.S. Pat.

No. 9,808,248, issued Nov. 7, 2017, the disclosure of which is incorporated by reference herein. Other suitable forms that lower jaw (1050) may take will be apparent to those of ordinary skill in the art in view of the teachings herein.

Figure 7:
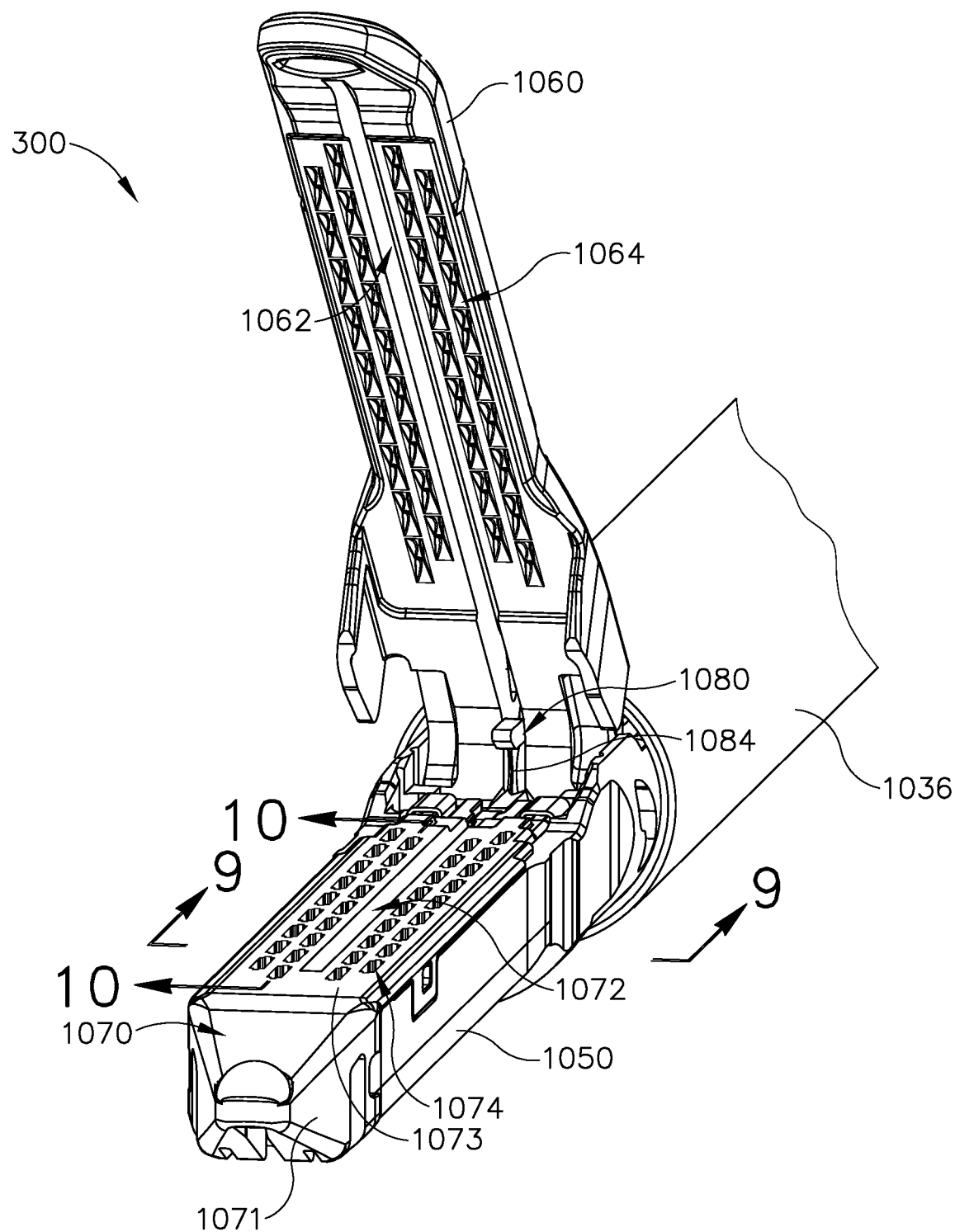
FIG. 7 depicts a perspective view of the end effector of FIG. 6, with the end effector in an open configuration.
Figure 9:
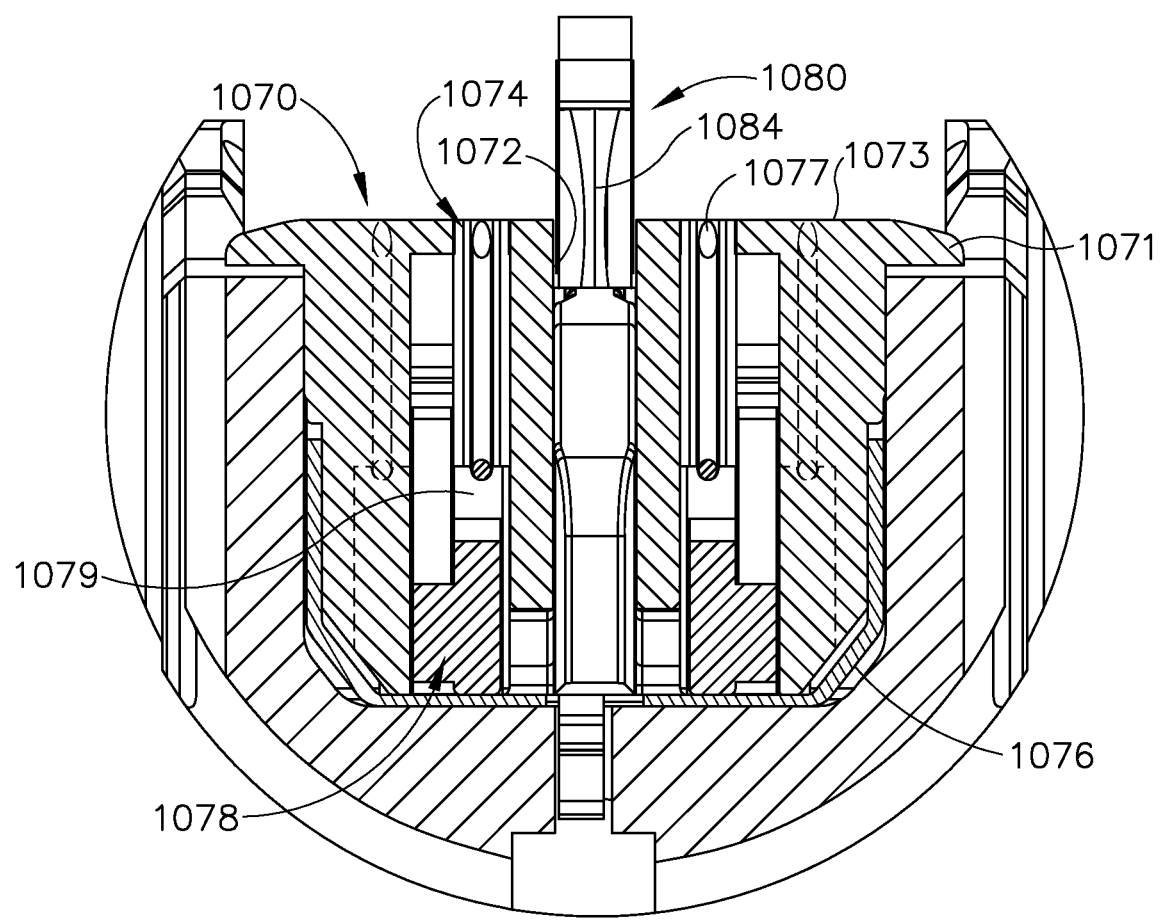
FIG. 9 depicts a cross-sectional end view of the end effector of FIG. 6, taken along line 9-9 of FIG. 7.

As best seen in FIGS. 7-9, staple cartridge (1070) of the present example comprises a cartridge body (1071) and a tray (1076) secured to the underside of cartridge body (1071). The upper side of cartridge body (1071) presents a deck (1073), against which tissue may be compressed when anvil (1060) is driven to a closed position by distal advancement of closure tube (260) and closure ring (1036). Cartridge body (1071) further defines a longitudinally extending channel (1072) and a plurality of staple pockets (1074). A staple (1077) is positioned in each staple pocket (1074). A staple driver (1075) is also positioned in each staple pocket (1074), underneath a corresponding staple (1077), and above tray (1076). As will be described in greater detail below, staple drivers (1075) are operable to translate upwardly in staple pockets (1074) to thereby drive staples (1077) upwardly through staple pockets (1074) and into engagement with anvil (1060). Staple drivers (1075) are driven upwardly by a wedge sled (1078), which is captured between cartridge body (1071) and tray (1076), and which translates longitudinally through cartridge body (1071) in response to distal advancement of knife member (1080). Wedge sled (1078) includes a pair of obliquely angled cam surfaces (1079), which are configured to engage staple drivers (1075) and thereby drive staple drivers (1075) upwardly as wedge sled (1078) translates longitudinally through cartridge (1070). For instance, when wedge sled (1078) is in a proximal position as shown in FIG. 10A, staple drivers (1075) are in downward positions and staples (1077) are located in staple pockets (1074). As wedge sled (1078) is driven to the distal position shown in FIG. 10B by distally translating knife member (1080), wedge sled (1078) drives staple drivers (1075) upwardly, thereby driving staples (1077) out of staple pockets (1074) and into staple forming pockets (1064). Thus, staple drivers (1075) translate along a vertical dimension as wedge sled (1078) translates along a horizontal dimension.

It should be understood that the configuration of staple cartridge (1070) may be varied in numerous ways. For instance, staple cartridge (1070) of the present example includes two longitudinally extending rows of staple pockets (1074) on one side of channel (1072); and another set of two longitudinally extending rows of staple pockets (1074) on the other side of channel (1072). However, in some other versions, staple cartridge (1070) includes three, one, or some other number of staple pockets (1074) on each side of channel (1072). In some versions, staple cartridge (1070) is constructed and operable in accordance with at least some of the teachings of U.S. Patent Application Publication No. 2014/0239042, entitled "Integrated Tissue Positioning and Jaw Alignment Features for Surgical Stapler," published Aug. 28, 2014, now U.S. Pat. No. 9,517,065, issued Dec. 13, 2016, the disclosure of which is incorporated by reference herein. In addition or in the alternative, staple cartridge (1070) may be constructed and operable in accordance with at least some of the teachings of U.S. Patent Application Publication No. 2014/0239044, entitled "Installation Features for Surgical Instrument End Effector Cartridge," published Aug. 28, 2014, now U.S. Pat. No. 9,808,248, issued Nov. 7, 2017, the disclosure of which is incorporated by reference herein. Other suitable forms that staple cartridge (1070) may take will be apparent to those of ordinary skill in the art in view of the teachings herein.

As best seen in FIG. 7, anvil (1060) of the present example comprises a longitudinally extending channel (1062) and a plurality of staple forming pockets (1064). Channel (1062) is configured to align with channel (1072) of staple cartridge (1070) when anvil (1060) is in a closed position. Each staple forming pocket (64) is positioned to lie over a corresponding staple pocket (1074) of staple cartridge (1070) when anvil (1060) is in a closed position. Staple forming pockets (1064) are configured to deform the legs of staples (1077) when staples (1077) are driven through tissue and into anvil (1060). In particular, staple forming pockets (1064) are configured to bend the legs of staples (1077) to secure the formed staples (1077) in the tissue. Anvil (1060) may be constructed in accordance with at least some of the teachings of U.S. Patent Application Publication No. 2014/0239042, entitled "Integrated Tissue Positioning and Jaw Alignment Features for Surgical Stapler," published Aug. 28, 2014, now U.S. Pat. No. 9,517,065, issued Dec. 13, 2016; at least some of the teachings of U.S. Patent Application Publication No. 2014/0239036, entitled "Jaw Closure Feature for End Effector of Surgical Instrument," published Aug. 28, 2014, now U.S. Pat. No. 9,839,421, issued Dec. 12, 2017; and/or at least some of the teachings of U.S. Patent Application Publication No. 2014/0239037, entitled "Staple Forming Features for Surgical Stapling Instrument," published Aug. 28, 2014, issued as U.S. Pat. No. 10,092,292 on Oct. 9, 2018, the disclosure of which is incorporated by reference herein. Other suitable forms that anvil (1060) may take will be apparent to those of ordinary skill in the art in view of the teachings herein.

In the present example, knife member (1080) is configured to translate through end effector (300). As best seen in FIGS. 8 and 10A-10B, knife member (1080) is secured to the distal end of a firing beam (1082), which extends through a portion of shaft assembly (200). As best seen in FIGS. 7 and 9, knife member (1080) is positioned in channels (1062, 1072) of anvil (1060) and staple cartridge (1070). Knife member (1080) includes a distally presented cutting edge (1084) that is configured to sever tissue that is compressed between anvil (1060) and deck (1073) of staple cartridge (1070) as knife member (1080) translates distally through end effector (300). As noted above and as shown in FIGS. 10A-10B, knife member (1080) also drives wedge sled (1078) distally as knife member (1080) translates distally through end effector (300), thereby driving staples (1077) through tissue and against anvil (1060) into formation. In some versions, end effector (300) includes lockout features that are configured to prevent knife member (1080) from advancing distally through end effector (300) when a staple cartridge (1070) is not inserted in lower jaw (1050). In addition or in the alternative, end effector (300) may include lockout features that are configured to prevent knife member (1080) from advancing distally through end effector (300) when a staple cartridge (1070) that has already been actuated once (e.g., with all staples (1077) deployed therefrom) is inserted in lower jaw (1050). By way of example only, such lockout features may be configured in accordance with at least some of the teachings of U.S. Patent Application Publication No. 2014/0239041, entitled "Lockout Feature for Movable Cutting Member of Surgical Instrument," published Aug. 28, 2014, now U.S. Pat. No. 9,717,497, issued Aug. 1, 2017, the disclosure of which is incorporated by reference herein; and/or at least some of the teachings of U.S. patent application Ser. No. 14/314,108, entitled "Method of Using Lockout Features for Surgical Stapler Cartridge," filed on Jun. 25, 2014, published as U.S. Pub. No. 2015/0374373 on Dec. 31, 2015, issued as U.S. Pat. No.

10,335,147 on Jul. 2, 2019, the disclosure of which is incorporated by reference herein. Other suitable forms that lockout features may take will be apparent to those of ordinary skill in the art in view of the teachings herein. Alternatively, end effector (300) may simply omit such lockout features.

In the present example, anvil (1060) is driven toward lower jaw (1050) by advancing closure ring (1036) distally relative to end effector (300). Closure ring (1036) cooperates with anvil (1060) through a camming action to drive anvil (1060) toward lower jaw (1050) in response to distal translation of closure ring (1036) relative to end effector (300). Similarly, closure ring (1036) may cooperate with anvil (1060) to open anvil (1060) away from lower jaw (1050) in response to proximal translation of closure ring (1036) relative to end effector (300). By way of example only, closure ring (1036) and anvil (1060) may interact in accordance with at least some of the teachings of U.S. Patent Application Publication No. 2014/0239036, entitled "Jaw Closure Feature for End Effector of Surgical Instrument," published Aug. 28, 2014, now U.S. Pat. No. 9,839,421, issued Dec. 12, 2017, the disclosure of which is incorporated by reference herein; and/or in accordance with at least some of the teachings of U.S. patent application Ser. No. 14/314,164 entitled "Jaw Opening Feature for Surgical Stapler," filed on Jun. 25, 2014, published as U.S. Pub. No. 2015/0374361 on Dec. 31, 2015, issued as U.S. Pat. No. 10,456,132 on Oct. 29, 2019, the disclosure of which is incorporated by reference herein. As noted above, handle assembly (14) includes a pistol grip (19) and a closure trigger (32). As also noted above, anvil (1060) is closed toward lower jaw (1050) in response to distal advancement of closure ring (1036). In the present example, closure trigger (32) is pivotable toward pistol grip (19) to drive closure tube (260) and closure ring (1036) distally. Various suitable components that may be used to convert pivotal movement of closure trigger (32) toward pistol grip (19) into distal translation of closure tube (260) and closure ring (1036) relative to handle assembly (14) are described in detail above. Similarly, other suitable features that may be used to actuate anvil (1060) will be apparent to those of ordinary skill in the art in view of the teachings herein.

Figure 11:
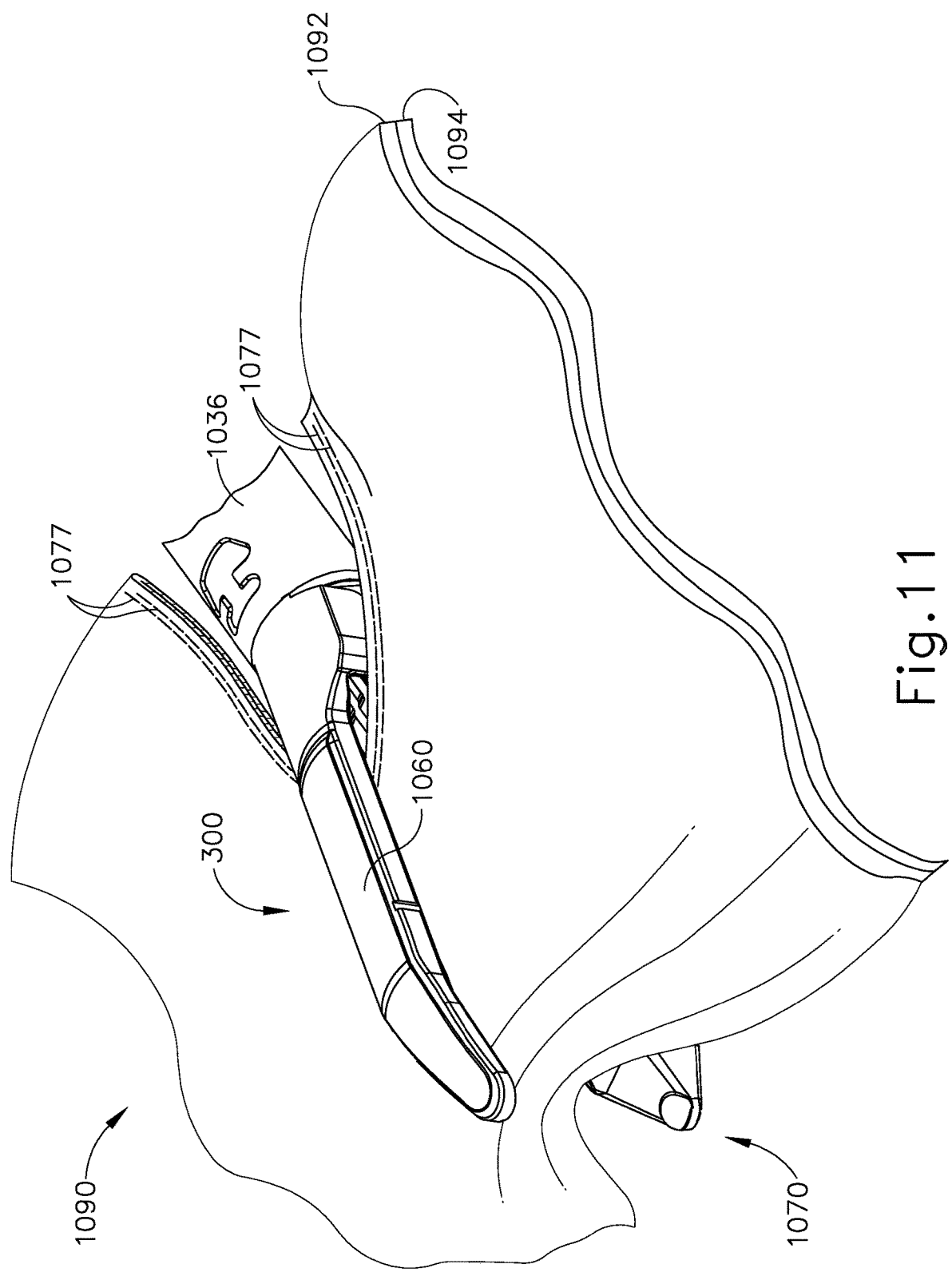
FIG. 11 depicts a perspective view of the end effector of FIG. 6, positioned at tissue and having been actuated once in the tissue.

FIG. 11 shows end effector (300) having been actuated through a single stroke through tissue (1090). As shown, cutting edge (1084) (obscured in FIG. 11) has cut through tissue (1090), while staple drivers (1075) have driven two alternating rows of staples (1077) through the tissue (1090) on each side of the cut line produced by cutting edge (1084). Staples (1077) are all oriented substantially parallel to the cut line in this example, though it should be understood that staples (1077) may be positioned at any suitable orientations. In the present example, end effector (300) is withdrawn from the trocar after the first stroke is complete, the spent staple cartridge (1070) is replaced with a new staple cartridge (1070), and end effector (300) is then again inserted through the trocar to reach the stapling site for further cutting and stapling. This process may be repeated until the desired amount of cuts and staples (1077) have been provided. Anvil (1060) may need to be closed to facilitate insertion and withdrawal through the trocar; and anvil (1060) may need to be opened to facilitate replacement of staple cartridge (1070).

It should be understood that cutting edge (1084) may sever tissue substantially contemporaneously with staples (1077) being driven through tissue during each actuation stroke. In the present example, cutting edge (1084) just slightly lags behind driving of staples (1077), such that a staple (1077) is driven through the tissue just before cutting edge (1084) passes through the same region of tissue, though it should be understood that this order may be reversed or that cutting edge (1084) may be directly synchronized with adjacent staples. While FIG. 11 shows end effector (300) being actuated in two layers (1092, 1094) of tissue (1090), it should be understood that end effector (300) may be actuated through a single layer of tissue (1090) or more than two layers (1092, 1094) of tissue. It should also be understood that the formation and positioning of staples (1077) adjacent to the cut line produced by cutting edge (1084) may substantially seal the tissue at the cut line, thereby reducing or preventing bleeding and/or leaking of other bodily fluids at the cut line. Furthermore, while FIG. 11 shows end effector (300) being actuated in two substantially flat, apposed planar layers (1092, 1094) of tissue, it should be understood that end effector (300) may also be actuated across a tubular structure such as a blood vessel, a section of the gastrointestinal tract, etc. FIG. 11 should therefore not be viewed as demonstrating any limitation on the contemplated uses for end effector (300). Various suitable settings and procedures in which instrument (10) may be used will be apparent to those of ordinary skill in the art in view of the teachings herein.

It should also be understood that any other components or features of instrument (10) may be configured and operable in accordance with any of the various references cited herein. Additional exemplary modifications that may be provided for instrument (10) will be described in greater detail below. Various suitable ways in which the below teachings may be incorporated into instrument (10) will be apparent to those of ordinary skill in the art. Similarly, various suitable ways in which the below teachings may be combined with various teachings of the references cited herein will be apparent to those of ordinary skill in the art. It should also be understood that the below teachings are not limited to instrument (10) or devices taught in the references cited herein. The below teachings may be readily applied to various other kinds of instruments, including instruments that would not be classified as surgical staplers. Various other suitable devices and settings in which the below teachings may be applied will be apparent to those of ordinary skill in the art in view of the teachings herein.

II. Exemplary Electrical Circuits and Components for Surgical Instrument

A. Exemplary Control Circuit and Components

Figures 1, 12:
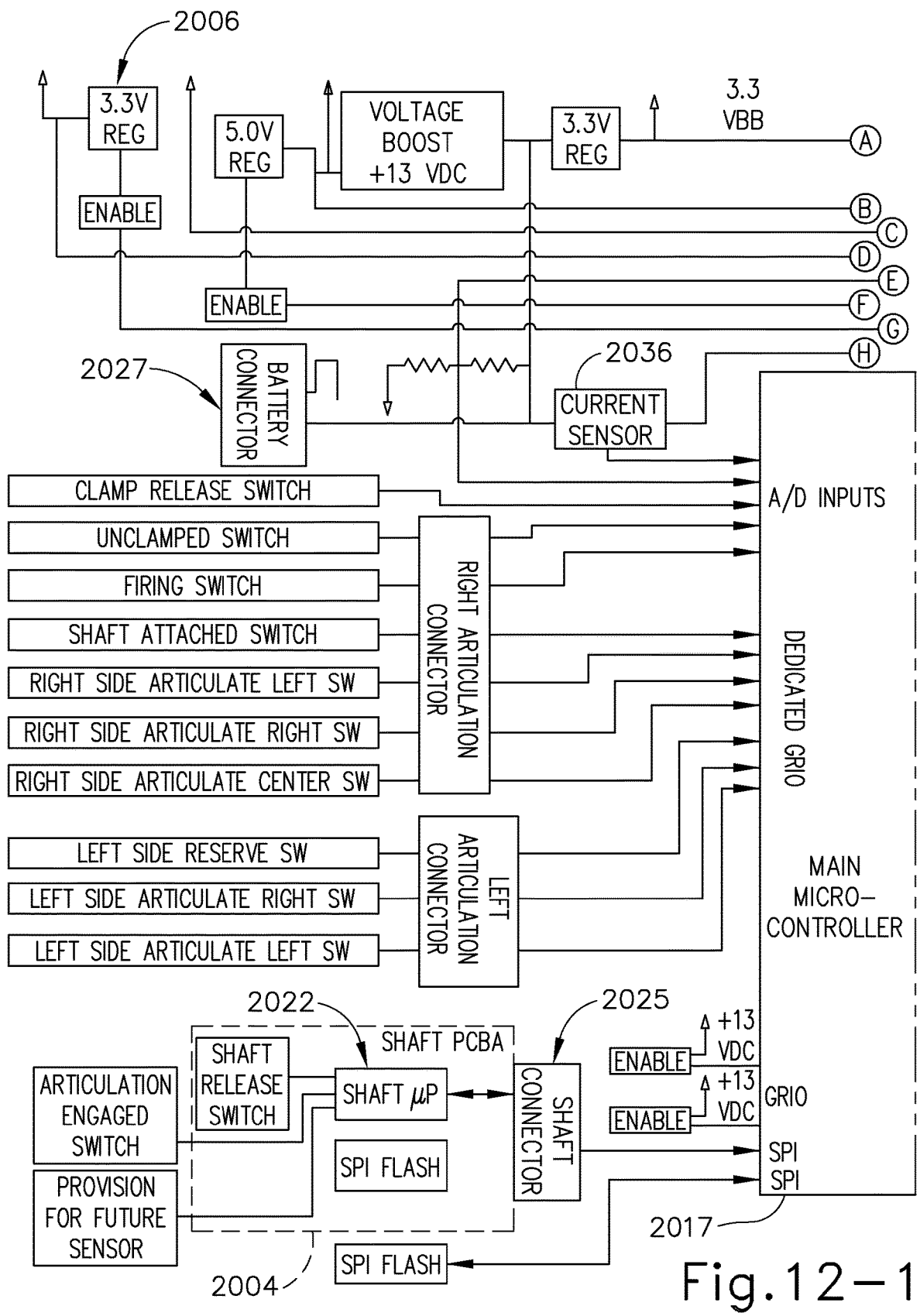
Figures 2, 12:
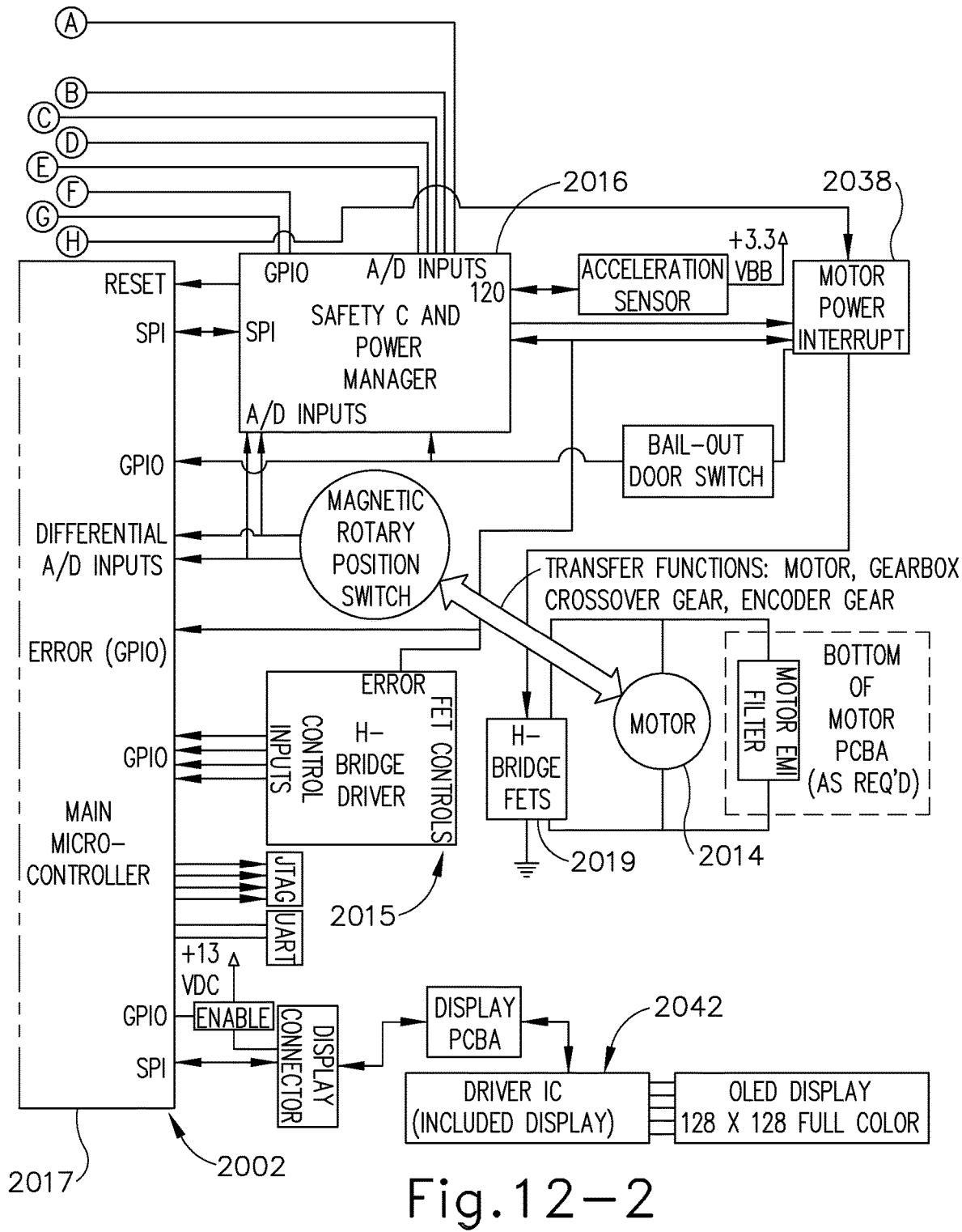

FIGS. 12-1 and 12-2 show an exemplary electrical circuit and component arrangement that may be incorporated into a surgical instrument, such as instrument (10). By way of example only, at least a portion of the circuit shown in FIGS. 12-1 and 12-2 may be incorporated into circuit board (100) described above. As shown, the handle assembly (2002), which may be configured in accordance with handle assembly (200) for example, includes a motor (2014) that can be controlled by a motor driver (2015). Motor (2014) is configured to be employed by the firing system of the surgical instrument (2000), such as the firing system described herein with respect to instrument (10). Motor (2014) may be further configured and/or operable similar or identical to motor (82) described above. In certain circumstances, the motor driver (2015) may comprise an H-Bridge FETs (2019), as illustrated in FIG. 12-2. The motor (2014) can be powered by a power assembly (2006) (FIG. 13), which can be releasably mounted to the handle assembly (2002), power assembly (2006) being configured to supply control power to the surgical instrument (2000). The power assembly (2006) may comprise a battery (2007) (FIG. 13) that may include a number of battery cells connected in series that can be used as the power source to power the surgical instrument (2000). In such a configuration, the power assembly (2006) may be referred to as a battery pack. Power assembly (2006) may be configured in accordance with power source (90) described herein. In certain circumstances, the battery cells of the power assembly (2006) may be replaceable and/or rechargeable. In at least one example, the battery cells can be Lithium-Ion batteries that can be removably coupled to the power assembly (2006).

Examples of drive systems and closure systems that are suitable for use with the surgical instrument (2000) are disclosed in U.S. Provisional Patent Application Ser. No. 61/782,866, entitled "Control System of a Surgical Instrument," and filed Mar. 14, 2013, the entire disclosure of which is incorporated by reference herein in its entirety. For example, as with motor (82) described above, the electric motor (2014) of this example can include a rotatable shaft (not shown) that may operably interface with a gear reducer assembly that can be mounted in meshing engagement with a set, or rack, of drive teeth on a longitudinally-movable drive member. In use, a voltage polarity provided by the battery (2007) (FIG. 13) can operate the electric motor (2014) to drive the longitudinally-movable drive member to effectuate the end effector (2008). For example, the motor (2014) can be configured to drive the longitudinally-movable drive member to advance a firing mechanism to fire staples into tissue captured by the end effector (2008) from a staple cartridge assembled with the end effector (2008) and/or advance a cutting member to cut tissue captured by the end effector (2008), for example, in a similar manner described with respect to end effector (300).

In certain circumstances, the surgical instrument (2000) may comprise a lockout mechanism to prevent a user from coupling incompatible handle assemblies and power assemblies. For example, the power assembly (2006) may include a mating element. In certain circumstances, the mating element can be a tab extending from the power assembly (2006). In certain instances, the handle assembly (2002) may comprise a corresponding mating element (not shown) for mating engagement with the mating element. Such an arrangement can be useful in preventing a user from coupling incompatible handle assemblies and power assemblies.

Still referring to FIGS. 12-1 and 12-2, the shaft assembly (2004) may include a shaft assembly controller (2022) that can communicate with the power management controller (2016) through an interface (2024) while the shaft assembly (2004) and the power assembly (2006) are coupled to the handle assembly (2002). For example, the interface (2024) may comprise a first interface portion (2025) that may include one or more electric connectors (2026) (e.g., electrical connectors 4001a-f as shown in FIGS. 3A-3B) for coupling engagement with corresponding shaft assembly electric connectors (2028) (e.g., electrical connectors 4011a-f as shown in FIG. 3A) and a second interface portion (2027) that may include one or more electric connectors (2030) for coupling engagement with corresponding power assembly electric connectors (2032) to permit electrical communication between the shaft assembly controller (2022) and the power management controller (2016) while the shaft assembly (2004) and the power assembly (2006) are coupled to the handle assembly (2002). One or more communication signals can be transmitted through the interface (2024) to communicate one or more of the power requirements of the attached interchangeable shaft assembly (2004) to the power management controller (2016). In response, the power management controller may modulate the power output of the battery (2007) of the power assembly (2006), as described below in greater detail, in accordance with the power requirements of the attached shaft assembly (2004). In certain circumstances, one or more of the electric connectors (2026, 2028, 2030, and/or 2032) may comprise switches that can be activated after mechanical coupling engagement of the handle assembly (2002) to the shaft assembly (2004) and/or to the power assembly (2006) to allow electrical communication between the shaft assembly controller (2022) and the power management controller (2016).

In certain circumstances, the interface (2024) can facilitate transmission of the one or more communication signals between the power management controller (2016) and the shaft assembly controller (2022) by routing such communication signals through a main controller (2017) residing in the handle assembly (2002), for example. In other circumstances, the interface (2024) can facilitate a direct line of communication between the power management controller (2016) and the shaft assembly controller (2022) through the handle assembly (2002) while the shaft assembly (2004) and the power assembly (2006) are coupled to the handle assembly (2002).

In one instance, the main microcontroller (2017) may be any single core or multicore processor such as those known under the trade name ARM Cortex by Texas Instruments. In one instance, the surgical instrument (2000) may comprise a power management controller (2016) such as, for example, a safety microcontroller platform comprising two microcontroller-based families such as TMS570 and RM4x known under the trade name Hercules ARM Cortex R4, also by Texas Instruments. Nevertheless, other suitable substitutes for microcontrollers and safety processor may be employed, without limitation. In one instance, the safety processor (1004) may be configured specifically for IEC 61508 and ISO 26262 safety critical applications, among others, to provide advanced integrated safety features while delivering scalable performance, connectivity, and memory options.

In certain instances, the microcontroller (2017) may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

B. Exemplary Power Output Management Circuit and Method

Figure 13:
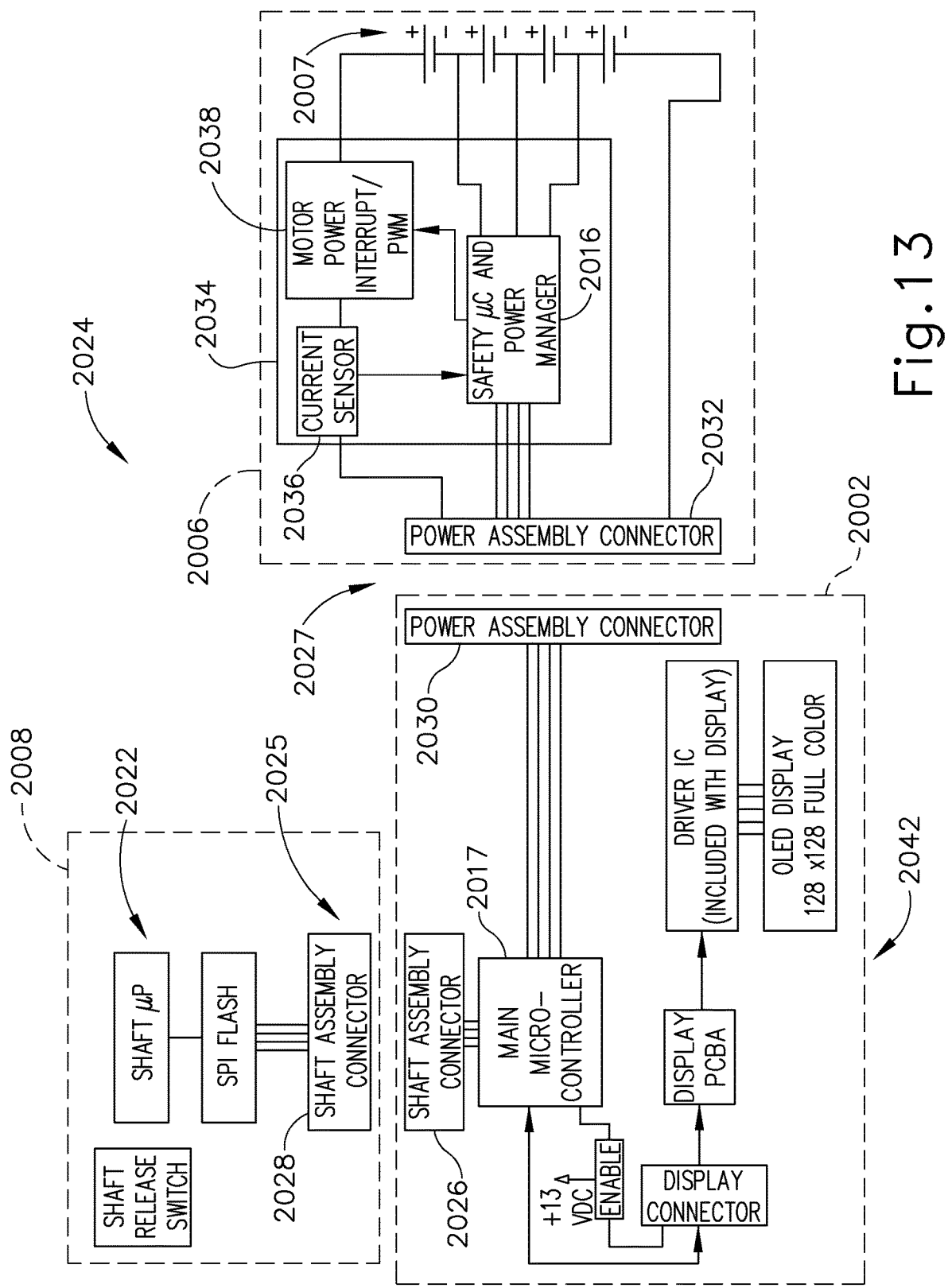
FIG. 13 depicts a block diagram of the surgical instrument of FIG. 1, showing interfaces between the handle assembly and the power assembly and interfaces between the handle assembly and shaft assembly.
Figure 14:
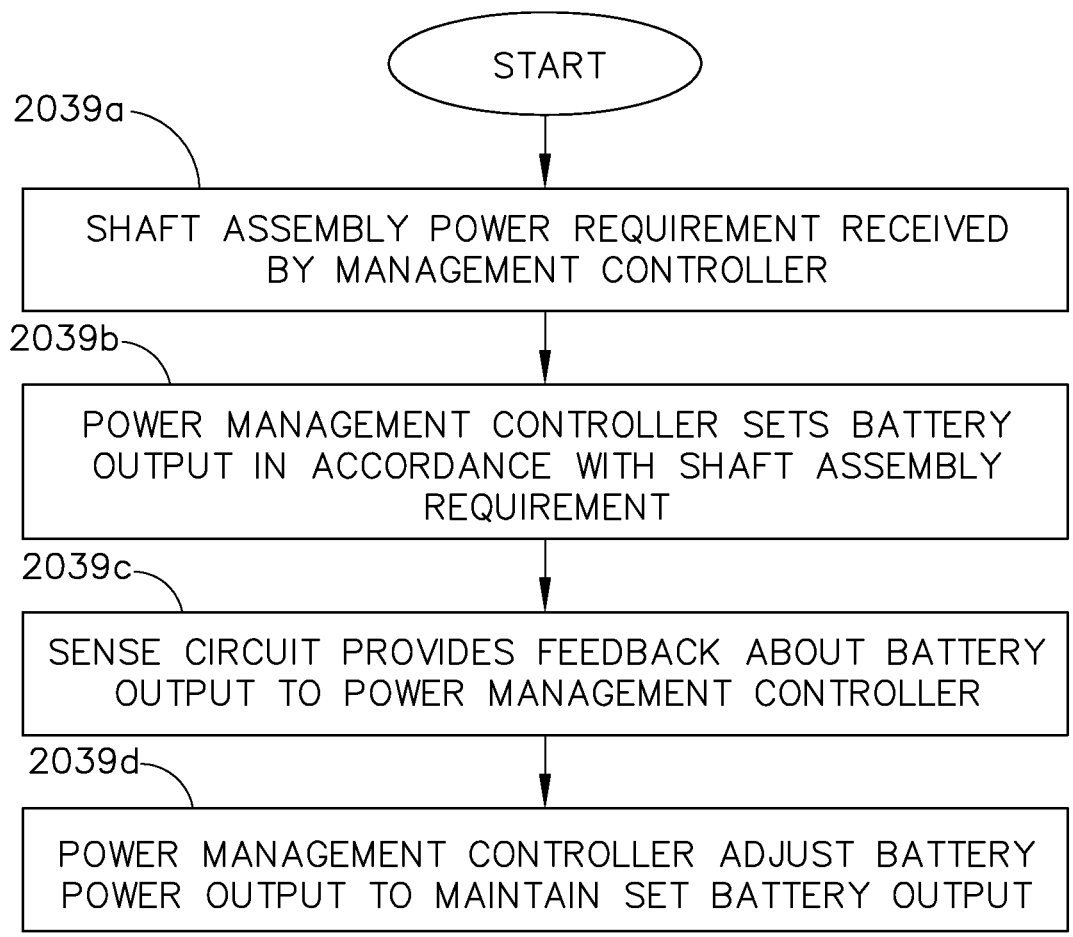
FIG. 14 depicts a power management module of the surgical instrument of FIG. 1.

Referring now primarily to FIGS. 13 and 14, the power assembly (2006) may include a power management circuit (2034) that may comprise the power management controller (2016), a power modulator (2038), and a current sense circuit (2036). The power management circuit (2034) can be configured to modulate power output of the battery (2007) based on the power requirements of the shaft assembly (2004) while the shaft assembly (2004) and the power assembly (2006) are coupled to the handle assembly (2002). For example, the power management controller (2016) can be programmed to control the power modulator (2038) of the power output of the power assembly (2006) and the current sense circuit (2036) can be employed to monitor power output of the power assembly (2006) to provide feedback to the power management controller (2016) about the power output of the battery (2007) so that the power management controller (2016) may adjust the power output of the power assembly (2006) to maintain a desired output, as illustrated in FIG. 14.

It is noteworthy that the power management controller (2016) and/or the shaft assembly controller (2022) each may comprise one or more processors and/or memory units that may store a number of software modules. Although certain modules and/or blocks of the surgical instrument (2000) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, Digital Signal Processors (DSPs), Programmable Logic Devices (PLDs), Application Specific Integrated Circuits (ASICs), circuits, registers and/or software components, e.g., programs, subroutines, logic and/or combinations of hardware and software components.

In certain instances, the surgical instrument (2000) may comprise an output device (2042) that may include one or more devices for providing a sensory feedback to a user. Such devices may comprise, for example, visual feedback devices (e.g., an LCD display screen, LED indicators), audio feedback devices (e.g., a speaker, a buzzer), and/or tactile feedback devices (e.g., haptic actuators). In certain circumstances, the output device (2042) may comprise a display that may be included in the handle assembly (2002). The shaft assembly controller (2022) and/or the power management controller (2016) can provide feedback to a user of the surgical instrument (2000) through the output device (2042). The interface (2024) can be configured to connect the shaft assembly controller (2022) and/or the power management controller (2016) to the output device (2042). Those of ordinary skill in the art will appreciate that the output device (2042) can instead be integrated with the power assembly (2006). In such circumstances, communication between the output device (2042) and the shaft assembly controller (2022) may be accomplished through the interface (2024) while the shaft assembly (2004) is coupled to the handle assembly (2002).

In certain instances, the microcontroller (2017) may be an LM 4F230H5QR, available from Texas Instruments, for example. In at least one example, the Texas Instruments LM4F230H5QR is an ARM Cortex-M4F Processor Core comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, among other features that are readily available for the product datasheet. The present disclosure should not be limited in this context.

Still referring to FIGS. 13 and 14, the power assembly (2006) may include a power management circuit (2034) that may comprise the power management controller (2016), a power modulator (2038), and a current sense circuit (2036). The power management circuit (2034) can be configured to modulate power output of the battery (2007) based on the power requirements of the shaft assembly (2004) (blocks 2039*a*, 2039*b*) while the shaft assembly (2004) and the power assembly (2006) are coupled to the handle assembly (2002). For example, the power management controller (2016) can be programmed to control the power modulator (2038) of the power output of the power assembly (2006). The current sense circuit (2036) can be employed to monitor power output of the power assembly (2006) to provide feedback to the power management controller (2016) about the power output of the battery (2007) (block 2039*c*) so that the power management controller (2016) may adjust the power output of the power assembly (2006) to maintain a desired output (block 2039*d*).

C. Exemplary Charge State Circuit and Method

Figure 15:
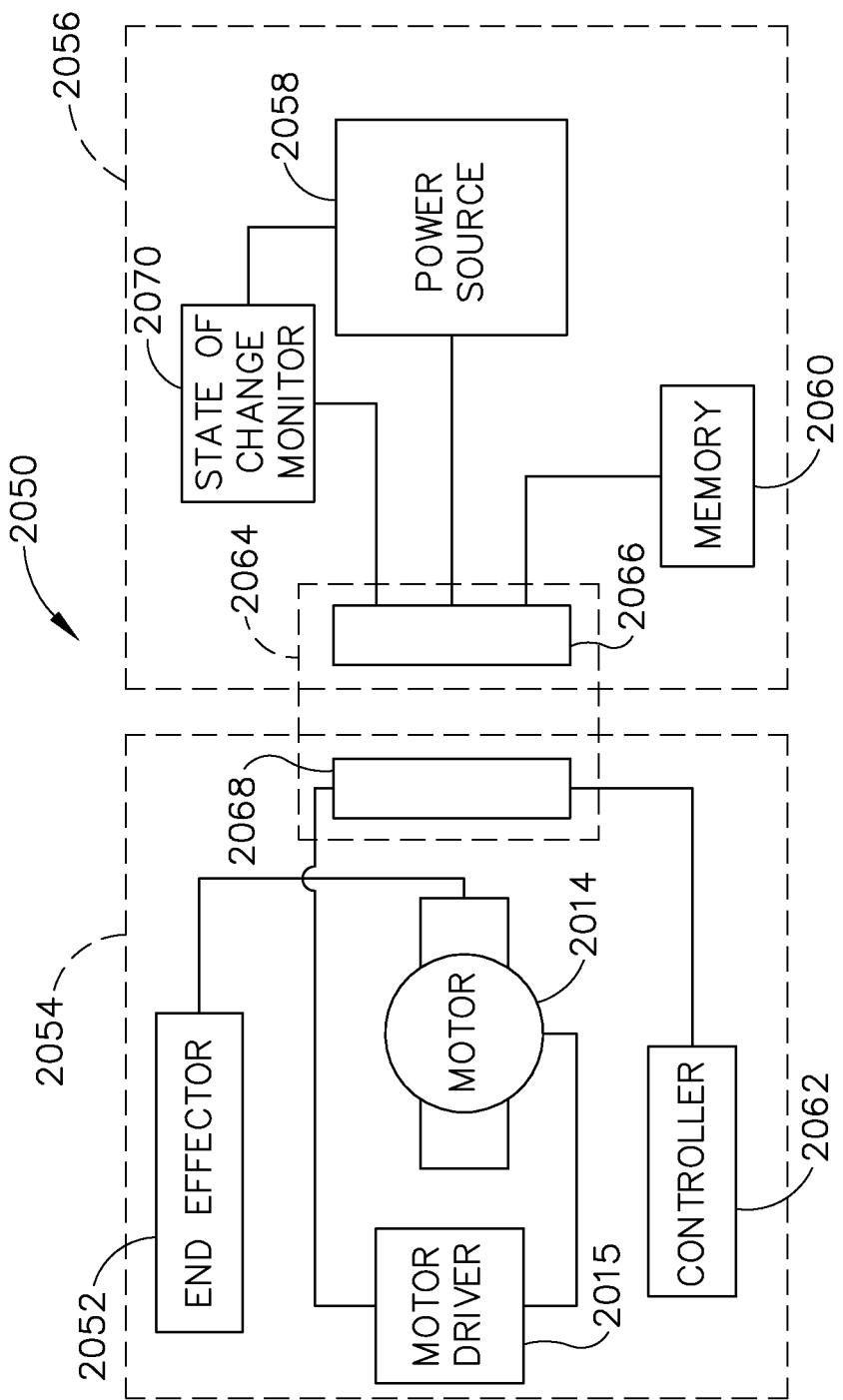
FIG. 15 depicts a block diagram of the surgical instrument of FIG. 1, showing an interface between the interchangeable working assembly and the power assembly.

FIG. 15 shows another exemplary electrical circuit and component arrangement that may be incorporated into instrument (10). By way of example only, at least a portion of the circuit shown in FIG. 15 may be incorporated into circuit board (100) described above. As shown, the arrangement includes a working assembly (2054) and a power assembly (2056). Working assembly (2054) of this example comprises a handle assembly (e.g., like handle assembly (14) described above, etc.) and a shaft assembly (e.g., like shaft assembly (200) described above, etc.) extending between the handle assembly and the end effector (2052) (which may comprise an end effector (300) as described above, etc.). In certain instances, the surgical instrument (2050) may include a power assembly (2056) (e.g., similar to power source (90) described above, etc.) that can be employed with a plurality of interchangeable working assemblies such as, for example, the interchangeable working assembly (2054). Such interchangeable working assemblies (2054) may include surgical end effectors such as, for example, the end effector (2052) that can be configured to perform one or more surgical tasks or procedures, similar to the end effector (300) described herein. In certain circumstances, the handle assembly (2053) and the shaft (2055) may be integrated into a single unit. In other circumstances, the handle assembly (2053) and the shaft (2055) may removably attached to each other. The power assembly (2056) may be provided as a variation of power source (90) described above.

Similar to the surgical instrument (2000), the surgical instrument (2050) may operably support a plurality of drive systems that can be powered by the power assembly (2056) while the power assembly (2056) is coupled to the interchangeable working assembly (2054). For example, the interchangeable working assembly (2054) can operably support a closure drive system, which may be employed to apply closing and opening motions to the end effector (2052). In at least one example, the interchangeable working assembly (2054) may operably support a firing drive system that can be configured to apply firing motions to the end effector (2052). Examples of drive systems suitable for use with the surgical instrument (2050) are described in U.S. Provisional Patent Application Ser. No. 61/782,866, entitled "Control System of a Surgical Instrument," and filed Mar. 14, 2013, the entire disclosure of which is incorporated by reference herein in its entirety.

Referring to FIG. 15, the power assembly (2056) of the surgical instrument (2050) can be removably coupled to an interchangeable working assembly such as, for example, the interchangeable working assembly (2054). Various coupling means can be utilized to releasably couple the power assembly (2056) to the interchangeable working assembly (2054). Exemplary coupling mechanisms are described herein and are described in the aforementioned U.S. Provisional Patent Application Ser. No. 61/782,866. Still referring to FIG. 15, the power assembly (2056) may include a power source (2058) such as, for example, a battery that can be configured to power the interchangeable working assembly (2054) while coupled to the power assembly (2056). In certain instances, the power assembly (2056) may include a memory (2060) that can be configured to receive and store information about the battery (2058) and/or the interchangeable working assembly (2054) such as, for example, the state of charge of the battery (2058), the number of treatment cycles performed using the battery (2058), and/or identification information for the interchangeable working assemblies coupled to the power assembly (2056) during the life cycle of the battery (2058). Further to the above, the interchangeable working assembly (2054) may include a controller (2062) that can be configured to provide the memory (2060) with such information about the battery (2058) and/or the interchangeable working assembly (2054).

Still referring to FIG. 15, the power assembly (2056) may include an interface (2064) that can be configured to facilitate electrical communication between the memory (2060) of the power assembly (2056) and a controller of an interchangeable working assembly that is coupled to the power assembly (2056) such as, for example, the controller (2062) of the interchangeable working assembly (2054). For example, the interface (2064) may comprise one or more connectors (2066) for coupling engagement with corresponding working assembly connectors (2068) to permit electrical communication between the controller (2062) and the memory (2060) while the interchangeable working assembly (2054) is coupled to the power assembly (2056). In certain circumstances, one or more of the electric connectors (2066) and/or (2068) may comprise switches that can be activated after coupling engagement of the interchangeable working assembly (2054) and the power assembly (2056) to allow electric communication between the controller (2062) and the memory (2060).

Still referring to FIG. 15, the power assembly (2056) may include a state of charge monitoring circuit (2070). In certain circumstances, the state of charge monitoring circuit (2070) may comprise a coulomb counter. The controller (2062) can be in communication with the state of charge monitoring circuit (2070) while the interchangeable working assembly (2054) is coupled to the power assembly (2056). The state of charge monitoring circuit (2070) can be operable to provide for accurate monitoring of charge states of the battery (2058).

Figure 16:
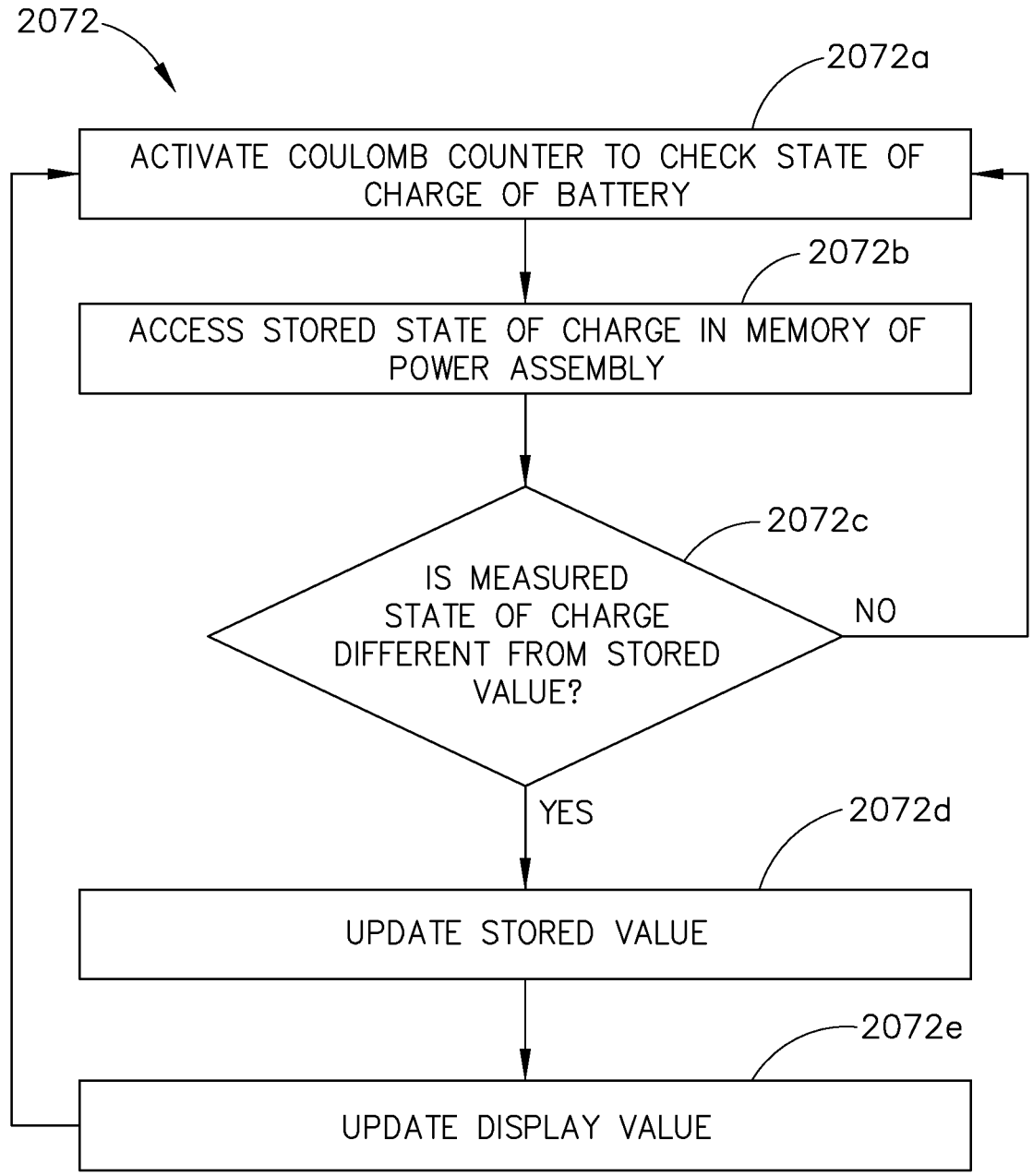
FIG. 16 depicts a block diagram showing a module of the surgical instrument of FIG. 1.

FIG. 16 shows a flowchart depicting an exemplary method of use of a controller of an interchangeable working assembly such as, for example, the controller (2062) of the interchangeable working assembly (2054) while coupled to the power assembly (2056). For example, the controller (2062) may comprise one or more processors and/or memory units that may store a number of software modules such as, for example, the module (2072). Although certain modules and/or blocks of the surgical instrument (2050) may be described by way of example, it can be appreciated that a greater or lesser number of modules and/or blocks may be used. Further, although various instances may be described in terms of modules and/or blocks to facilitate description, such modules and/or blocks may be implemented by one or more hardware components, e.g., processors, DSPs, PLDs, ASICs, circuits, registers and/or software components, e.g., programs, subroutines, logic and/or combinations of hardware and software components.

Upon coupling the interchangeable working assembly (2054) to the power assembly (2056), the interface (2064) may facilitate communication between the controller (2062) and the memory (2060) and/or the state of charge monitoring circuit (2070) to execute the module (2072), as illustrated in FIG. 16. For example, the controller (2062) of the interchangeable working assembly (2054) may utilize the state of charge monitoring circuit (2070) to measure the state of charge of the battery (2058) (block 2072a). The controller (2062) may then access the memory (2060) and determine whether a previous value for the state of charge of the battery (2058) is stored in the memory (2060) (block 2072b). When a previous value is detected, the controller (2060) may compare the measured value to the previously stored value (block 2072c). When the measured value is different from the previously stored value, the controller (2060) may update the previously stored value (block 2072d). When no value is previously recorded, the controller (2060) may store the measured value into the memory (2060). In certain circumstances, the controller (2060) may provide visual feedback to a user of the surgical instrument (2050) as to the measured state of charge of the battery (2058). For example, the controller (2060) may display the measured value of the state of charge of the battery (2058) on an LCD display screen that, in some circumstances, can be integrated with the interchangeable working assembly (2054) (block 2072e).

Further to the above, the module (2072) also can be executed by other controllers upon coupling the interchangeable working assemblies of such other controllers to the power assembly (2056). For example, a user may disconnect the interchangeable working assembly (2054) from the power assembly (2056). The user may then connect another interchangeable working assembly comprising another controller to the power assembly (2056). Such controller may in turn utilize the coulomb counting circuit (2070) to measure the state of charge of the battery (2058) and may then access the memory (2060) and determine whether a previous value for the state of charge of the battery (2058) is stored in the memory (2060) such as, for example, a value entered by the controller (2060) while the interchangeable working assembly (2054) was coupled to the power assembly (2056). When a previous value is detected, the controller may compare the measured value to the previously stored value. When the measured value is different from the previously stored value, the controller may update the previously stored value.

D. Exemplary Power Modulation Circuit and Method

Figure 17:
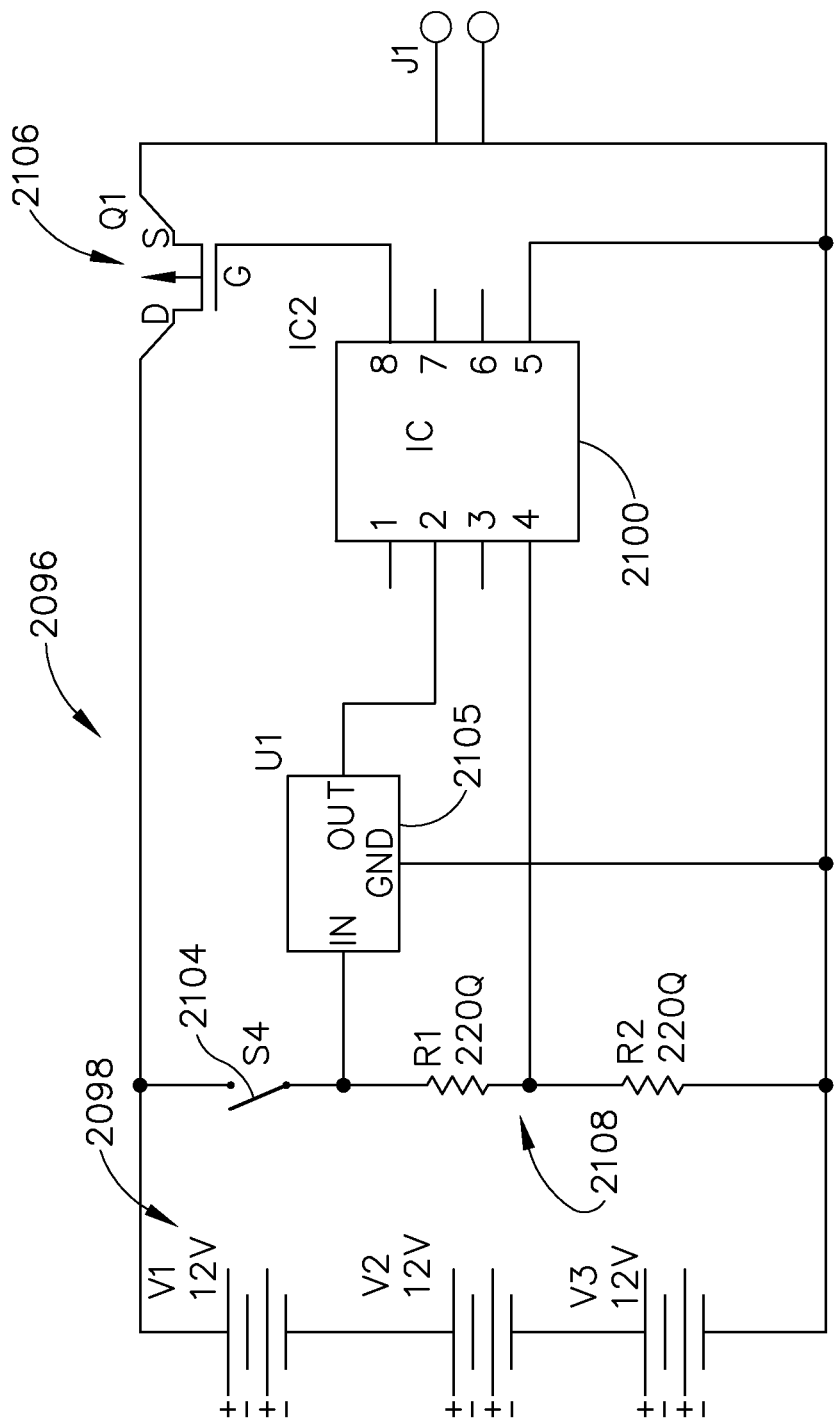
FIG. 17 depicts an exemplary circuit diagram of an alternative exemplary power assembly of the surgical instrument of FIG. 1.
Figure 18:
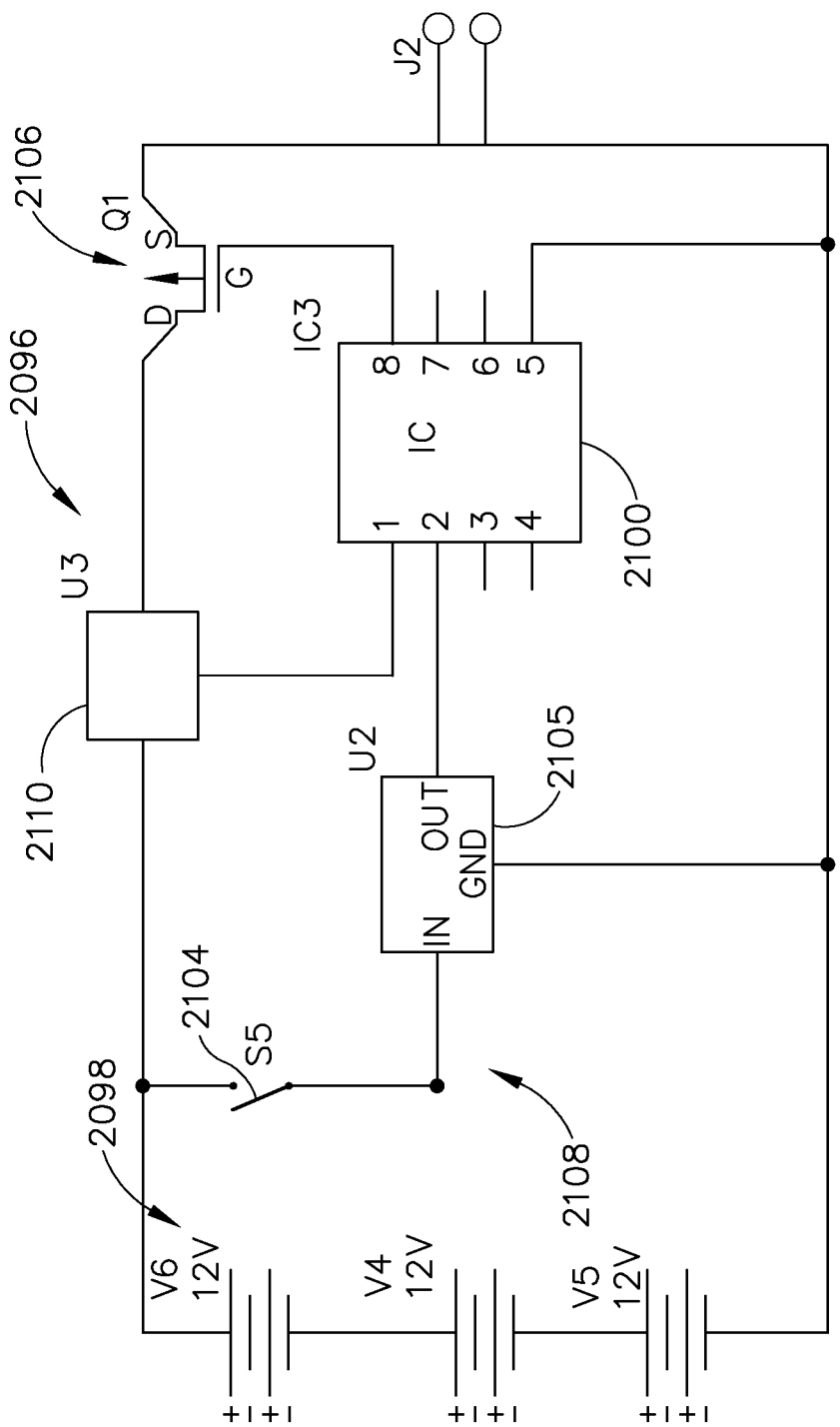
FIG. 18 depicts an exemplary alternative circuit diagram of the power assembly of the surgical instrument of FIG. 1.
Figure 19:
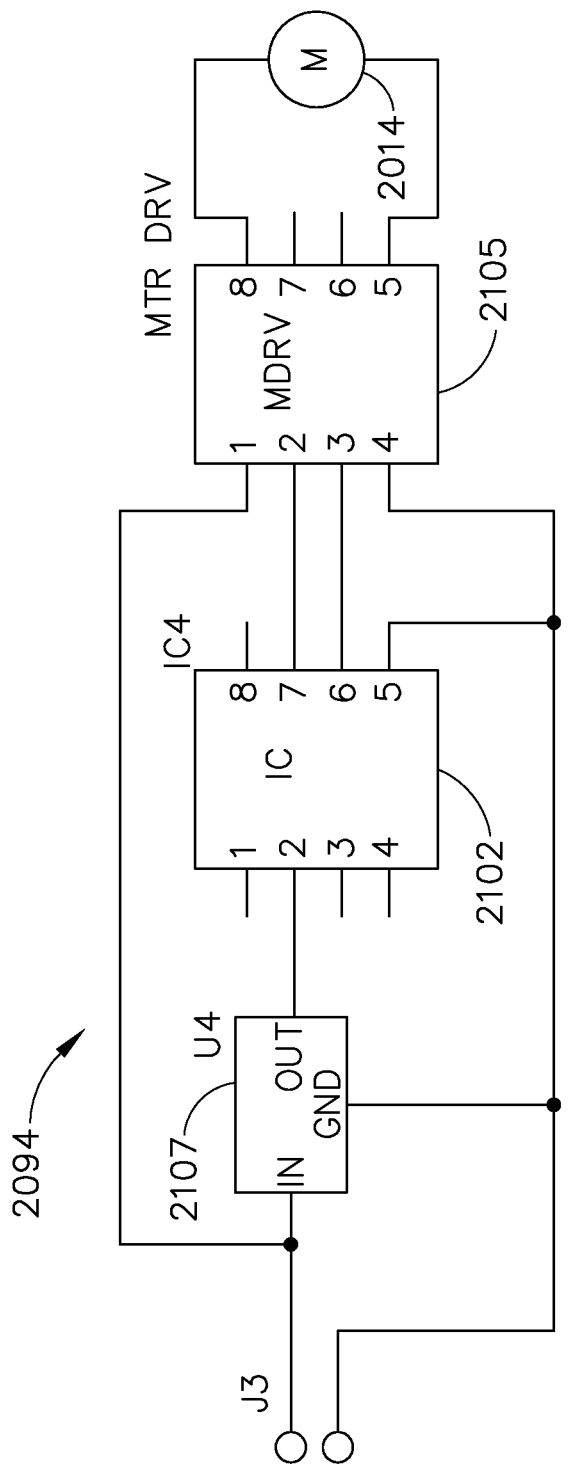
FIG. 19 depicts an exemplary circuit diagram of the interchangeable working assembly of the surgical instrument of FIG. 1.

FIGS. 17-19 show an exemplary circuit diagram of an exemplary alternative power assembly (2096) that may be used with a working assembly (2094) to form an instrument like instrument (10). Working assembly (2094) of this example comprises a handle assembly (e.g., like handle assembly (14) described above, etc.) and a shaft assembly (e.g., like shaft assembly (200) described above, etc.) extending between the handle assembly an end effector (e.g., like end effector (300) described above, etc.). The interchangeable working assembly (2094) of this example also includes a motor (2014) (e.g., like motor (82) described above, etc.) and a motor driver (2015) that can be employed to motivate the closure drive system and/or the firing drive system of the interchangeable working assembly (2094), for example. The motor (2014) can be powered by a battery (2098) that may reside in the power assembly (2096). The power assembly (2096) may be provided as a variation of power source (90) described above.

As illustrated in FIGS. 17 and 18, the battery (2098) may include a number of battery cells connected in series that can be used as a power source to power the motor (2014). In certain instances, the battery cells of the power assembly (2096) may be replaceable and/or rechargeable. The battery cells can be Lithium-Ion batteries that can be removably attached to the power assembly (2096), for example. In use, a voltage polarity provided by the power assembly (2096) can operate the motor (2014) to drive a longitudinally-movable drive member to effectuate an end effector, such as the end effector (300) described herein. For example, the motor (2014) can be configured to drive the longitudinally-movable drive member to advance a cutting member to cut tissue captured by the end effector (300) and/or a firing mechanism to fire staples from a staple cartridge assembled with the end effector (300), for example. The staples can be fired into tissue captured by the end effector (300), for example.

Still referring to FIGS. 17-19, the interchangeable working assembly (2094) may include a working assembly controller (2102); and the power assembly (2096) may include a power assembly controller (2100). The working assembly controller (2102) can be configured to generate one or more signals to communicate with the power assembly controller (2100). In certain instances, the working assembly controller (2102) may generate the one or more signals to communicate with the power assembly controller (2100) by modulating power transmission from the power assembly (2096) to the interchangeable working assembly (2094) while the power assembly (2096) is coupled to the interchangeable working assembly (2094).

Furthermore, the power assembly controller (2100) can be configured to perform one or more functions in response to receiving the one or more signals generated by the working assembly controller (2102). For example, the interchangeable working assembly (2094) may impose a power requirement and the working assembly controller (2102) may be configured to generate a signal to instruct the power assembly controller (2100) to select a power output of the battery (2098) in accordance with the power requirement of the interchangeable working assembly (2094). The signal can be generated, as described above, by modulating power transmission from the power assembly (2096) to the interchangeable working assembly (2094) while the power assembly (2096) is coupled to the interchangeable working assembly (2094). In response to receiving the signal, the power assembly controller (2100) may set the power output of the battery (2098) to accommodate the power requirement of the interchangeable working assembly (2094). Those of ordinary skill in the art will appreciate that various interchangeable working assemblies may be utilized with the power assembly (2096). The various interchangeable working assemblies may impose various power requirements and may generate signals unique to their power requirements during their coupling engagement with the power assembly (2096) to alert the power assembly controller (2100) to set the power output of the battery (2098) in accordance with their power requirements.

Still referring to FIGS. 17 and 18, the power assembly (2096) may include a power modulator control (2106) that may comprise, for example, one or more field-effect transistors (FETs), a Darlington array, an adjustable amplifier, and/or any other power modulator. The power assembly controller (2100) may actuate the power modulator control (2106) to set the power output of the battery (2098) to the power requirement of the interchangeable working assembly (2094) in response to the signal generated by working assembly controller (2102) while the interchangeable working assembly (2094) is coupled to the power assembly (2096).

The power assembly controller (2100) can be configured to monitor power transmission from the power assembly (2096) to the interchangeable working assembly (2094) for the one or more signals generated by the working assembly controller (2102) of the interchangeable working assembly (2094) while he interchangeable working assembly (2094) is coupled to the power assembly (2096). As illustrated in FIG. 17, the power assembly controller (2100) may utilize a voltage monitoring mechanism for monitoring the voltage across the battery (2098) to detect the one or more signals generated by the working assembly controller (2102), for example. In certain instances, a voltage conditioner can be utilized to scale the voltage of the battery (2098) to be readable by an Analog to Digital Converter (ADC) of the power assembly controller (2100). As illustrated in FIG. 17, the voltage conditioner may comprise a voltage divider (2108) that can create a reference voltage or a low voltage signal proportional to the voltage of the battery (2098) that can be measured and reported to the power assembly controller (2100) through the ADC, for example.

In other circumstances, as illustrated in FIG. 18, the power assembly (2096) may comprise a current monitoring mechanism for monitoring current transmitted to the interchangeable working assembly (2094) to detect the one or more signals generated by the working assembly controller (2102), for example. In certain instances, the power assembly (2096) may comprise a current sensor (2110) that can be utilized to monitor current transmitted to the interchangeable working assembly (2094). The monitored current can be reported to the power assembly controller (2100) through an ADC, for example. In other circumstances, the power assembly controller (2100) may be configured to simultaneously monitor both of the current transmitted to the interchangeable working assembly (2094) and the corresponding voltage across the battery (2098) to detect the one or more signals generated by the working assembly controller (2102). Those of ordinary skill in the art will appreciate that various other mechanisms for monitoring current and/or voltage can be utilized by the power assembly controller (2100) to detect the one or more signals generated by the working assembly controller (2102). All such mechanisms are contemplated by the present disclosure.

As illustrated in FIG. 19, the working assembly controller (2102) can be configured to generate the one or more signals for communication with the power assembly controller (2100) by effectuating the motor driver (2015) to modulate the power transmitted to the motor (2014) from the battery (2098). As a result, the voltage across the battery (2098) and/or the current drawn from the battery (2098) to power the motor (2014) may include discrete patterns or waveforms that represent the one or more signals. As described above, the power assembly controller (2100) can be configured to monitor the voltage across the battery (2098) and/or the current drawn from the battery (2098) for the one or more signals generated by the working assembly controller (2102).

Upon detecting a signal, the power assembly controller (2100) can be configured to pedal in one or more functions that correspond to the detected signal. In at least one example, upon detecting a first signal, the power assembly controller (2100) can be configured to actuate the power modulator control (2106) to set the power output of the battery (2098) to a first duty cycle. In at least one example, upon detecting a second signal, the power assembly controller (2100) can be configured to actuate the power modulator control (2106) to set the power output of the battery (2098) to a second duty cycle different from the first duty cycle.

Referring now to FIGS. 17 and 18, the power assembly (2096) may comprise a switch (2104) that can be switchable between an open position and a closed position. The switch (2104) can be transitioned from the open position to the closed positioned when the power assembly (2096) is coupled with the interchangeable working assembly (2094), for example. In certain instances, the switch (2104) can be manually transitioned from the open position to the closed position after the power assembly (2096) is coupled with the interchangeable working assembly (2094), for example. While the switch (2104) is in the open position, components of the power assembly (2096) may draw sufficiently low or no power to retain capacity of the battery (2098) for clinical use. The switch (2104) can be a mechanical, reed, hall, or any other suitable switching mechanism. Furthermore, in certain circumstances, the power assembly (2096) may include an optional power supply (2105) that may be configured to provide sufficient power to various components of the power assembly (2096) during use of the battery (2098). Similarly, the interchangeable working assembly (2094) also may include an optional power supply (2107) that can be configured to provide sufficient power to various components of the interchangeable working assembly (2094).

Figure 20:
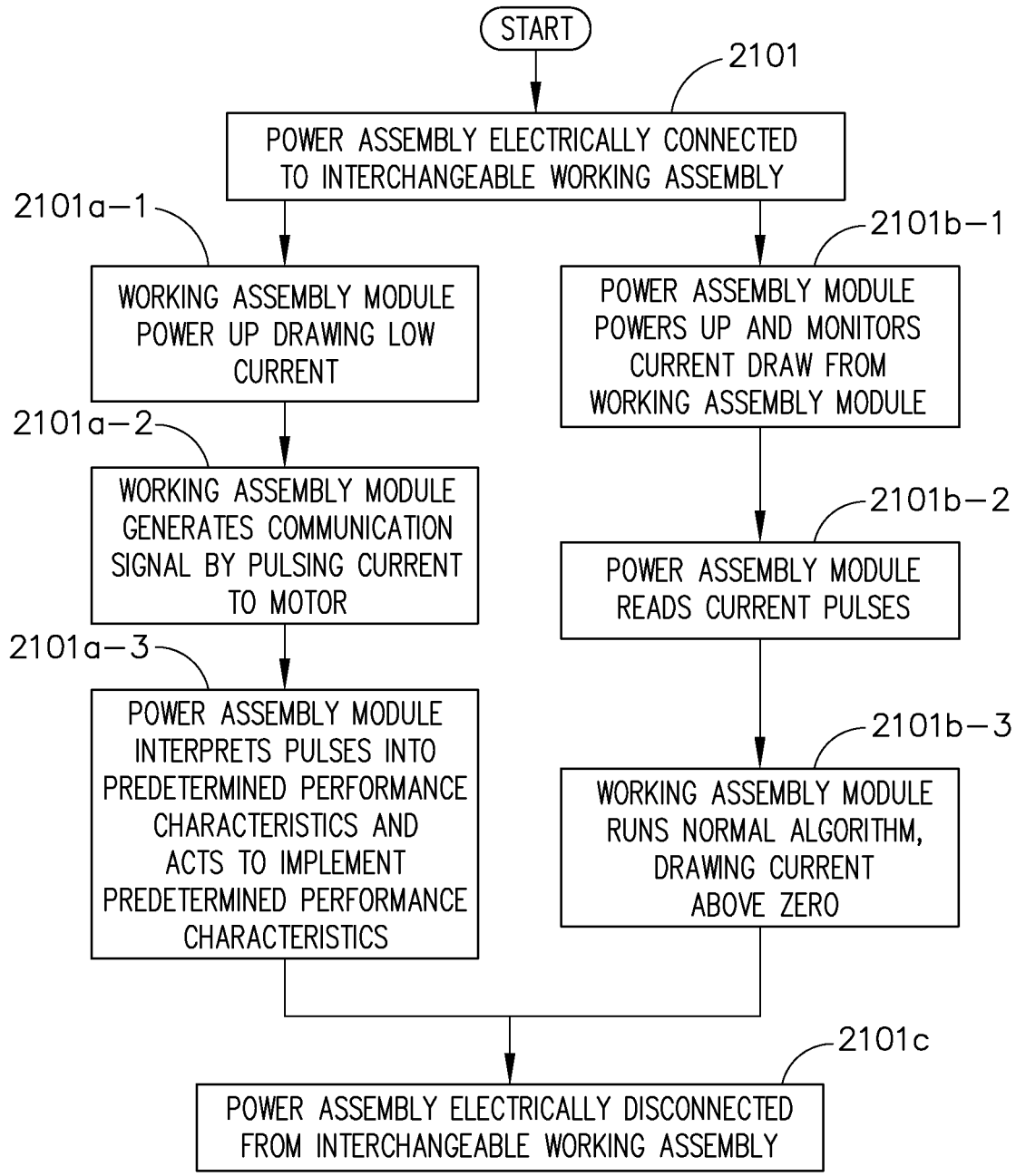
FIG. 20 depicts a block diagram showing an exemplary module of the surgical instrument of FIG. 1.

In an exemplary method, as illustrated in FIG. 20, the power assembly (2096) can be coupled to the interchangeable working assembly (2094) (block 2101). In certain instances, as described above, the switch (2104) can be transitioned to the closed configuration to electrically connect the interchangeable working assembly (2094) to the power assembly (2096). In response, the interchangeable working assembly (2094) may power up and may, at least initially, draw relatively low current from the battery (2098) (block 2101*a*-1). For example, the interchangeable working assembly (2094) may draw less than or equal to 1 ampere to power various components of the interchangeable working assembly (2094). In certain instances, the power assembly (2096) also may power up as the switch (2014) is transitioned to the closed position (block 2101*b*-1) while interchangeable working assembly (2094) powers up. In response, the power assembly controller (2100) may begin to monitor current drawn by the interchangeable working assembly (2094), as described in greater detail above, by monitoring voltage across the battery (2098) and/or current transmission from the battery (2098) to the interchangeable working assembly (2094), for example.

Figure 21A:
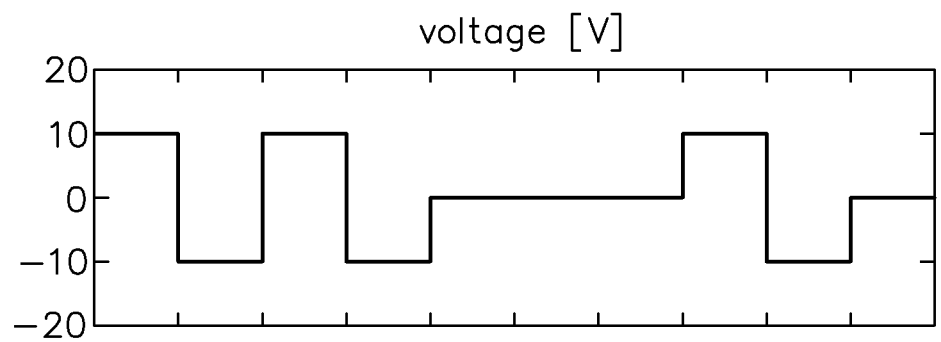
FIG. 21A depicts a graphical representation of a voltage signal generated by a working assembly controller of the interchangeable working assembly of the surgical instrument of FIG. 1.
Figure 21B:
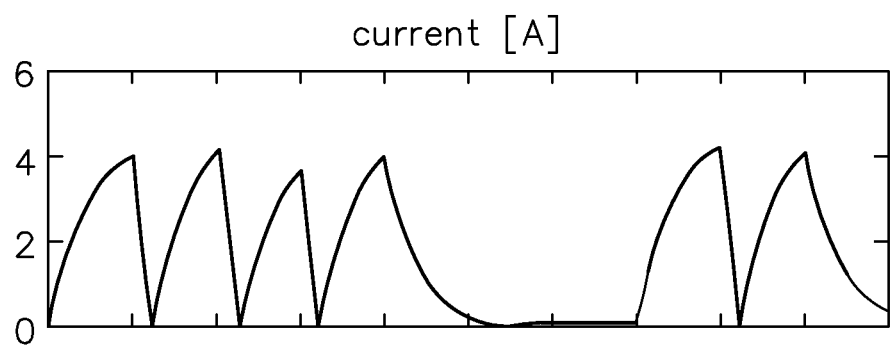
FIG. 21B depicts a graphical representation of a current signal generated by a working assembly controller of the interchangeable working assembly of the surgical instrument of FIG. 1.
Figure 21C:
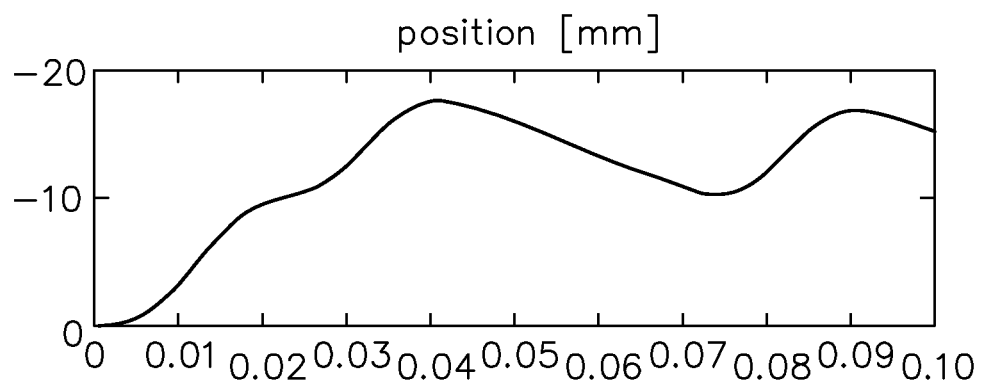
FIG. 21C depicts a graphical representation of effective motor displacement of a motor of the interchangeable working assembly of FIG. 1 in response to the voltage signal generated by the working assembly controller of FIG. 21A.

To generate and transmit a communication signal to the power assembly controller (2100) via power modulation, the working assembly controller (2102) may employ the motor drive (2015) to pulse power to the motor (2014) (block 2101*a*-2) in patterns or waveforms of power spikes, for example. In certain circumstances, the working assembly controller (2102) can be configured to communicate with the motor driver (2015) to rapidly switch the direction of motion of the motor (2014) by rapidly switching the voltage polarity across the windings of the motor (2014) to limit the effective current transmission to the motor (2014) resulting from the power spikes. In result, as illustrated in FIG. 21C, the effective motor displacement resulting from the power spikes can be reduced to minimize effective displacement of a drive system of the surgical instrument (2090) that is coupled to the motor (2014) in response to the power spikes.

Further to the above, the working assembly controller (2102) may communicate with the power assembly controller (2100) by employing the motor driver (2015) to draw power from the battery (2098) in spikes arranged in predetermined packets or groups that can be repeated over predetermined time periods to form patterns detectable by the power assembly controller (2100). For example, as illustrated in FIGS. 21A and 21B, the power assembly controller (2100) can be configured to monitor voltage across the battery (2100) for predetermined voltage patterns such as, for example, the voltage pattern (2103) (FIG. 21A) and/or predetermined current patterns such as, for example, the current pattern (2109) (FIG. 21B) using voltage and/or current monitoring mechanisms as described in greater detail above (blocks 2101*b*-2). Furthermore, the power assembly controller (2100) can be configured to execute one or more algorithms and/or functions upon detecting of a pattern of current pulses (block 2101*a*-3). Those of ordinary skill in the art will appreciate that the communication between the power assembly controller (2100) and the working assembly controller (2102) via power transmission modulation may reduce the number of connection lines needed between the interchangeable working assembly (2094) and the power assembly (2096).

In certain circumstances, the power assembly (2096) can be employed with various interchangeable working assemblies of multiple generations that may have different power requirements. Some of the various interchangeable workings assemblies may comprise communication systems, as described above, while others may lack such communication systems. For example, the power assembly (2096) can be utilized with a primary interchangeable working assembly that lacks the communication system described above. Alternatively, the power assembly (2096) can be utilized with a secondary interchangeable working assembly such as, for example, the interchangeable working assembly (2094) that comprises a communication system, as described above. Thus, the power assembly (2096) may be configured to provide power to a working assembly regardless of whether the working assembly has a communication system as described above.

Further to the above, the primary interchangeable working assembly may have a first power requirement and the secondary interchangeable working assembly may have a second power requirement that can be different from the first power requirement. For example, the first power requirement may be less than the second power requirement. To accommodate the first power requirement of the primary interchangeable working assembly and the second power requirement of the secondary interchangeable working assembly, the power assembly (2096) may comprise a first power mode for use with the primary interchangeable working assembly and a second power mode for use with the secondary interchangeable working assembly. In certain instances, the power assembly (2096) can be configured to operate at a default first power mode corresponding to the power requirement of the primary interchangeable working assembly. As such, when a primary interchangeable working assembly is connected to the power assembly (2096), the default first power mode of the power assembly (2096) may accommodate the first power requirement of the primary interchangeable working assembly. However, when a secondary interchangeable working assembly such as, for example, the interchangeable working assembly (2094), is connected to the power assembly (2096), the working assembly controller (2102) of the interchangeable working assembly (2094) may communicate, as described above, with the power assembly controller (2100) of the power assembly (2096) to switch the power assembly (2096) to the second power mode to accommodate the second power requirement of the interchangeable working assembly (2094). Those of ordinary skill in the art will appreciate that since the primary interchangeable working assembly lacks the ability to generate a communication signal, the power assembly (2096) will remain in the default first power mode while connected to the primary interchangeable working assembly.

As described above, the battery (2098) can be rechargeable. In certain circumstances, it may be desirable to drain the battery (2098) prior to shipping the power assembly (2096). A dedicated drainage circuit can be activated to drain the battery (2098) in preparation for shipping of the power assembly (2096). Upon reaching its final destination, the battery (2098) can be recharged for use during a surgical procedure. However, the drainage circuit may continue to consume energy from the battery (2098) during clinical use. In certain circumstances, the interchangeable working assembly controller (2102) can be configured to transmit a drainage circuit deactivation signal to the power assembly controller (2100) by modulating power transmission from the battery (2098) to the motor (2014), as described in greater detail above. The power assembly controller (2100) can be programmed to deactivate the drainage circuit to prevent drainage of the battery (2098) by the drainage circuit in response to the drainage circuit deactivation signal, for example. The reader will appreciate that various communication signals can be generated by the working assembly controller (2102) to instruct the power assembly controller (2100) to pedal various functions while the power assembly (2096) is coupled to the interchangeable working assembly (2094).

Referring again to FIGS. 17-19, the power assembly controller (2100) and/or the working assembly controller (2102) may comprise one or more processors and/or memory units that may store a number of software modules. Although certain modules and/or blocks of the surgical instrument (2050) may be described by way of example, it can be appreciated that a greater or lesser number of modules and/or blocks may be used. Further, although various instances may be described in tennis of modules and/or blocks to facilitate description, such modules and/or blocks may be implemented by one or more hardware components, e.g., processors, DSPs, PLDs, ASICs, circuits, registers and/or software components, e.g., programs, subroutines, logic and/or combinations of hardware and software components.

III. Exemplary Battery Pack Circuits and Methods of Operation

Figure 22:
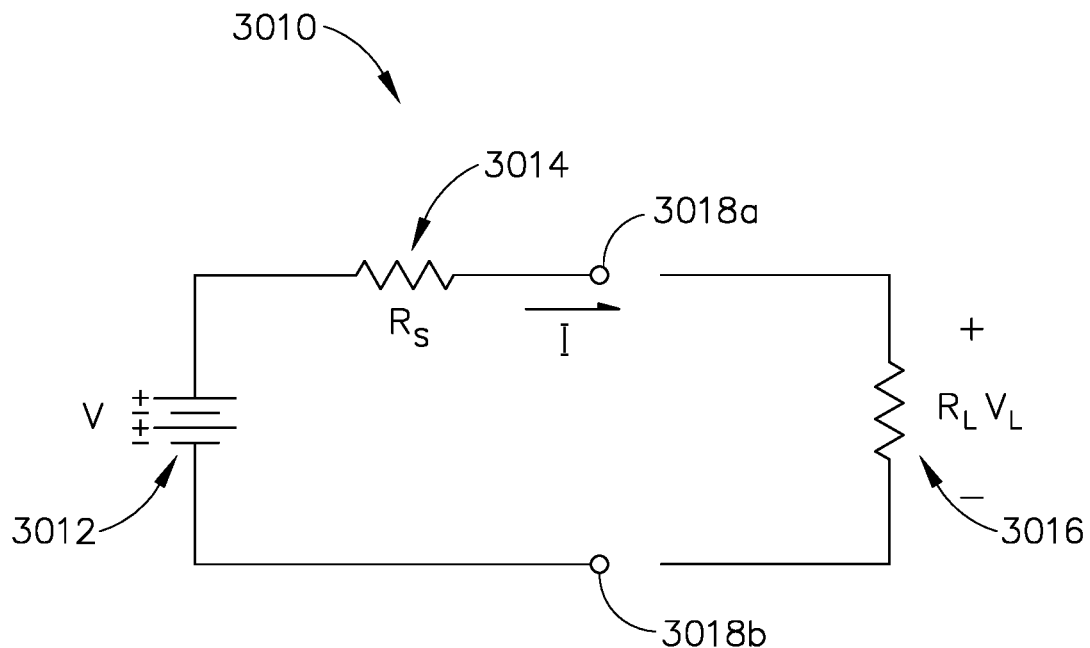
FIG. 22 depicts a circuit diagram for an exemplary power assembly of the instrument of FIG. 1.

FIG. 22 shows a schematic diagram of a circuit (3010) that may be provided by power pack (92). Circuit (3010) includes a set of power cells (3012), which are provided by batteries (98) in this example; an effective series resistor (3014), which may be provided by various electrical components as will be apparent to those of ordinary skill in the art in view of the teachings herein; and a pair of terminals (3018a, 3018b), which may be provided as a set of contacts that are exposed through distal housing portion (96). Terminals (3018a, 3018b) may be coupled with complementary contacts in handle assembly (14), which is represented in FIG. 22 by a symbol for a load resistor (3016). As described above, power pack (92), and hence circuit (3010), provides electrical power that is operable to drive motor (82) and other electrical components of instrument (10). In the present example, power cells (3012) are non-rechargeable. Power pack (92) is thus provided and configured for disposal after the power from cells (3012)/batteries (98) has been consumed. In other words, power pack (92) is provided with instrument (10) as a "primary" battery pack, such that power pack (92) is intended to be the first (and only) battery pack that is to be used with instrument (10). In some versions, power pack (92) and other devices referred herein to as "primary" battery packs or "primary" power packs/sources comprise one or more non-rechargeable batteries. As will be understood by a person skilled in the art, as shown in FIG. 22, the value "V" represents the open circuit voltage of cells (3012), the value "$R_S$" represents the effective series resistance provided by effective series resistor (3014), the value "$R_L$" represents the load resistance imposed by motor (82) and other electrical components of instrument (10), the value "$V_L$" represents the load voltage of motor (82) and other electrical components of instrument (10), and the value "I" represents the =current drawn through circuit (3010). As will be further understood by a person skilled in the art, the load voltage ($V_L$) may be calculated as $V_L=IR_L$. The current (I) may be calculated as $I=V/(R_S+R_L)$. The load voltage ($V_L$) may thus be further calculated as $V_L=VR_L/(R_S+R_L)$.

Figure 23:
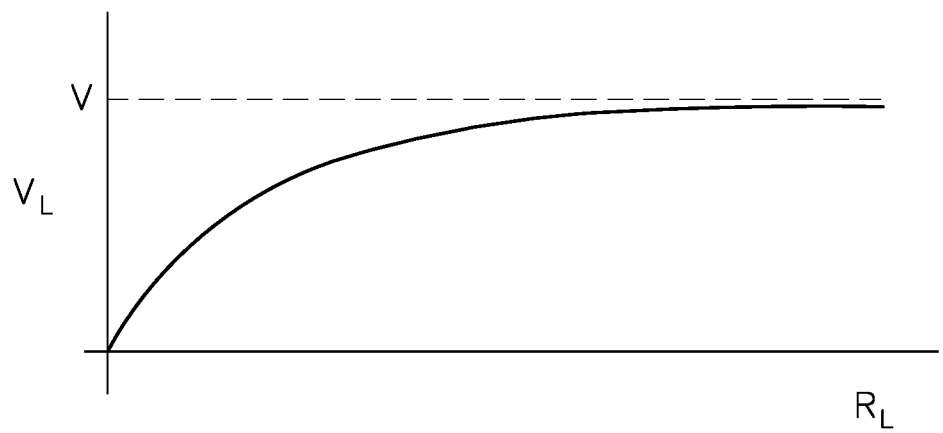
FIG. 23 depicts a plot of voltage versus resistance for the battery pack of FIG. 22.

An exemplary plot of load resistance ($R_L$) versus load voltage ($V_L$) is shown in FIG. 23. As shown, the load voltage ($V_L$) increases in a non-linear fashion as the load resistance ($R_L$) increases, such that the load voltage ($V_L$) approaches but does not reach the open circuit voltage (V).

In some instances, a medical device may be configured to detect battery pack characteristics in order to detect battery health, to confirm proper insertion of the battery pack, to confirm that an appropriate battery pack is inserted, etc. In instances, it may be desirable for a medical device to be operable to confirm that an appropriate battery pack is inserted in order to confirm that the battery pack is not intended for use in another device, in order to confirm that a counterfeit battery pack is not being used, an/or for other reasons. In the context of instrument (10), one or more features on circuit board (100), other features of handle assembly (14), and/or other features of instrument (10) may detect one or more characteristics of power pack (92). By way of example only, one or more features on circuit board (100), other features of handle assembly (14), and/or other features of instrument (10) may be configured to detect the effective series resistance ($R_S$) provided by effective series resistor (3014). In addition or in the alternative, one or more features on circuit board (100), other features of handle assembly (14), and/or other features of instrument (10) may be configured to detect the open circuit voltage (V) of cells (3102). In either or both cases, the detection may be performed to ensure than an appropriate power pack (92) has been coupled with handle assembly (14).

Medical devices such as instrument (10) may be indicated for multiple uses and, as a result, may require sterilization between uses. Some such devices may be designed to utilize a non-rechargeable battery that either cannot be sterilized or simply would not be sterilized for a variety of reasons. In some instances, it may be advantageous for economic, environmental, and/or various other reasons to utilize a rechargeable battery in a medical device instead of using a non-rechargeable battery in the medical device. It may further be desirable to utilize a rechargeable battery that is universal in nature such that the battery is configured to be used in various kinds of medical devices (e.g., instrument (10) and other kinds of medical devices). However, in some medical devices this may not be possible due to battery detection features that may be present in the medical device. In other words, as noted above, some medical devices may be equipped with features (e.g., mechanisms and/or software, etc.) that detect characteristics of a connected battery and/or interrogate a connected battery. If certain characteristics are not detected and/or the battery pack does not properly respond to the interrogations, the medical device may prevent the battery from being properly electrically connected to the medical device. Alternatively, the medical device may not operate properly if the medical device does not detect the appropriate characteristics and/or interrogation response.

In view of the foregoing, it may be desirable to provide a secondary battery pack that may be used to replace a primary battery pack that is provided with a medical device such as instrument (10). In the examples described herein, it is contemplated that the "secondary" battery packs (or "secondary" power packs/sources) described herein comprise one or more rechargeable batteries; while the "primary" battery packs (or "primary" power packs/sources) described herein comprise one or more non-rechargeable batteries. Of course, "secondary" battery packs (or "secondary" power packs/sources) described herein may instead comprise one or more non-rechargeable batteries; and/or "primary" battery packs (or "primary" power packs/sources) described herein may instead comprise one or more rechargeable batteries. Either way, it is contemplated that a secondary battery pack may be configured to express the characteristics and/or interrogation response that the medical device (e.g., instrument (10), etc.) would expect from a legitimate primary battery pack (e.g., power pack (92), etc.). Such a secondary battery pack may also be configured for use in various kinds of medical devices that have different expectations for their respective primary battery packs. The secondary battery pack may thus determine what the expectations of a medical device are and then adapt to those expectations on an ad hoc basis. Various examples of how a secondary battery pack may be configured and operable are described in greater detail below. Other examples will be apparent to those of ordinary skill in the art in view of the teachings herein.

Figure 24:
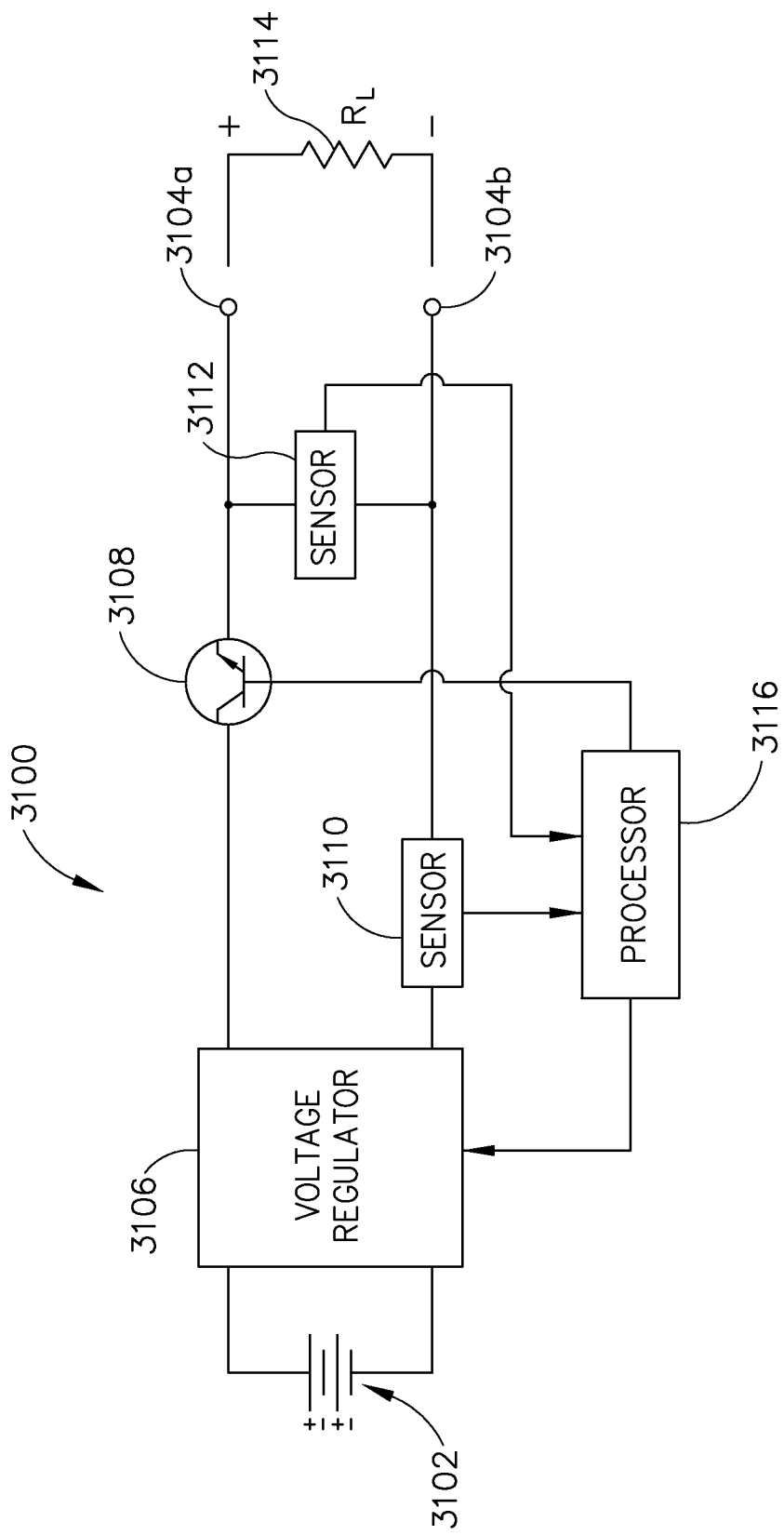
FIG. 24 depicts a schematic diagram of an exemplary circuit for an exemplary alternative power assembly of the instrument of FIG. 1.

A. Exemplary Secondary Battery Pack with Primary Battery Pack Emulation Features FIG. 24 shows a schematic circuit diagram of an exemplary alternative power assembly (3100). Power assembly (3100) is configured to respond to an interrogation by a medical device to which it is connected in a manner that emulates a primary power assembly (i.e., a primary power pack (92)), thereby convincing the medical device that the secondary power assembly (3100) is a primary power pack (92). The physical appearance and other features of the power assembly (3100) may be configured according to the teachings above. For instance, the power assembly (3100) may be configured in a similar manner to the battery/power pack (92) shown in FIG. 4, but is not so limited. Power assembly (3100) may thus be mechanically and electrically coupled with the proximal end of handle assembly (14) in a manner similar to power pack (92). In the present example, the power assembly (3100) includes a set of battery cells (3102) that are operable to provide power output through positive and negative output terminals (3104a, 3104b). Battery cells (3102) may be rechargeable or non-rechargeable. Terminals (3104a, 3104b) may be provided as a set of contacts that are exposed through a distal housing portion of power assembly (3100) (e.g., similar to distal housing portion (96)). Terminals (3104a, 3104b) may thus be coupled with complementary contacts in a handle assembly (14), working assembly (2054), etc., which are represented in FIG. 24 by a symbol for a load resistor (3114). It should be understood that terminals (3104a, 3104b) may also be coupled with complementary contacts in various other kinds of medical devices, not just surgical stapling instruments (10).

In the example shown, power assembly (3100) also includes a voltage regulator (3106), a NPN pass transistor (3108), a first sensor (3110), and a second sensor (3112). The power assembly (3100) further includes a processor (3116) in communication with each of the voltage regulator (3106), the pass transistor (3108), the first sensor (3110), and the second sensor (3112). In the example shown, the first sensor (3110) is a current sensor that is configured to sense the current level drawn through the circuit and communicate the sensed current to the processor (3116). The second sensor (3112) is a voltage sensor that is configured to sense the voltage of the circuit and communicate the sensed voltage to the processor (3116). Various suitable kinds of components that may be used to form sensors (3110, 3112) will be apparent to those of ordinary skill in the art in view of the teachings herein. It will also be appreciated that various other components and features may be used for monitoring and altering current and/or voltage in the power assembly (3100). Various suitable kinds of components that may be used to form voltage regulator (3106), pass transistor (3108), and processor (3116) will also be apparent to those of ordinary skill in the art in view of the teachings herein. By way of example only, voltage regulator (3106) may comprise a buck regulator, a boost regulator, and/or any other suitable kind of regulator(s). It should be understood that the components of power assembly (3100) may be operable to provide analog signal processing, digital signal processing, data storage, controllably variable output impedance, controllably variable output voltage, controllably variable current, and/or other functionality. Various suitable ways in which power assembly (3100) may provide such functionality will be apparent to those of ordinary skill in the art in view of the teachings herein.

While some versions of power assembly (3100) may be compatible with various kinds of medical devices in addition to being compatible with instrument (10), the following examples will be provided in the context of instrument (10) by way of illustration.

Upon coupling the power assembly (3100) to the handle assembly (14), the handle assembly (14) may detect that the power assembly (3100) is coupled with the handle assembly (14). In addition or in the alternative, the power assembly (3100) may detect that the power assembly is coupled with the handle assembly (14) as soon as those components are coupled together. For instance, in some examples, the power assembly (3100) and/or the handle assembly (14) could include one or more contact sensors that are actuated upon insertion of power assembly (3100) in handle assembly (14). In addition or in the alternative, power assembly (3100) may automatically periodically check for electrical continuity across terminals (3104a, 3104b), such that the presence of electrical continuity across terminals (3104a, 3104b) will indicate that power assembly (3100) is coupled with handle assembly (14). In addition or in the alternative, power assembly (3100) may include an inductance sensor that is sensitive to metallic components being brought into close proximity to power assembly (3100), such that close proximity of a metallic component will indicate that power assembly (3100) is coupled with handle assembly (14). Other suitable ways in which power assembly (3100) and/or handle assembly (14) may detect the coupling of power assembly (3100) with handle assembly (14) will be apparent to those of ordinary skill in the art in view of the teachings herein.

In versions where power assembly (3100) is configured to detect that power assembly (3100) has been coupled with instrument (10), power assembly (3100) may also be configured to carry out a process to determine what kind of instrument (10) power assembly (3100) is coupled with, such as by sensing characteristics of the instrument (10) as described in greater detail below with reference to FIGS. 26 through 28-2. In addition or in the alternative, in versions where instrument (10) is configured to detect that power assembly (3100) has been coupled with instrument (10), circuit board (100) and/or other electrical components of instrument (10) may generate one or more signals to communicate with the power assembly (3100) in order to interrogate the power assembly (3100). This interrogation may be performed as part of an initialization routine, boot up routine, self-test, or similar routine before instrument (10) is fully operable by a human or robotic operator. In certain instances, the instrument (10) may generate the one or more signals to interrogate or communicate with the power assembly (3100) by modulating power transmission from the power assembly (3100) to the instrument (10) while the power assembly (3100) is coupled to the instrument (10). By way of example only, instrument (10) may send the one or more interrogation signals in order to determine whether power assembly (3100) is a primary power pack (92). In addition or in the alternative, instrument (10) may interrogate power assembly (3100) to determine if the power assembly (3100) is compatible with the instrument (10). In addition or in the alternative, instrument (10) may interrogate power assembly (3100) to determine battery health, whether power assembly (3100) is properly inserted, and/or other conditions. Based on the results of the interrogation, instrument (10) may be configured to prevent the use of a counterfeit power pack/assembly or a power pack/assembly that is otherwise perceived as improper by instrument (10).

The power assembly (3100) of the present example is configured to perform one or more functions in response to receiving the one or more interrogation signals from the instrument (10) in order to convince instrument (10) that power assembly (3100) is a primary power pack (92) and/or to otherwise convince instrument (10) that power assembly (3100) is compatible with instrument (10). Therefore, it may be desirable to provide a power assembly (3100) that is configured to emulate the power profile of a primary power pack (92).

Figure 25:
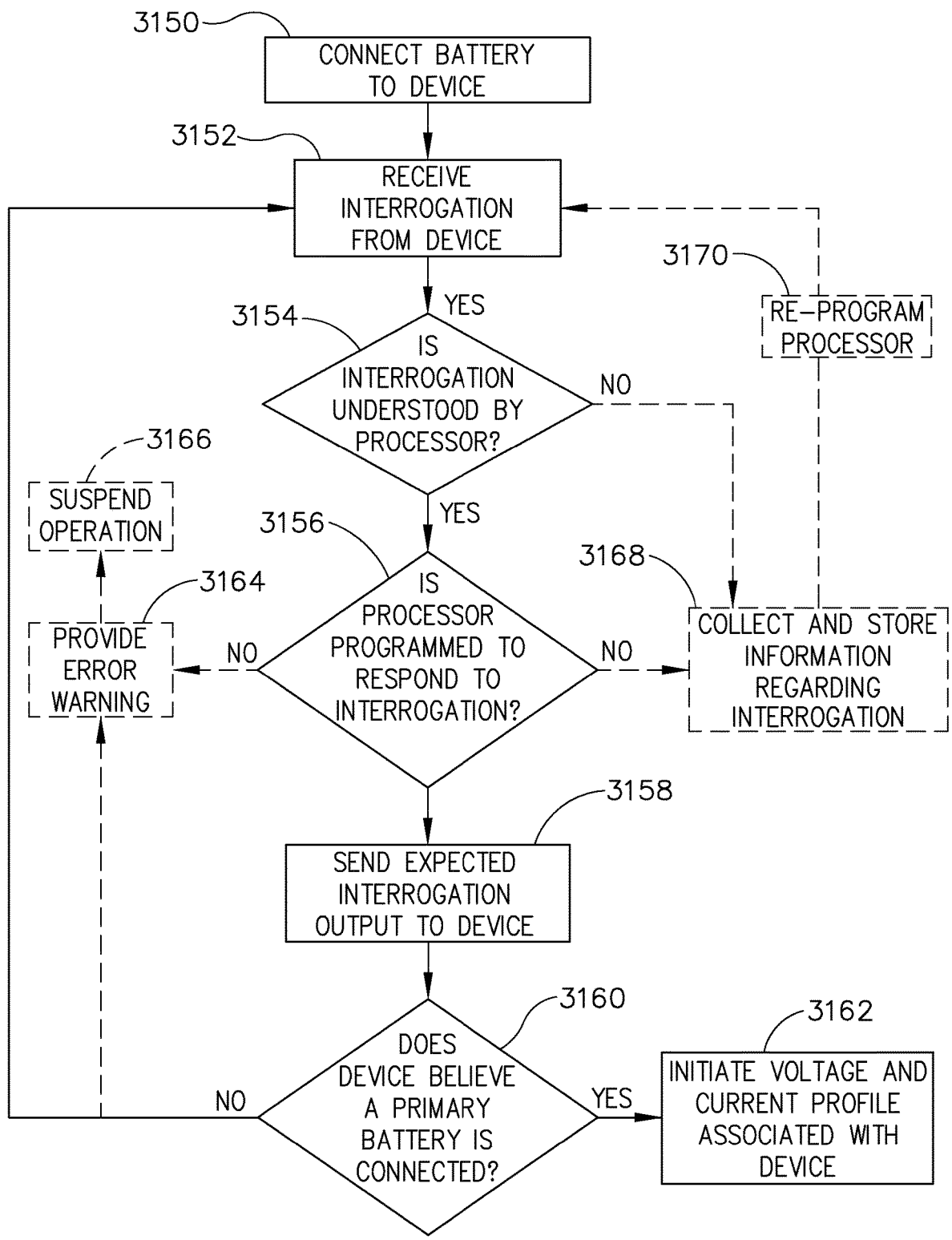
FIG. 25 depicts a flow chart showing steps carried out during one or more exemplary methods of utilizing the circuit of FIG. 24.

FIG. 25 shows an exemplary method of emulating a power profile of a primary power pack (92) that is intended for use with instrument (10). It should be understood that the method shown in FIG. 25 may be carried out using the circuit of power assembly (3100) shown in FIG. 24 or using various other circuit arrangements. Various suitable ways in which the method shown in FIG. 25 may be carried out using the circuit of power assembly (3100) shown in FIG. 24 and/or using various other circuit arrangements will be apparent to those of ordinary skill in the art in view of the teachings herein. When a user connects a battery pack, such as the power assembly (3100), to the instrument (10) (e.g., handle assembly (14), etc.) (block 3150), the instrument (10) may sense that a power assembly (3100) is connected thereto, as noted above. In the example shown, the interrogation is received by the power assembly (3100) (block 3152). If the interrogation is understood by the processor (3116) of power assembly (3100) (block 3154) and if the processor (3116) is programmed to respond to the interrogation (block 3156), the processor (3116) sends the expected response or interrogation output to the instrument (10) (block 3158). The expected response from power assembly (3100) is meant to emulate the effective series resistance ($R_S$) of a primary power pack (92) as described above. Thus, by conditioning the load voltage output ($V_L$), assuming that load resistance ($R_L$) and open circuit voltage (V) would be the same as they would be with a primary power pack (92), the power assembly (3100) can convince instrument (10) that the effective series resistance ($R_S$) of the power assembly (3100) has the same value of an effective series resistance ($R_S$) as expected from a primary power pack (92). By altering the load voltage output ($V_L$), the circuit board (100), other features of handle assembly (14), and/or other features of instrument (10) receives a voltage signal according to an assumed effective series resistance ($R_S$) value.

Placing the method shown in FIG. 25 further in context with the circuit shown in FIG. 24, in some versions the processor (3116) may receive a signal that the power assembly (3100) is connected to a handle assembly (14) and detect an interrogation by the handle assembly (14). The processor (3116) may then command the voltage regulator (3104) to adjust the load voltage ($V_L$) at the expected level associated with the expected effective series resistance ($R_S$) value, for example. The NPN pass transistor (3108) may also be configured to provide an output impedance that emulates the expected effective series resistance ($R_S$).

Continuing further with the method shown in FIG. 25, if the load voltage output ($V_L$) and thus the effective series resistance ($R_S$) value is within a range of what is expected by the instrument (10) and the instrument (10) believes that a primary power pack (92) is connected (block 3160), then the power assembly (3100) initiates a voltage and current profile associated with the instrument (10) (block 3162). The voltage and current profile associated with the shaft assembly may be constant or variable, and may be stored on a database, such as a database or other storage medium on a memory (not shown). The memory and/or database may be present on or in the power assembly (3100) itself. Alternatively or additionally, the database or part of the database may be in a nearby or remote memory and accessed according to methods that will be apparent to those skilled in the art. Additionally or alternatively, the power assembly (3100) may be configured to communicate electronically (wired, wirelessly, or otherwise) with other sources of information (e.g., manufacturer's specifications) in order to discover and/or initiate an operational profile associated with the device.

If however, the instrument (10) does not believe that power assembly (3100) is a primary power pack (92), then an error warning may optionally be provided (block 3164). The error warning may be provided by a visual, audio, and/or another indicative manner to the user; and may be provided through the power assembly (3100) and/or through the instrument (10) that is connected to the power assembly (3100). If the power assembly (3100) has performed less than a certain number of interrogation cycles (e.g., two), the power assembly (3100) may suspend operation (block 3166). Alternatively, if the instrument (10) does not believe a primary power pack (92) is connected, then another interrogation cycle may begin (block 3152), with or without an error warning (block 3164).

Referring back to the stage where it is determined whether the interrogation from instrument (10) is understood by processor (3116) of power assembly (3100)(block 3154), if the interrogation is not understood by the processor (3116), then the power assembly (3100) collects and stores information regarding the interrogation (block 3168) and may use the collected and stored information to re-program the processor (block 3170) in order to increase the chances that, during the next interrogation cycle, the processor (3166) understands the interrogation and/or is programmed to appropriately respond to the interrogation. In some examples, powering the instrument (10) on and off may allow software and/or algorithms within the power assembly (3100) (e.g., in the processor (3116)) to adapt and update in order to attempt to match the expectations of the instrument (10), but powering the instrument (10) on and off is not required for the power assembly (3100) to update as described.

In some examples, the step(s) of collection and storage of such information may be performed using a memory (not shown) on the power assembly (3100) itself, which then may communicate to parties such as the power assembly (3100) designer and manufacturer. For instance, the information could be transmitted back to a centralized system once the power assembly (3100) is coupled with, for example, a recharging/docking station. By way of example only, the recharging/docking station may be in communication with a centralized server or other processing system component via the internet, via a private network, via a cellular network, and/or via any other suitable means. Information collected from power assembly (3100) may be used to refine the performance of that particular power assembly (3100). In addition or in the alternative, the information may be used to improve the performance of other existing power assemblies (3100) and/or subsequently made power assemblies (3100). The information may be stored and used in any software or algorithms used in a power assembly (3100) such as one of the examples described herein; or in some other fashion. In instances where the information is received by a central station, the information may be conveyed from a central processor or database to other power assemblies (3100) in any suitable manner as will be apparent to those skilled in the art. While FIG. 25 shows that the collection and storage of information (block 3168) occurs when interrogation is not understood by the processor (3166) (block 3154) or if the processor (3166) is not programmed to respond to the interrogation (block 3156), such information may also be collected and stored at other stages of the interrogation cycle, for example.

In addition to or as an alternative to the data processing described above, power assembly (3100) may monitor duty cycle and usage data and may be operable to transmit such data to a centralized system when the power assembly (3100) is coupled with, for example, a recharging/docking station. The data may be used to modify certain characteristics of the particular power assembly (3100), to improve the performance of other existing power assemblies (3100), and/or to improve the performance of subsequently made power assemblies (3100). For example, the data may be used to modify the steady-state outputs of current or future power assemblies (3100) in order to maximize battery life, cell balance, and capacity based on cumulative data usage over time. Additionally or alternatively, when the power assembly (3100) is coupled with a recharging/docking station, bios or simple software updates may be uploaded to the power assembly (3100) as the power assembly manufacturer updates the operation algorithms and/or programs, or adds new medical devices whose primary power assemblies the secondary power assembly (3100) can emulate. In instances where a recharging/docking station is in communication with a manufacturer system and/or other kind of remote system, the communication link may be wired or wireless.

B. Exemplary Alternative Battery Pack with Instrument Detection Features

Figure 26:
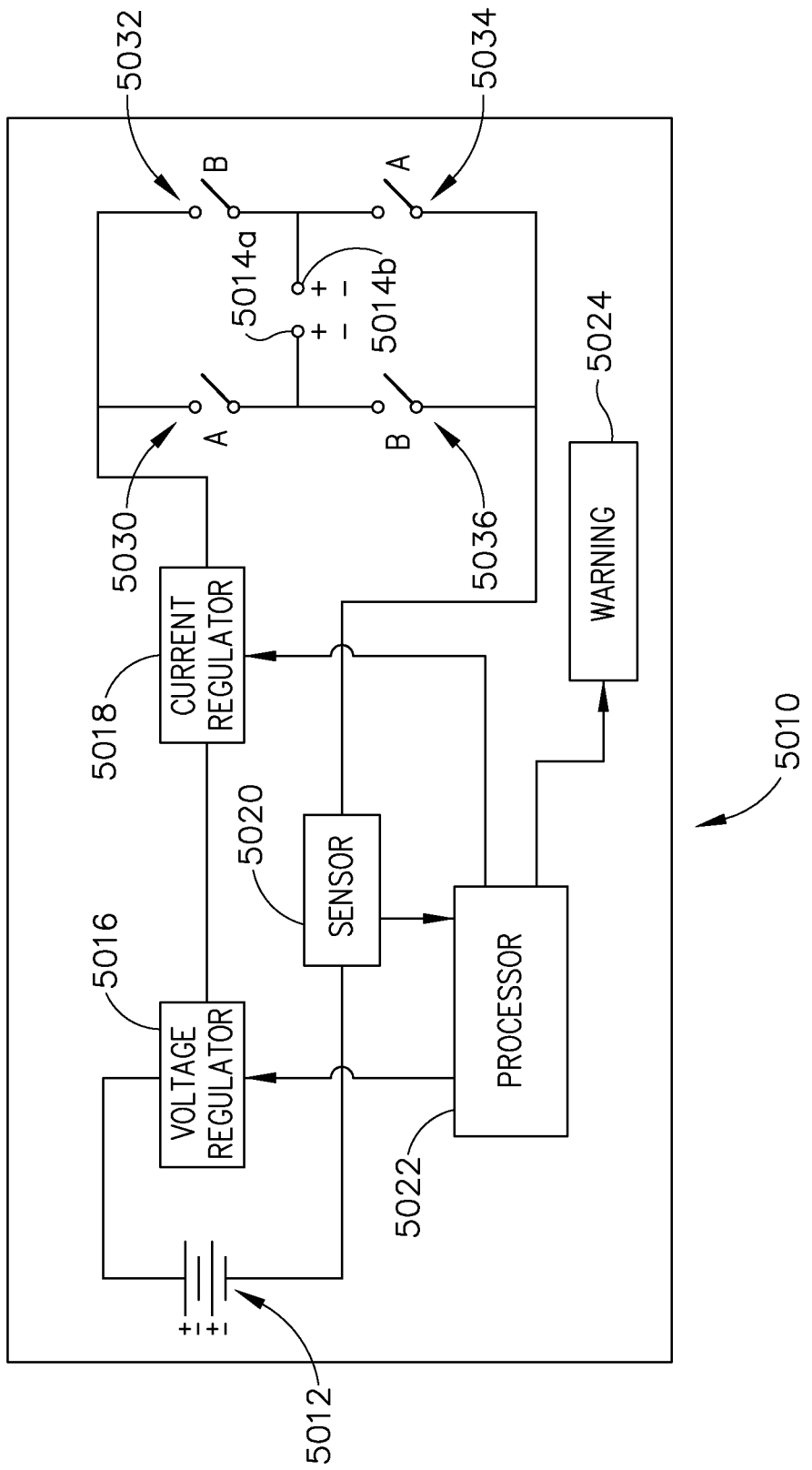
FIG. 26 depicts a schematic diagram of another exemplary circuit for another exemplary alternative power assembly of the instrument of FIG. 1.

FIG. 26 shows a schematic circuit diagram of another exemplary alternative power assembly (5010) that includes features that allows the power assembly (5010) to be used to provide power to a variety of kinds of medical devices having different power requirements. By way of example only, power assembly (5010) may be operable to provide power to surgical stapling instruments such as instrument (10), ultrasonic surgical instruments such as any of the various ultrasonic surgical instruments provided by Ethicon Endo-Surgery, Inc. of Cincinnati, Ohio, electrosurgical instruments such as any of the various electrosurgical instruments provided by Ethicon Endo-Surgery, Inc. of Cincinnati, Ohio, and/or any other kind of electrically powered medical devices. The physical appearance and other features of the power assembly (5010) may be configured according to the teachings above. For instance, the power assembly (5010) may be configured in a similar manner to the battery/power pack (92) shown in FIG. 4, but is not so limited. Power assembly (5010) may thus be mechanically and electrically coupled with the proximal end of handle assembly (14) in a manner similar to power pack (92).

The power assembly (5010) of the present example includes one or more features that enable it to sense or observe certain characteristics a medical device to which it is connected and adjust its own configuration in an attempt to become operationally compatible with the device. In some versions, the power assembly (5010) also includes features that enable it to adapt and learn after successful and unsuccessful attempts to become operationally compatible with the medical device to increase the likelihood of success of subsequent attempts with the same or different medical devices. It should be understood that power assembly (5010) may have the same components and functionalities described above with respect to power assembly (3100). Power assembly (5010) may thus be capable of convincing a medical device (e.g., instrument (10)) that power assembly (5010) is a primary power pack (92) that was originally provided with the medical device or that the medical device otherwise expects to be coupled with the medical device.

As shown, power assembly (5010) includes a set of battery cells (5012) that are operable to provide power output through terminals (5014a, 5014b). Battery cells (5012) may be rechargeable or non-rechargeable. Terminals (5014a, 5014b) may be provided as a set of contacts that are exposed through a distal housing portion of power assembly (5010) (e.g., similar to distal housing portion (96)). Terminals (5014a, 5014b) may thus be coupled with complementary contacts of a medical device (e.g., contacts in handle assembly (14), handle assembly (2002), working assembly (2054), etc.). As will be described in greater detail below, terminals (5014a, 5014b) do not have predetermined polarity in this example, such that the polarity may be assigned on an ad hoc basis. In particular, the circuit includes a set of switches (5030, 5032, 5034, 5036) that are interposed between terminals (5014a, 5014b) and the rest of the circuit of power assembly (5010). The circuit of power assembly (5010) is configured to provide switches (5030, 5034) in a closed state, while switches (5032, 5036) are in an open state, in order to provide terminals (5014a, 5014b) at a first polarity (A). The circuit of power assembly (5010) is further configured to provide switches (5032, 5036) in a closed state, while switches (5030, 5034) are in an open state, in order to provide terminals (5014a, 5014b) at a second polarity (B). Power assembly (5010) is operable to switch between these polarities (A, B) on an ad hoc basis in order to render power assembly (5010) operable with a variety of working assemblies (2054) and/or handle assemblies (14, 2002) having different power requirements. Examples of components and methods through which power assembly (5010) provides this polarity switching will be described in greater detail below.

In some examples, power assembly (5010) has the ability to observe or sense certain physical, electrical, electronic, or other characteristics of the medical device to which power assembly (5010) is coupled and adjust (or maintain) the polarity of the output terminals (5014a, 5014b) accordingly. In the example shown, the power assembly (5010) is configured to sense electrical characteristics of the medical device to which power assembly (5010) is coupled. Power assembly (5010) includes a voltage regulator (5016), a current regulator (5018), a sensor (5020) positioned to receive a return signal from the output terminals (5014a, 5014b) when the power assembly (5010) is connected to a medical device, as discussed in further detail below. A processor (5022) included in the power assembly (5010) communicates with the sensor (5020) and determines whether the return signal is appropriate based on the output signal sent, such as whether the polarity of the power assembly (5010) matches the polarity of the medical device. Power assembly (5010) also includes a warning device (5024) that is configured to provide a warning in a visual, audio, and/or another indicative manner. Various suitable kinds of components that may be used to form voltage regulator (5016), current regulator (5018), sensor (5020), processor (5022), and warning device (5024) will also be apparent to those of ordinary skill in the art in view of the teachings herein.

Figure 27:
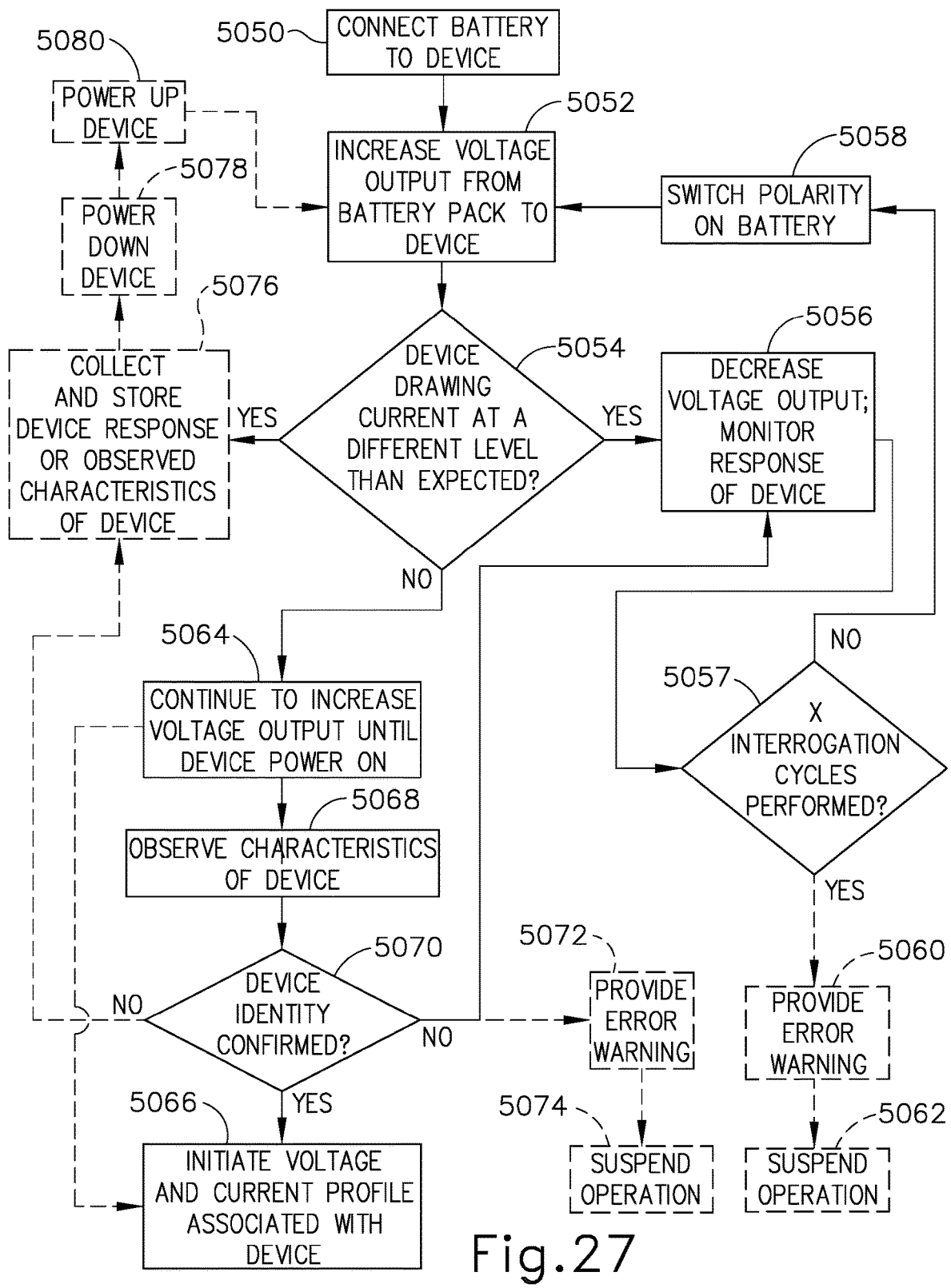
FIG. 27 depicts a flow chart showing steps carried out during one or more exemplary methods of utilizing the circuit of FIG. 26.

FIG. 27 shows an exemplary method that may be carried out by power assembly (5010). As shown, the method begins with a user connecting power assembly (5010) with a medical device (block 5050). Power assembly (5010) may detect this coupling in accordance with the teachings above with respect to power assembly (3100). Alternatively, power assembly (5010) may detect the coupling of power assembly (5010) with the medical device in any other suitable fashion as will be apparent to those of ordinary skill in the art in view of the teachings herein. In the example shown in FIGS. 26 and 27, after power assembly (5010) detects the coupling of power assembly (5010) with the medical device, power assembly (5010) begins an interrogation cycle of the medical device by sending an output signal to the medical device, via the output terminals (5014a, 5014b) of power assembly (5010) (block 5052). In some examples, the output signal is set to a first level of voltage by the voltage regulator (5016) as controlled by the processor (5022), with switches (5030, 5032, 5034, 5036) providing output terminals (4014s, 5014b) at a default polarity (A, B). In some such examples, the first level of voltage is insufficient to power the medical device for normal use; and may be low enough such that the medical device does not even detect the first level of voltage. This relatively low, first level of voltage may be deemed a "polling" voltage.

The voltage level of the signal is increased (block 5052) by the voltage regulator (5016) according to an input from the processor (5022). The sensor (5020) senses a return signal from the output terminals (5014a, 5014b) and communicates the return signal to the processor (5022). In one example, the sensor (5020) is a current sensor and therefore senses the current drawn by the medical device. However, in other examples, sensor (5020) may be a different type of sensor that senses different electrical or electronic characteristics of the return signal. In the present example, the processor (5022), based on the return signal, determines whether the medical device is drawing an appropriate amount of current according to, for example, a start-up operation of the medical device (block 5054). Determining whether the medical device is drawing an appropriate amount of current based at least in part on the output signal allows the power assembly (5010) to determine whether the polarities of the terminals (5014a, 5014b) and the medical device are matching at that stage.

If the medical device is drawing current at a different level than expected, for example, the power assembly (5010) may decrease the voltage output and monitor response of the medical device (block 5056). On the other hand, if the medical device begins to draw current at an expected level, then the medical device is known to the power assembly (5010) and the power assembly (5010) initiates an operational profile (e.g., current and voltage) associated with the known device. In the example shown, if the power assembly (5010) has performed less than a certain number of interrogation cycles (e.g., one or more) (block 5057), the power assembly (5010) switches polarities from the first polarity (A) to the second polarity (B), for example (block 5058). Once the polarity of the terminals (5014a, 5014b) has been switched, the power assembly (5010) may then begin another interrogation cycle, starting at block 5052, by increasing the voltage output from the power assembly (5010) to the shaft assembly as described herein. If, however, the power assembly (5010) has already performed a certain number of interrogation cycles (block 5057), the power assembly (5010) may decide not to switch polarity of the contacts, and instead may provide an error warning to the user (block 5060) and/or suspend operation (block 5062). The error warning may be provided by a visual, audio, and/or another indicative manner to the user and may be provided on one or both of the power assembly (5010) (e.g., via warning device (5024)) or the medical device; or on a device connected to one of the power assembly (5010) or the medical device. The number of interrogation cycles before providing an error warning may be two such that the power assembly (5010) has attempted to properly electrically connect with the medical device by switching between the first and second polarities (A, B). In some other versions, the number of interrogation cycles may be a different amount than two, and may be many more, as described below.

Referring back to the stage shown in block 5054, if the medical device is drawing an appropriate amount of current, operation continues and the processor (5022) may command the voltage regulator (5016) to increase the voltage output until the medical device powers on (block 5064). At this point, the processor (5022) may initiate the voltage and current profile associated with the medical device (block 5066) to initiate operation of the medical device. The power assembly (5010) optionally may observe or sense other characteristics of the medical device (block 5068) and confirm the identity of the medical device based on those characteristics (block 5070), in a manner discussed in more detail below, prior to initiating the voltage and current profile (block 5066). For instance, power assembly (5010) may initially provide a gradual voltage increase to detect if the medical device includes a reverse polarity protection circuit (e.g., a diode) that has been activated.

Once the identity of the medical device is confirmed, power assembly (5010) may subsequently initiate the voltage and current profile associated with the medical device (block 5066). In that regard, in the example shown in FIG. 26, the processor (5022) may set the voltage regulator (5016) and/or the current regulator (5018) to operation levels associated with the medical device. The voltage and current profile associated with the medical device may be constant or variable, and may be stored on a database, such as a database or other storage medium on a memory (not shown). The memory and/or database may be present on or in the power assembly (5010) itself. Alternatively or additionally, the database or part of the database may be in a nearby or remote memory and accessed according to methods that will be apparent to those skilled in the art. Additionally or alternatively, the power assembly (5010) may be configured to communicate electronically (wired, wirelessly, or otherwise) with other sources of information (e.g., manufacturer's specifications) in order to discover and/or initiate an operational profile associated with the medical device.

If the identity of the medical device is not confirmed (block 5070), for example, such that the power assembly (5010) is unable to confirm the identity for any variety of reasons, the power assembly (5010) could provide an error warning (block 5072) and suspend operation (block 5074). By way of example only, the error warning may be provided through warning device (5024). Alternatively, the power assembly (5010) could return to (block 5056) and decrease voltage output, and switch the polarity of terminals (5014*a*, 5014*b*) according to (block 5058), and begin another interrogation cycle as described herein (e.g., at block 5052).

In some examples, the power assembly (5010) is configured to adapt in the event that it cannot properly electrically connect to the medical device; e.g., where the initial polarity of polarity of terminals (5014*a*, 5014*b*) does not complement the polarity of the medical device. In that regard, still referring to FIG. 27, the power assembly (5010) may collect and store certain information (block 5076) if the medical device is determined to be drawing current at a different level than expected (e.g., at block 5054), for example, or after the device identity is not confirmed (e.g., at block 5070), or at other stages of the interrogation cycle. In that regard, as shown in block 5076, the power assembly (5010) may optionally collect and store the response of the medical device to the output signal of the power assembly (5010). Similarly, the power assembly (5010) may (additionally or alternatively) optionally collect and store the sensed or observed characteristics of the medical device, such as those characteristics described herein or other characteristics. While the flowchart shows that the collection and storage of information occurs if the medical device identity is not confirmed (e.g., blocks 5070, 5076), such information may also be collected and stored when the medical device identity is confirmed at block 5070, or if the medical device is drawing current at an expected level (block 5054). In other words, the power assembly (5010) may collect and store information whether or not it is able to successfully electrically connect to the medical device at any point during an interrogation cycle.

The power assembly (5010) may use the stored information in a subsequent attempt to match the polarity (and/or other characteristics) of the medical device to which it is connected. It may store the medical device or other device information for later use for itself or other power assemblies (5010), or both. If using the information in a subsequent attempt to match the polarity of the medical device, the power assembly (5010) may power down the medical device (block 5078) and subsequently power up the medical device (block 5080) and begin another interrogation cycle at, for example, (block 5052). In some examples, powering the device on and off may allow software and/or algorithms within the power assembly (5010) (e.g., in the processor (5022), etc.)) to adapt and update in order to attempt to match the medical device.

In some examples, the step(s) of collection and storage of such information may be performed using a memory (not shown) on the power assembly (5010) itself, which then may communicate to parties such as the power assembly (5010) designer and manufacturer. For instance, the information could be transmitted back to a centralized system once the power assembly (5010) is coupled with, for example, a recharging/docking station. By way of example only, the recharging/docking station may be in communication with a centralized server or other processing system component via the internet, via a private network, via a cellular network, and/or via any other suitable means. Information collected from power assembly (5010) may be used to refine the performance of that particular power assembly (5010). In addition or in the alternative, the information may be used to improve the performance of other existing power assemblies (5010) and/or subsequently made power assemblies (5010). The information may be stored and used in any software or algorithms used in a power assembly (5010) such as one of the examples described herein; or in some other fashion. In instances where the information is received by a central station, the information may be conveyed from a central processor or database to other power assemblies (5010) in any suitable manner as will be apparent to those skilled in the art.

Figures 1, 28:
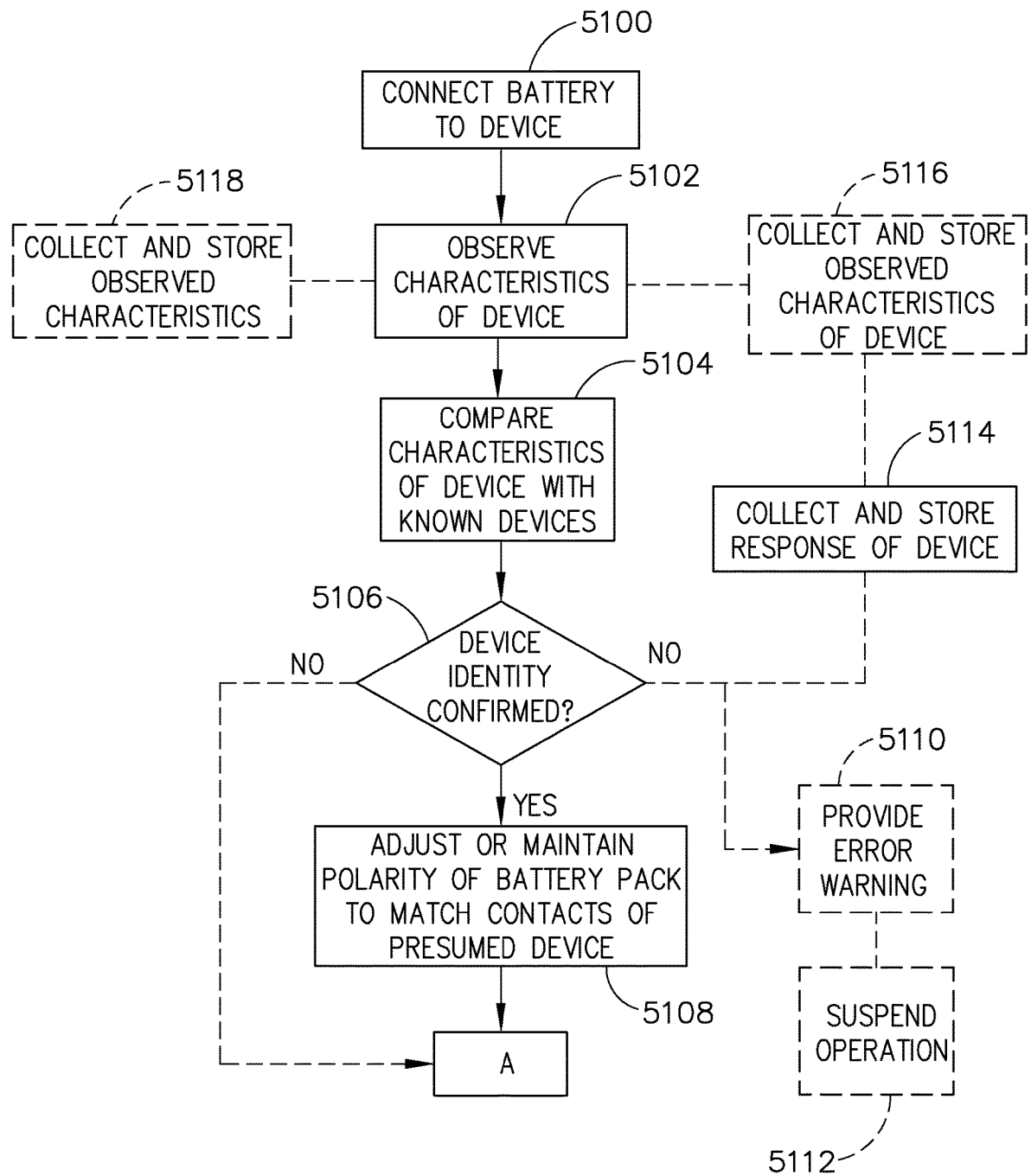
Figures 2, 28:
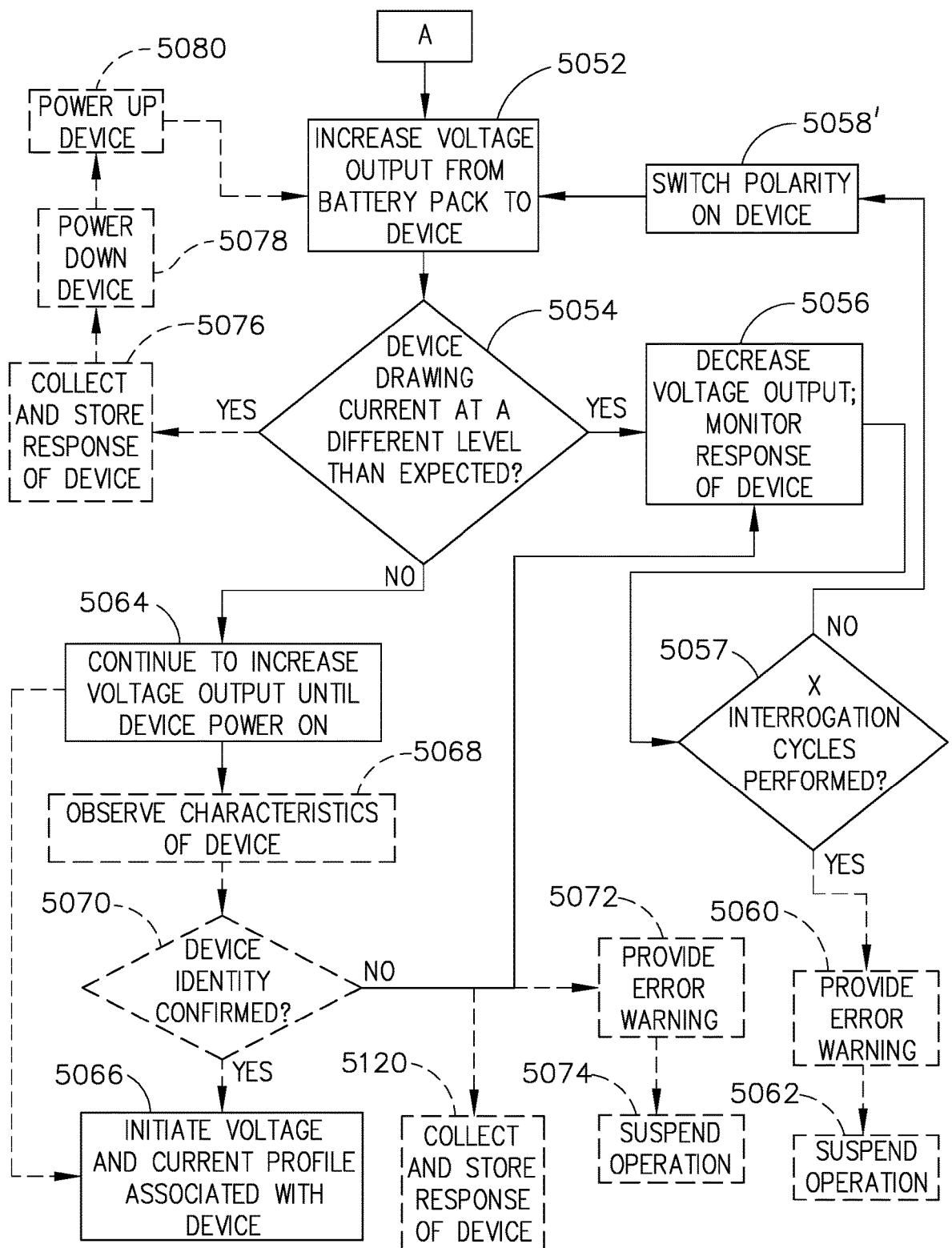

In other examples, referring to FIG. 28-1, in addition or in the alternative to sensing characteristics of a signal from a controller of a medical device, an interrogation cycle of the power assembly (5010) may include sensing certain other characteristics of the medical device. For example, once the power assembly (5010) is connected to the medical device (block 5100), the power assembly (5010) may be configured to sense other electrical, mechanical, and/or electronic characteristics or properties of the medical device (block 5102). For example, the power assembly (5010) may be configured to sense other electrical characteristics of the medical device such as internal resistance. In addition or in the alternative, the power assembly (5010) may include one or more inductance sensors configured to sense the presence of adjacent metallic members on the medical device when the power assembly (5010) is connected to or adjacent to the medical device. Therefore, the inductance sensor(s) may sense the presence (or lack thereof) and/or location of metallic contacts, for example, of the medical device and determine that it is connected to a particular known device. Other sensors could be employed to sense the physical characteristics (e.g. shape, size, etc.) of the receptacle area of the medical device that receives the power assembly (5010). For instance, the power assembly (5010) could include switches or sensors to detect mechanical or other features of the receptacle area or other portions of the medical device. Additionally or alternatively, the power assembly (5010) could include bar code readers, radiofrequency identification, or other electrical or electronic devices or sensors that could be used to identify at least some characteristics of the medical device or other portions of the medical device.

In some such examples, still referring to FIG. 28-1, the power assembly (5010) may access a database of characteristics of known medical devices (e.g., working assemblies of known medical devices) and compare the sensed characteristic to the characteristics of known medical devices to determine to which possible medical devices it is connected (block 5104). The database may be stored or included on a memory of the power assembly (5010) itself. Alternatively or additionally, the database or part of the database may be in a nearby or remote location and accessed according to methods that will be apparent to those skilled in the art. The database may include physical, electric, electronic, and other characteristics of known medical devices, or may be a collection of different physical, electric, electronic, or other characteristics that may or may not be associated with a particular known medical device. For example, the database may have voltage, amp rate, polarity, physical location of contacts, and other various information on a number of medical devices to which the power assembly (5010) may be connected.

Once the device identity is confirmed (block 5106), the polarity of the terminals (5014a, 5014b) may be maintained or adjusted by switches (5030, 5032, 5034, 5036) according to the presumed polarity of the medical device to which the power assembly (5010) believes it is connected (block 5108). In some examples, the electrical contacts thereof are moved physically with the goal of properly aligning the battery contacts with the contacts of the medical device. Alternatively, the polarity of the terminals (5014a, 5014b) may be switched by switches (5030, 5032, 5034, 5036). If the medical device identity is not confirmed at block 5106, for example, such that the power assembly (5010) is unable to confirm the identity for any variety of reasons, the power assembly (5010) could provide an error warning (block 5110) (e.g., via warning device (5024)) and suspend operation (block 5112). Alternatively, the power assembly (5010) could return to (block 5056) and decrease voltage output, and switch the polarity of terminals (5014a, 5014b) according to block 5108, and begin another interrogation cycle as described herein (e.g., at block 5052).

Once the polarity of the terminals (5014a, 5014b) has been switched, the power assembly (5100) may then begin another interrogation cycle, starting at block (5052) of FIG. 28-2, by commencing and increasing the voltage output from the power assembly (5010) to the medical device as described herein with respect to FIG. 27. The interrogation cycle shown in FIG. 28-2 is substantially identical to the interrogation cycle shown in FIG. 27, except that the interrogation cycle of FIG. 28-2 may be preceded by the initial interrogation cycle described and shown in FIG. 28-1, starting at (block 5102), for example. Therefore, blocks representing the same or similar steps are labeled with the same reference numerals. Notably, at block 5058', the polarity of the device, rather than the battery, is switched (see block 5058, FIG. 27). Moreover, in one example, if the power assembly (5010) is unable to confirm the medical device identity at (block 5106), the power assembly (5010) may skip the step of adjusting the polarity at (block 5108) and commence the interrogation cycle starting at block 5052.

Still referring to FIGS. 28-1 and 28-2, when sensing any of the above-mentioned or other characteristics, the power assembly (5010) may collect and store any information regarding the response and/or characteristics of the medical device and communicate with the database to add the observed characteristics of the medical device to the database at various times during the interrogation cycle (e.g., blocks 5114, 5116, 5118, 5120). The storage and collection of such information may be in a same or similar manner as the collection of information and/or data shown and describe relative to the method shown in FIG. 27. For example, if the power assembly (5010) is unsuccessful at properly electrically connecting with the medical device for any reason, or if the power assembly (5010) is successful at properly electrically connecting with the medical device, the power assembly (5010) may collect and store different characteristics that were sensed during an initial attempt to connect.

IV. Exemplary Alternative Power Processing Features of Medical Device

Figure 29:
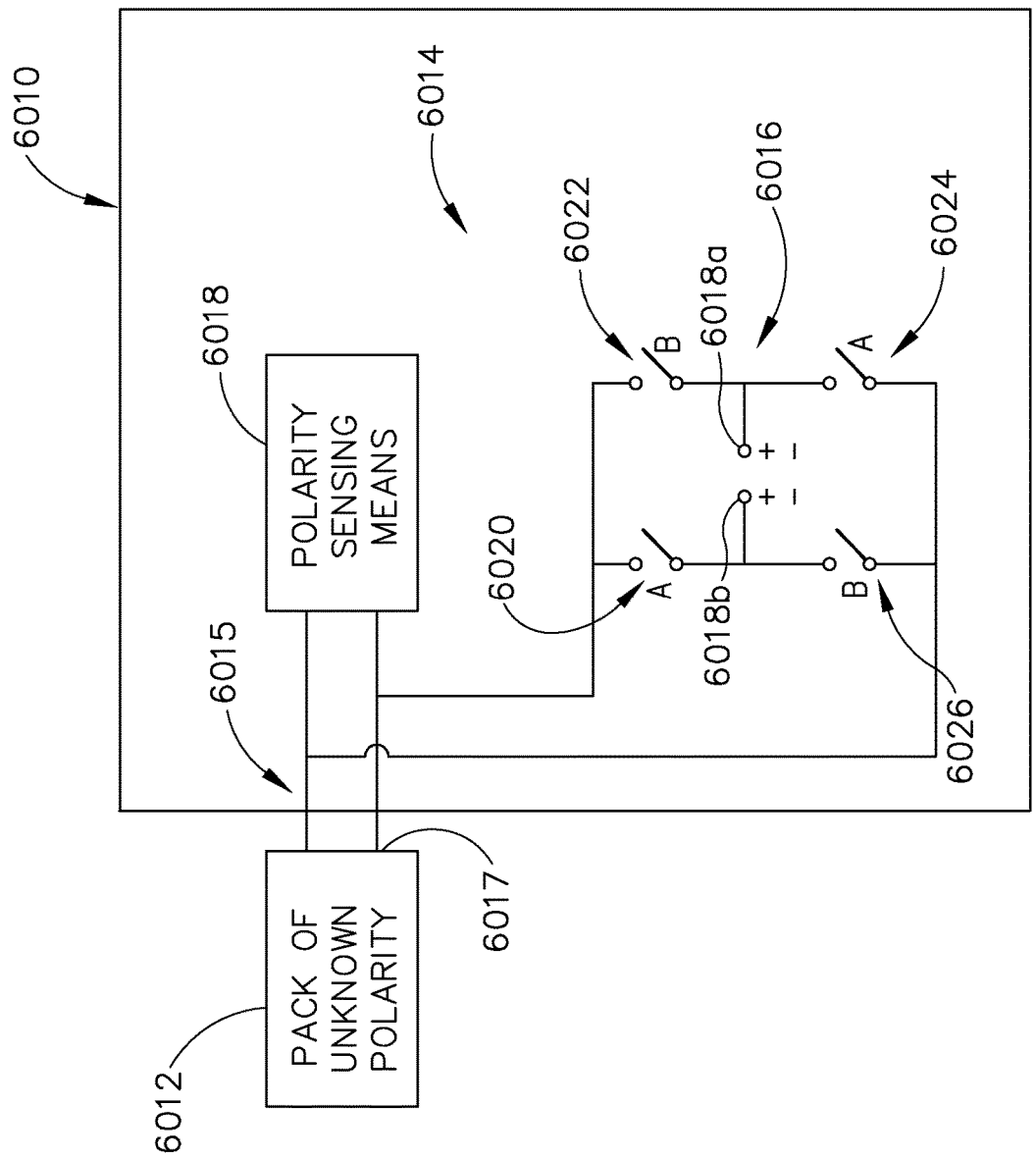
FIG. 29 depicts a schematic diagram of another exemplary circuit for a portion of an alternative exemplary power assembly of the instrument of FIG. 1.

FIG. 29 shows a schematic circuit diagram of an exemplary alternative medical device (6010) including features that that allow it to be used with a variety of battery packs or other power devices. In some examples, the device (6010) may be similar to the surgical instrument (10) shown in FIG. 1, but is not so limited. As shown in FIG. 29, the device (6010) is schematically shown to be connected to a battery pack or power assembly (6012) that may have characteristics (e.g., such as polarity) that are initially unknown to the device (6010). The device (6010) includes one or more features that enable it to sense or observe certain characteristics of the power assembly (6012) and adjust its own configuration in an attempt to become compatible with the power assembly (6012). As shown, such features are provided in a working assembly (6014) of a medical device (6010), such as working assembly (2054) (FIG. 15) described herein. However, these features may be provided in, for example, different portions of a medical device (6010), such as a handle assembly (e.g., handle assembly 2002 (FIGS. 12-1, 12-2, and 13)), or any portion of a body of a medical device described herein. Furthermore, the device (6010), in some examples, includes features that enable it to adapt and learn after successful and unsuccessful attempts to become operationally compatible with the power assembly (6012) to increase the likelihood of success of subsequent attempts with the same, similar, or different power assemblies (6012).

In that regard, the working assembly (6014) includes an interface (6015) having a power input (6016) that is configured to be connected to, and receive power from, an interface (6017) of power assembly (6012) shown in FIG. 29, via terminals (6018a, 6018b). Terminals (6018a, 6018b) may be provided as a set of contacts that are exposed through a distal housing portion of working assembly (6014). Terminals (6018a, 6018b) may thus be coupled with complementary contacts of a power assembly (6012) (e.g., contacts of power assembly (90)). As will be described in greater detail below, terminals (6018a, 6018b) do not have predetermined polarity in this example, such that the polarity may be assigned on an ad hoc basis. In particular, the circuit includes a set of switches (6020, 6022, 6024, 6026) that are interposed between terminals (6018a, 6018b) and the rest of the circuit of working assembly (6014). The circuit of working assembly (6014) is configured to provide switches (6020, 6024) in a closed state, while switches (6022, 6026) are in an open state, in order to provide terminals (6018a, 6018b) at a first polarity (A). The circuit of working assembly (6014) is further configured to provide switches (6022, 6026) in a closed state, while switches (6020, 6024) are in an open state, in order to provide terminals (6018a, 6018b) at a second polarity (B). Working assembly (6014) is operable to switch between these polarities (A, B) on an ad hoc basis in order to render working assembly (6014) operable with a variety of power assemblies (e.g., 90, 6012) having different polarities. Alternatively, working assembly (6014) may utilize a diode bridge (not shown) that enables the working assembly (6014) to be compatible with power assemblies (e.g., 90, 6012) having any polarity orientation. Examples of components and methods through which working assembly (6014) provides polarity switching via switches (6020, 6022, 6024, 6026) will be described in greater detail below.

In the example shown, the working assembly (6014) of medical device (6010) is configured to sense electrical characteristics of the power assembly (6012) that is connected to the device (6010). In that regard, the device (6010) includes a sensor (6018) that is operable to sense at least one characteristic of power assembly (6012). In the embodiment shown, the sensor (6018) is a polarity sensing device (6018) that is operable to sense the polarity of the power assembly (6012) that is connected to the working assembly (6014).

Figure 30:
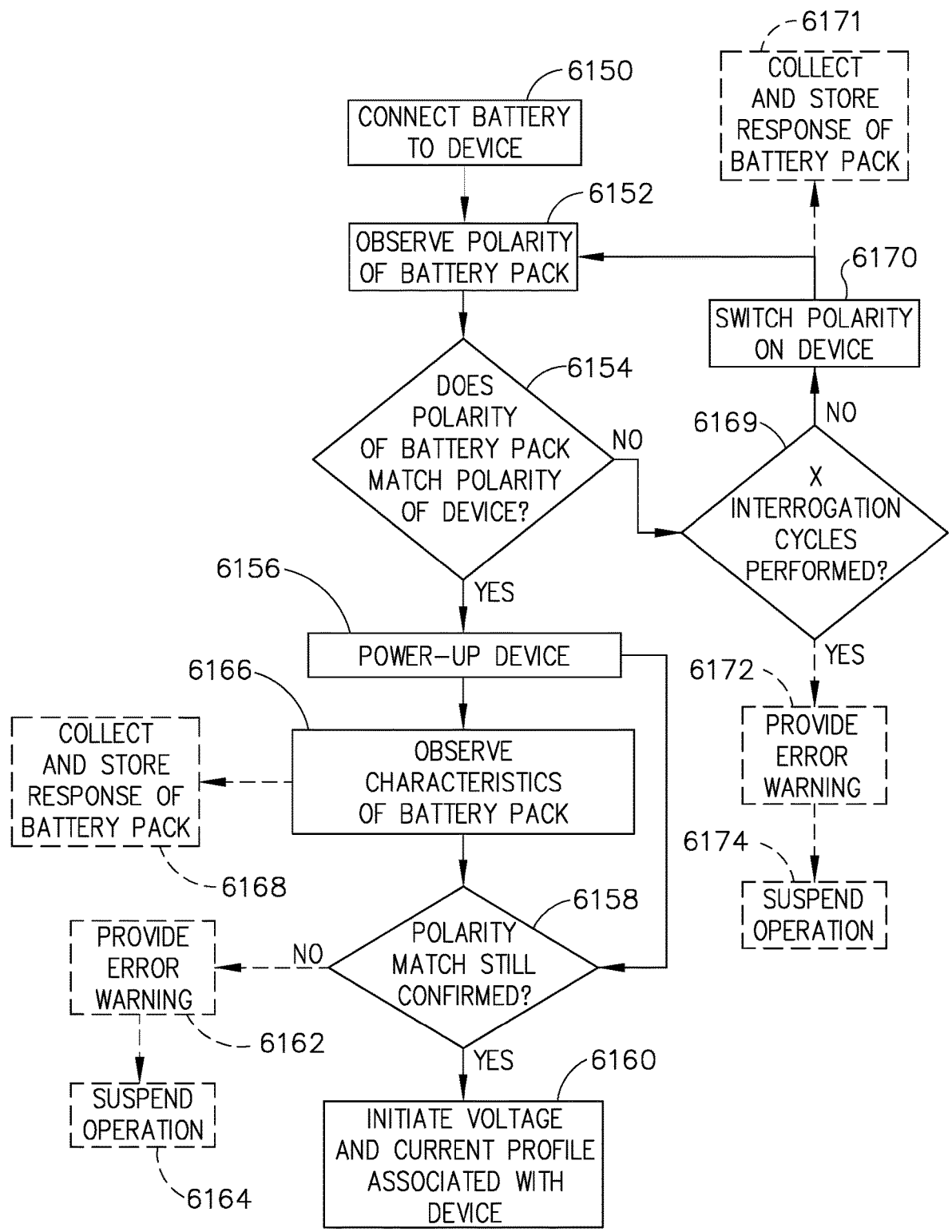
FIG. 30 depicts a flow chart showing steps carried out during one or more exemplary methods of utilizing the circuit of FIG. 29.

FIG. 30 shows an exemplary method that may be carried out by medical device (6010). As shown, the method begins with a user connecting power assembly (6012) to the medical device (6010) (block 6150). Medical device (6010) may detect this coupling in accordance with the teachings above with respect to power assembly (3100). Alternatively, medical device (6010) may detect the coupling of power assembly (6012) with the medical device (6010) in any other suitable fashion as will be apparent to those of ordinary skill in the art in view of the teachings herein. In the example shown in FIGS. 29 and 30, after the medical device (6010) detects the coupling of power assembly (6012) with medical device (6010), working assembly (6014) begins an interrogation cycle at (block 6152) by sensing and/or observing the polarity of the power assembly (6012) with the polarity sensing device (6018), for example. If the polarity of the power assembly (6012) matches the polarity of the working assembly (6014) (block 6154), the working assembly (6014) powers on (block 6156). After powering up, the medical device (6010) may determine if there is still a match between the polarities of the device (6010) and the power assembly (6012) (block 5158) and then initiate a voltage and current profile associated with the device (6010) in order to operate the working assembly (6014) (block 6160). The voltage and current profile associated with the working assembly (6014) may be constant or variable, and may be stored on a database, such as a database or other storage medium on a memory (not shown). The memory may be present on or in the device (6010). Alternatively or additionally, the database or part of the database may be in a nearby or remote memory and accessed according to methods that will be apparent to those skilled in the art. Additionally or alternatively, working assembly (6014) or power assembly (6012) may be configured to communicate electronically (wired, wirelessly, or otherwise) with other sources of information (e.g., manufacturer's specifications) in order to discover and/or initiate an operational profile associated with the working assembly (6014).

In some examples, after powering on, but before (or during) the initiation of the voltage and current profile (e.g., block 6160), the working assembly (6014) may optionally observe or sense at least one physical, electric, electronic, or other characteristic of the power assembly (6012), including the response of the power assembly (6012) to the working assembly (6014) being powered on (block 6166). The working assembly (6014) may then collect and store this information (block 6168). In some examples, the working assembly (6104) has the ability to observe or sense other certain physical, electrical, electronic, or other characteristics of the power assembly (6012) to which is connected and adjust (or maintain) the polarity of the terminals (6018a, 6018b) accordingly. For example, the working assembly (6014) may be configured to sense other electrical characteristics of the power assembly (6012) such as internal resistance, for example. In addition or in the alternative, the device (6010) may include one or more inductance sensors configured to sense adjacent metallic members on interface (6017) of the power assembly (6012) when the power assembly (6012) is connected to or adjacent to the working assembly (6014). Therefore, the inductance sensor(s) may sense the presence (or lack thereof) and/or location of metallic contacts, for example, of the power assembly (6012); and determine that it is connected to a particular known power assembly (6012). Other sensors could be employed to sense the physical characteristics (e.g. shape, size, etc.) of the body of the power assembly (6012), for example. For instance, the working assembly (6014) could include could include switches or sensors to detect mechanical or other features of the body of the power assembly (6012). Additionally or alternatively, the working assembly (6014) could include bar code readers, radiofrequency identification, or other electrical or electronic devices or sensors that could be used to identify at least some characteristics of the power assembly (6012).

Referring back to block 6154 of FIG. 30, if the polarity of the power assembly (6012) does not match the polarity of the working assembly (6014), and the working assembly (6014) has performed less than a certain number of interrogation cycles (block 6169), the polarity of the terminals (6018a, 6018b) is switched (block 6170) and the response of the working assembly (6014) or other sensed characteristics of the power assembly (6012) may be collected and stored (block 6171) in a memory. In some examples, the electrical contacts of the terminals (6018a, 6018b) of the working assembly (6014) are moved physically with the goal of properly aligning the contacts of the working assembly (6014) with the contacts of the power assembly (6012). Alternatively, the polarity of the terminals (6018a, 6018b) may be switched by switches (6020, 6022, 6024, 6026). Once the polarity of the terminals (6018a, 6018b) has been switched, the working assembly (6014) may then begin another interrogation cycle, starting at (block 6152), by observing the polarity of the power assembly (6012) as described herein above. If, however, the working assembly (6014) has already performed a certain number of interrogation cycles (block 6169), the device (6010) may not switch polarity of the terminals (6018a, 6018b) as shown in (block 6170), and may instead provide an error warning to the user (block 6172) and/or suspend operation (block 6174). The error warning may be provided by a visual, audio, and/or another indicative manner to the user and may be provided on one or both of the power assembly (6012) or the working assembly (6014); or on a device connected to one of the power assembly (6012) or the working assembly (6014). The number of interrogation cycles before providing an error warning may be two such that the working assembly (6014) has attempted to properly electrically connect with the power assembly (6012) by switching between the first and second polarities. However, the number of interrogation cycles may be a different amount than two, and may be many more.

In some examples, the working assembly (6014) is configured to adapt in the event that it cannot properly electrically connect to the power assembly (6012) (e.g., where the working assembly (6014) is unsuccessful in aligning the polarity of its contacts with the polarity of the contacts of the power assembly (6012)). While the flowchart shows that the collection and storage of information occurs at blocks 6171 and 6168, in other examples such information may also be collected and stored at other times during, before, or after the interrogation cycle. Moreover, the working assembly (6014) may collect and store information whether or not it is able to successfully electrically connect to the power assembly (6012) at any point during an interrogation cycle. The working assembly (6014) may optionally communicate the stored information to a database to add the observed characteristics of the power assembly (6012) to the database at various times during the interrogation cycle.

The working assembly (6014) may use the stored information in a subsequent attempt to match the polarity of the power assembly (6012) to which it is connected. It may store the power assembly (6012) information for later use for itself or other power assemblies (6012), or both. If using the information in a subsequent attempt to match the polarity of the power assembly (6012), the working assembly (6014) may power down and subsequently power up and begin another interrogation cycle at, for example, (block 6152). In some examples, powering the working assembly (6014) on and off may allow software and/or algorithms within the working assembly (6014) (e.g., in a processor) to adapt and update in order to attempt to match the power assembly (6012). In some examples, the step(s) of collection and storage of such information may be performed using a memory on the working assembly (6014) itself, which may then communicate to parties such as the device designer and manufacturer. The information may be stored and used in any software or algorithms used in a working assembly (6014) such as one of the examples described herein. Additionally or alternatively, the information may be conveyed to a central processor or database that may communicate this and other information to other devices in manners that will be understood by those skilled in the art.

V. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometric s, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A power device configured to provide power to a medical device, comprising:
  (a) a housing, wherein the housing is removably attachable to a medical device;
  (b) a battery supported by the housing;
  (c) an electrical connection feature operable to electrically couple with a complementary connection feature of the medical device, wherein the electrical connection feature is operable to deliver an output signal from the battery to the medical device, wherein the electrical connection feature is further operable to receive a return signal from the medical device; and
  (d) a processor, wherein the processor is operable to change a polarity of the electrical connection feature based at least in part on an electrical characteristic of at least one of the output signal or the return signal.

2. The power device of claim 1, further comprising a sensor in communication with the processor, wherein the sensor is operable to sense and generate a sensor signal based on an electrical characteristic of at least one of the output signal or the return signal, wherein the processor is operable to change the polarity of the electrical connection feature based at least in part on the sensor signal.

3. The power device of claim 2, wherein the sensor is in communication with the electrical connection feature, wherein the sensor is operable to receive the return signal from the electrical connection feature.

4. The power device of claim 2, wherein the sensor comprises a current sensor operable to measure a current of at least one of the output signal or the return signal.

5. The power device of claim 4, wherein the current sensor is operable to measure a current of the output signal, wherein the processor is operable to decrease a voltage of the output signal when the measured current differs from a predetermined current.

6. The power device of claim 5, further comprising a warning device, wherein the warning device is operable to provide an indication to a user when the measured current differs from the predetermined current.

7. The power device of claim 5, wherein the processor is operable to increase a voltage of the output signal when the measured current is equal to the predetermined current.

8. The power device of claim 1, further comprising a voltage regulator in communication with the processor, wherein the voltage regulator is operable to regulate a voltage of the output signal between a first level and a second level in response to a command from the processor, wherein the first level is insufficient to operate the medical device and the second level is sufficient to operate the medical device.

9. The power device of claim 1, wherein the electrical interface is arranged at a distal end of the housing.

10. The power device of claim 1, further comprising a plurality of switches in communication with the electrical connection feature, wherein the controller is operable to selectively open and close the switches to change the polarity of the electrical connection feature.

11. The power device of claim 1, wherein the power device is operable to sense a characteristic of the medical device, wherein the processor is operable to confirm an identity of the medical device based on the sensed characteristic.

12. The power device of claim 11, wherein the power device further comprises a warning device in communication with the processor, wherein the warning device is operable to provide an indication to a user when the processor is unable to confirm the identity of the of the medical device based on the sensed characteristic.

13. The power device of claim 1, wherein the power device further comprises a memory having a database of characteristics associated with a plurality of known medical devices, wherein the processor is operable to compare the sensed characteristic to the characteristics of the known medical devices, wherein the processor is operable to identify the medical device based on the comparison.

14. The power device of claim 1, wherein the processor is operable to determine whether a reverse-polarity protection circuit of the medical device is activated in response to the output signal being delivered to the medical device.

15. The power device of claim 1, wherein the power source is operable to collect and store data associated with a response of the medical device to the output signal.

16. A power device configured to provide power to a medical device, comprising:
 (a) a housing, wherein the housing is removably attachable to a medical device;
 (b) a battery supported by the housing;
 (c) an electrical connection feature configured to electrically couple with a complementary connection feature of the medical device;
 (d) a sensor operable to sense a characteristic of the medical device; and
 (e) a processor in communication with the sensor, wherein the processor is operable to identify the medical device based on the sensed characteristic, wherein the processor is further operable to change a polarity of the electrical connection feature based on the identification.

17. The power device of claim 16, wherein the processor is operable to access a database of characteristics of known medical devices, wherein the processor is operable to identify the medical device by comparing the sensed characteristic to the characteristics of the known medical devices.

18. The power device of claim 16, wherein the sensor is operable to sense an electrical characteristic of the medical device, wherein the processor is operable to identify the medical device based on the sensed electrical characteristic.

19. The power device of claim 16, wherein the sensor is operable to sense a physical characteristic of the medical device, wherein the processor is operable to identify the medical device based on the sensed physical characteristic.

20. A power device configured to provide power to a medical device, comprising:
 (a) a housing, wherein the housing is removably attachable to a medical device;
 (b) a battery supported by the housing;
 (c) an electrical connection feature configured to electrically couple with a complementary connection feature of the medical device;
 (d) a sensor operable to sense a characteristic associated with the medical device; and
 (e) a processor in communication with the sensor, wherein the processor is operable to change a polarity of the electrical connection feature based on the sensed characteristic.

* * * * *